United States Patent
Jaworsky et al.

(10) Patent No.: US 7,855,217 B2
(45) Date of Patent: *Dec. 21, 2010

(54) POLYMORPHIC FORMS OF 3-(4-AMINO-1-OXO-1,3 DIHYDRO-ISOINDOL-2-YL)-PIPERIDINE-2,6-DIONE

(75) Inventors: Markian S. Jaworsky, Hopewell, NJ (US); Roger Shen-Chu Chen, Edison, NJ (US); George W. Muller, Bridgewater, NJ (US)

(73) Assignee: Celgene Corporation, Summit, NJ (US)

( * ) Notice: Subject to any disclaimer, the term of this patent is extended or adjusted under 35 U.S.C. 154(b) by 82 days.

This patent is subject to a terminal disclaimer.

(21) Appl. No.: 12/335,395

(22) Filed: Dec. 15, 2008

(65) Prior Publication Data

US 2009/0149500 A1   Jun. 11, 2009

Related U.S. Application Data

(62) Division of application No. 10/934,863, filed on Sep. 3, 2004, now Pat. No. 7,465,800.

(60) Provisional application No. 60/499,723, filed on Sep. 4, 2003.

(51) Int. Cl.
   *A61K 31/454*   (2006.01)
   *C07D 401/04*   (2006.01)

(52) U.S. Cl. .................................. 514/323; 546/200

(58) Field of Classification Search ................ 514/323; 546/200
See application file for complete search history.

(56) References Cited

U.S. PATENT DOCUMENTS

| | | | |
|---|---|---|---|
| 3,536,809 A | 10/1970 | Applezwcig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,810,643 A | 3/1989 | Souza |
| 4,999,291 A | 3/1991 | Souza |
| 5,059,595 A | 10/1991 | Le Grazie |
| 5,073,543 A | 12/1991 | Marshall et al. |
| 5,120,548 A | 6/1992 | McClelland et al. |
| 5,229,496 A | 7/1993 | Deeley et al. |
| 5,354,556 A | 10/1994 | Sparks et al. |
| 5,385,901 A | 1/1995 | Kaplan et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,593,990 A | 1/1997 | D'Amato |
| 5,629,327 A | 5/1997 | D'Amato |
| 5,635,517 A | 6/1997 | Muller et al. |
| 5,639,476 A | 6/1997 | Oshlack et al. |
| 5,674,533 A | 10/1997 | Santus et al. |
| 5,698,579 A | 12/1997 | Muller |
| 5,712,291 A | 1/1998 | D'Amato |
| 5,731,325 A | 3/1998 | Andrulis, Jr. et al. |
| 5,733,566 A | 3/1998 | Lewis |
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 6,020,358 A | 2/2000 | Muller et al. |
| 6,071,948 A | 6/2000 | D'Amato |
| 6,114,335 A | 9/2000 | D'Amato |
| 6,114,355 A | 9/2000 | D'Amato |
| 6,140,346 A | 10/2000 | Andrulis, Jr. et al. |
| 6,235,756 B1 | 5/2001 | D'Amato |
| 6,281,230 B1 | 8/2001 | Muller et al. |
| 6,316,471 B1 | 11/2001 | Muller et al. |
| 6,326,388 B1 | 12/2001 | Man et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,420,414 B1 | 7/2002 | D'Amato |
| 6,458,810 B1 | 10/2002 | Muller et al. |
| 6,469,045 B1 | 10/2002 | D'Amato |
| 6,476,052 B1 | 11/2002 | Muller et al. |
| 6,518,298 B2 | 2/2003 | Green et al. |
| 6,555,554 B2 | 4/2003 | Muller et al. |

(Continued)

FOREIGN PATENT DOCUMENTS

JP   A H10-53576   2/1998

(Continued)

OTHER PUBLICATIONS

Dimartino et al., 1997, "Preparation and physical characterization of forms II and III of paracetamol," J. Thermal Analysis 48:447-458.

(Continued)

*Primary Examiner*—Celia Chang
(74) *Attorney, Agent, or Firm*—Jones Day

(57) ABSTRACT

Polymorphic forms of 3-(4-amino-1-oxo-1,3 dihydro-isoindol-2-yl)-piperidine-2,6-dione are disclosed. Compositions comprising the polymorphic forms, methods of making the polymorphic forms and methods of their use are also disclosed.

10 Claims, 48 Drawing Sheets

U.S. PATENT DOCUMENTS

Figure 1:
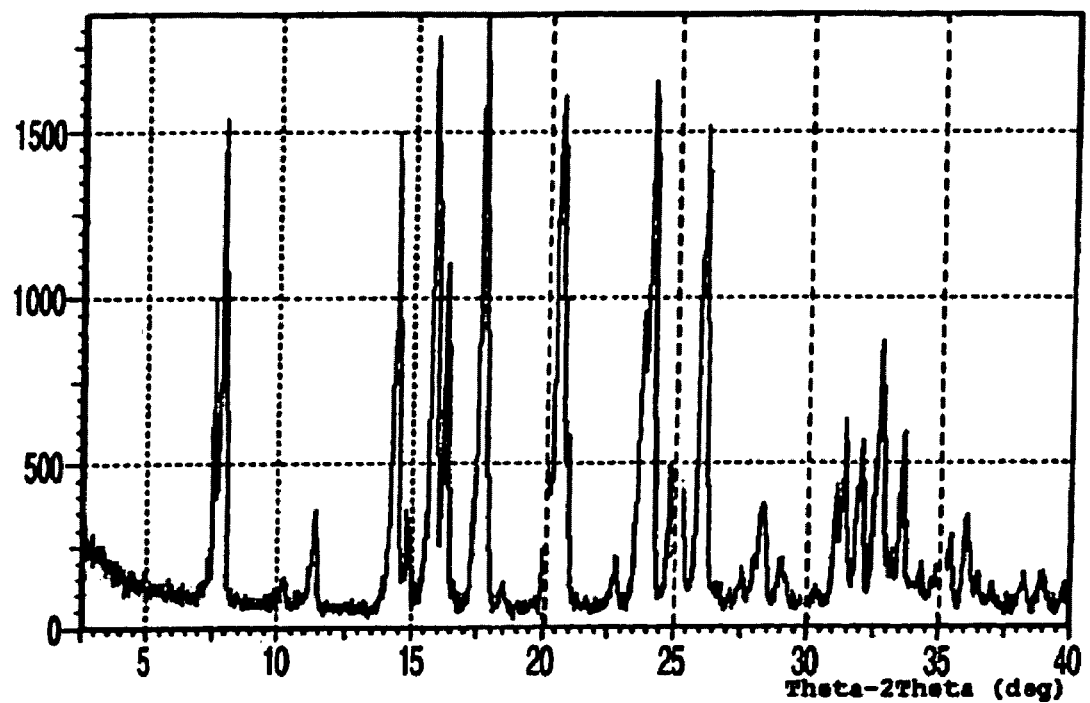

| | | | |
|---|---|---|---|
| 7,112,602 | B2 | 9/2006 | D'Amato et al. |
| 7,465,800 | B2 | 12/2008 | Jaworsky et al. |
| 2001/0018445 | A1 | 8/2001 | Huang et al. |
| 2001/0056114 | A1 | 12/2001 | D'Amato |
| 2002/0035090 | A1 | 3/2002 | Zeldis et al. |
| 2002/0045643 | A1 | 4/2002 | Muller et al. |
| 2002/0052398 | A1 | 5/2002 | D'Amato |
| 2002/0054899 | A1 | 5/2002 | Zeldis |
| 2002/0061923 | A1 | 5/2002 | D'Amato |
| 2002/0128228 | A1 | 9/2002 | Hwu |
| 2002/0161023 | A1 | 10/2002 | D'Amato |
| 2002/0173658 | A1 | 11/2002 | Muller et al. |
| 2002/0183360 | A1 | 12/2002 | Muller et al. |
| 2003/0013739 | A1 | 1/2003 | Masferrer et al. |
| 2003/0028028 | A1 | 2/2003 | Man et al. |
| 2003/0045552 | A1 | 3/2003 | Robarge et al. |
| 2003/0069428 | A1 | 4/2003 | Muller et al. |
| 2003/0096841 | A1 | 5/2003 | Robarge et al. |
| 2003/0139451 | A1 | 7/2003 | Shah et al. |
| 2003/0144325 | A1 | 7/2003 | Muller et al. |
| 2003/0181428 | A1 | 9/2003 | Green et al. |
| 2003/0187024 | A1 | 10/2003 | D'Amato |
| 2003/0191098 | A1 | 10/2003 | D'Amato |
| 2003/0235909 | A1 | 12/2003 | Hariri et al. |
| 2004/0029832 | A1 | 2/2004 | Zeldis |
| 2004/0077685 | A1 | 4/2004 | Figg et al. |
| 2004/0077686 | A1 | 4/2004 | Dannenberg et al. |
| 2004/0087546 | A1 | 5/2004 | Zeldis |
| 2004/0091455 | A1 | 5/2004 | Zeldis |
| 2004/0122052 | A1 | 6/2004 | Muller et al. |
| 2004/0220144 | A1 | 11/2004 | Zeldis |
| 2004/0266809 | A1 | 12/2004 | Emanuel et al. |
| 2005/0203142 | A1 | 9/2005 | Zeldis |
| 2006/0052609 | A1 | 3/2006 | Muller et al. |
| 2008/0064876 | A1 | 3/2008 | Muller et al. |
| 2008/0132541 | A1 | 6/2008 | Zeldis et al. |
| 2009/0062343 | A1 | 3/2009 | Jaworsky et al. |
| 2009/0149449 | A1 | 6/2009 | Liu et al. |
| 2009/0149499 | A1 | 6/2009 | Jaworsky et al. |
| 2009/0176832 | A1 | 7/2009 | Jaworsky et al. |
| 2009/0187023 | A1 | 7/2009 | Jaworsky et al. |

FOREIGN PATENT DOCUMENTS

| | | |
|---|---|---|
| JP | A 2001-503384 | 3/2001 |
| WO | WO97/46526 A1 | 12/1997 |
| WO | WO 98/03502 | 1/1998 |
| WO | WO98/03502 A1 | 1/1998 |
| WO | WO 98/54170 | 12/1998 |
| WO | WO 01/70275 | 9/2001 |
| WO | WO 01/87307 | 11/2001 |
| WO | WO 02/059106 | 8/2002 |
| WO | WO 02/064083 | 8/2002 |
| WO | PCT/US03/11578 | 1/2003 |
| WO | WO 03097052 | 11/2003 |
| WO | WO02/26737 A1 | 4/2004 |
| WO | WO 2004103274 | 12/2004 |
| WO | WO 2005023192 | 3/2005 |
| WO | WO 2006/028964 A1 | 3/2006 |
| WO | WO 2007/136640 A2 | 11/2007 |
| WO | WO 2009/111948 A1 | 9/2009 |
| WO | WO 2009/114601 A2 | 9/2009 |
| WO | WO 2010/054833 | 5/2010 |
| WO | WO 2010/056384 | 5/2010 |
| WO | WO 2010/061209 | 6/2010 |
| WO | WO 2010/100476 | 9/2010 |

OTHER PUBLICATIONS

Jonsson, 1972, "Chemical structure and teratogenic properties. 3. A review of available data on structure-activity relationships and mechanism of action of thalidomide analogues," Acta. Pharm. Suec. 9(6):521-542.

Wilen et al., 1977, "Strategies in optical resolutions," Tetrahedron 33:2725-2736.

Wilen, 1972, Tables of Resolving Agents and Optical Resolutions, Eliel, ed., U. Notre Dame Press, Notre Dame, IN pp. 268.

Wolff, ed., 1995, 1 Burger's Medicinal Chemistry and Drug Discovery, 5th ed., pp. 172-178 and 949-982.

Corral et al., 1999, "Immunomodulation by thalidomide and thalidomide analogs," Ann. Rheum. Dis. 58(Supp. 1):1107-1113.

Grant, 1999, "Theory and Origin of Polymorphism," in Polymorphism in Pharmaceutical Solids, Minneapolis, MN, Ch. 1, pp. 1-10.

He, W., et al., 1993, 206th American Chemical Society, Chicago, IL; Med. Chem., paper 216.

Lentzsch et al., 2002, "S-3-Amino-phthalimido-glutarimide inhibits angiogenesis and growth of B-cell neoplasias in mice," Cancer Research 62:2300-2305.

Muller et al., 1999, "Amino-substituted thalidomide analogs: Potent inhibitors of TNF-$\bar{\gamma}$ production," Bioorg. Med. Chem. Lett. 9:1625-1630.

Muller et al., 1998, "Thalidomide analogs and PDE4 inhibition," Bioorg. Med. Chem. Lett. 8:2669-2674.

Muller et al., 1996, "Structural modifications of thalidomide produce analogs with enhanced tumor necrosis factor inhibitory activity," J. Med. Chem. 39:3238-3240.

Anderson, "Moving disease biology from the laboratory to the clinic," *Seminars in Oncology*, 2002 29:17-20.

Barlogie et al., "High-dose therapy immunomodulatory drugs in multiple myeloma," *Seminars in Oncology*, 2002, 29 (6):26-33.

Barlogie et al., "Introduction: Thalidomide and the IMiDs in multiple myeloma," *Seminars in Hematology*, 2003, 40 (4):1-2.

Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," *Blood, Abstract # 2857*, Dec. 7-11, 2001, *American Society of Hematology*.

Barlogie, "Thalidomide and CC-5013 in Multiple Myeloma: The University of Arkansas experience." *Seminars in Hematology*, 2003, 40 (4):33-38.

Bartlett et al., "Phase I study to determine the safety, tolerability and immunostimulatory activity of thalidomide analogue CC-5013 in patients with metastatic malignant melanoma and other advanced cancers," *British Journal of Cancer*, 2004, 90:955-961.

Bartlett et al., "The evolution of thalidomide and its IMiD derivatives as anticancer agents," *Nature Reviews Cancer*, 2004, 4 (4):1-9.

Battegay, "Angiogenesis: mechanistic insights, neovascular diseases, and therapeutic prospects," *J. Mol. Med.*, 1995, 73:333-346.

Baz et al., "Doxil (D), vincristine (V), reduced frequency dexamethasone (d) and revlimid (R) (DVd-R) results in a high response rate in patients with refractory multiple myeloma (RMM)," *Blood, Abstract # 2559, American Society of Hematology*, Dec. 10-13, 2005.

Brennen et al., "Thalidomide and analogues: current proposed mechanisms and therapeutic usage," *Clinical Prostate Cancer*, 2004, 3 (1):54-61.

Celgene Corporation, "Additional clinical data presented on Revimid™ in myelodysplastic sydromes at the American Society of Hematology 45th annual meeting," Press Release, Dec. 2003.

Celgene Corporation, "Blood reports Revimid™ has anti-tumor activity in patients with relapsed and refractory multiple myeloma," Press Release, Nov. 1, 2002.

Celgene Corporation, "Celgene advances immunomodulatory drug (IMiD™) clinical program," Press Release, Feb. 2000.

Celgene Corporation, "Celgene announces plans to stop phase III trials in melanoma due to lack of efficacy," Press Release, Apr. 2004.

Celgene Corporation, "Celgene corporation advances ACTIMID™ (CC-4047) into phase II trial for prostate cancer," Press Release, Oct. 2003.

Celgene Corporation, "Celgene Corporation announces fourth quarter and full year results for 2002," Press Release, Jan. 2003.

Celgene Corporation, "Celgene Corporation announces third quarter results. THALOMID® (thalidomide) revenue increases 41% to $30.5 million. Pivotal programs for THALOMID and REVIMID™ finalized. Peer-reviewed publications of THALOMID and REVIMID data. First JNK inhibitor advanced to Phase I clinical trial," Press Release, Oct. 2002.

Celgene Corporation, "Celgene Corporation announces third quarter results. Thalomid® (thalidomide) sales increase 24%. Prescriptions up 50%. Enhanced S.T.E.P.S.® launched. Pilot d-MPH data presented," Press Release, Oct. 2001.

Celgene Corporation, "Celgene Corporation receives orphan drug designation for Revimid™ for multiple myeloma," Press Release, Oct. 2001.

Celgene Corporation, "Celgene corporation reports record operating performance in first quarter with strong revenue growth and profits," Press Release, Apr. 2004.

Celgene Corporation, "Celgene corporation reports record operating performance in third quarter as total revenue increases 117% and profits rise," Press Release, Oct. 2003.

Celgene Corporation, "Celgene corporation reports strong operating performance in second quarter as total sales increase 100 percent and profits rise," Press Release, Jul. 2003.

Celgene Corporation, "Celgene corporation reviews 2003 achievements and announces 2004 financial outlook," Press Release, Jan. 2004.

Celgene Corporation, "Celgene expands clinical development program for Revimid™. Five additional trials of Revimid initiated in hematological and solid tumor cancers," Press Release, Jun. 2002.

Celgene Corporation, "Celgene provides update on clinical pipeline. Celgene Announces first target indication for ACTIMID™, CC-8490. SelCID™ program to advance based on results from Phase I/II trial of CC-1088. First JNK inhibitor successfully completes phase I trial," Press Release, Jan. 2003.

Celgene Corporation, "Celgene receives fast track status from FDA for Revimid™ in multiple mylomia," Press Release, Feb. 2003.

Celgene Corporation, "Celgene receives fast track status from FDA for Revimid™ in myelodysplastic sydromes," Press Release, Apr. 2003.

Celgene Corporation, "Initial Phase I solid tumor data on Celgene's lead IMiD™, Revimid™," Press Release, Jun. 2001.

Celgene Corporation, "New Revimid™ clinical data shows potential as novel approach to treating myelodysplastic syndromes (MDS)," Press Release, May 2003.

Celgene Corporation, "Revlimid™ receives orphan drug designation from the European commission for multiple myeloma," Press Release, Feb. 2004.

Celgene Corporation, "Revlimid™ receives orphan drug designation from the European commission for myelodysplastic sydromes." Press Release, Mar. 2004.

Chaundhry, 1966, Cancer Research, "Effect of Prednisolone and Thalidomide on Induced Submandibular Gland Tumors in Hamster," 26(part 1)1884-86.

Corral et al., 1999, "Differential cytokine modulation and T cell activation by two distinct classes of thalidomide analogues that are potent inhibitors of TNF-alpha," J. Immunol. 163(1):380-386.

Craig et al., 1967, "Potential anticancer agents. III. 2-phthalimidoaldehydes and derivatives," Potential Anticancer Agents III 10:1071-1073.

D'Amato et al., 2001, "Mechanism of action of thalidomide and 3-aminothalidomide in multiple myeloma," Semin. Oncol. 28:597-601.

Dalgleish et al.. "Thalidomide analogues CC-5013 and CC-4047 induce T cell activation and IL-12 production in patients with both solid tumours and relapsed and refractory multiple myclema," British Journal of Cancer, 2003, 88(Suppl I). S25-S54.

Dalgleish, et al., "New thalidomide analogues; anti-cancer, anti-angiogenic and immunostimulatory," British Journal of Cancer, 2001, 85 (1)25.

Davies et al., "Thalidomide (Thal) and immunomodulatory derivatives (IMiDs) augment natural killer (NK) cell cytotoxicity in multiple myeloma ~MM)," Abstract # P222, VIIIth International Myeloma Workshop, May 4-8, 2001.

Davies et al., "Thalidomide (Thal) and immunomodulatory derivatives (IMiDs) augment natural killer (NK) cell cytotoxicity in multiple myeloma(MM))," Abstract # 3617, American Society of Hematology, Dec. 1-5, 2000.

Davies et al., 2001, "Thalidomide and immunomodulatory derivatives augment natural killer cell cytotoxicity in multiple myeloma," Blood 98(1):210-216.

Dibbs et al., "Thalidomide and thalidomide analogs suppress TNFα secretion by myocytes," Abstract # 1284, Circulation, 1998.

Dimopoulos et al., "Results of thalidomide and IMIDs in multiple myeloma,", Abstract # P12.1.4, International Multiple Myeloma Workshop, May 23-27, 2003.

Dimopoulos et al., "Study of lenalidomide plus dexamethasone versus dexamethasone alone in relapsed or refractory multiple myeloma (MM): Results of a phase 3 Study (MM-010)," Abstract # 6, American Society of Hematology, Dec. 10-13, 2005.

Dimopoulos et al., "Treatment of plasma cell dyscrasias with thalidomide and its derivatives," Journal of Clinical Oncology, Dec. 1, 2003, 21 (23)4444-4454.

Dimopoulos et al., 2004, "Primary treatment with puilsed melphalan, dexamethasone, thalidomide (MDT) for symptomatic patients with multiple myeloma $\leq 75$ years of age," Am. Soc. Hematol. $46^{th}$ Ann. Meeting Dec. 4-7, 2004, San Diego, CA Abstract # 1482.

Dredge et al., A costimulatory thalidomide analog enhances the partial anti-tumor immunity of an autologous vaccination in a model of colorectal cancer, Abstract # 491, American Association for Cancer Research, Apr. 6-10, 2002.

Dredge et al., "Adjuvants and the promotion of Th1-type cytokines in tumour immunotherapy," Cancer Immunol Immunother., 2002, 51:521-531.

Dredge et al., "Angiogenesis inhibitors in cancer therapy," Current Opinion in Investigational Drugs, 2003, 4 (6):667-674.

Dredge et al., "Immunological effects of thalidomide and its chemical and functional analogs," Critical Reviews in Immunology, 2002, 22 (5&6):425-437.

Dredge et al., "Protective antitumor immunity induced by a costimulatory thalidomide analog in conjunction with whole tumor cell vaccination is mediated by increased Th1-type immunity[1]," The Journal of Immunology, 2002, 168:4914-4919.

Dredge et al., "Recent developments in antiangiogenic therapy," Expert Opin. Biol. Ther., 2002, 2 (8):953-966.

Dredge et al., "Thalidomide analogs as emerging anti-cancer drugs," Anti-Cancer Drugs, 2003, 14:331-335.

Dredge et al., 2002, "Novel thalidomide analogues display anti-angiogenic activity independently of immunomodulatory effects," Br. J. Cancer 87(10):1166-1172.

Fickentscher et al., "Stereochemical properties and teratogenic activity of some tetrahydrophthalimides," Molecular Pharmacology, 1976, 13:133-141.

Galustian et al., "Thalidomide-derived immunomodulatory drugs as therapeutic agents," Expert Opin. Biol. Ther., 2004, 4 (12):1-8.

Glaspy et al., "The potential role of thalidomide and thalidomide analogs in melanoma," Clinical Advances in Hematology & Oncology, 2004, 1-7.

Gupta et al., "Adherence of multiple myeloma cells to bone marrow stromal cells upregulates vascular endothelial growth factor secretion: therapeutic applications," Leukemia, 2001, 15:1950-1961.

Haslett et al., 2003, "Thalidomide and a thalidomide analogue drug costimulate virus-specific CD8 + T cells in vitro," J. Infect. Dis. 187(6):946-955.

Hayashi et al., "Mechanisms whereby immunomodulatory analogs of thalidomide augment autologous NK cell anti-myeloma immunity," Blood, Abstract # 3219, Dec. 6-10, 2002, American Society of Hematology.

He, W., et al., 1993, Abstract of papers. $206^{th}$ American Chemical Society, Chicago, IL; Med. Chem., paper 216.

Helm et al., "Comparative teratological investigation of compounds of structurally arid pharmacologically related to thalidomide," Arzneimittel Forschung Drug Research, 1981, 31 (1)941-949.

Hernandez-Illizaliturr et al., "Addition of immunomodulatory drugs CC5013 or CC4047 to rituximab enhances anti-tumor activity in a severe combined immunodeficiency (SCID) mouse lymphoma model," Abstract # 235. *American Society of Hematology*, Dec. 6-9, 2003.

Hideshima et al., "Thalidomide (Thal) and its analogs overcome drug resistance of human multiple myeloma (MM) cells to conventional therapy," Abstract 1313. *American Society of Hematology*. Dec. 1-5, 2000.

Hideshima et al., "Thalidomide and its analogs overcome drug resistance of human multiple myeloma cells to conventional therapy," *Blood*. 2000. 96:2943-2950, *American Society of Hematology*.

Hunt et al., "Markers of endothelial and haemostatic activation in the use of CC-4047, a structural analogue of thalidannide, in relapsed myeloma," *Blood, Abstract* # 3216, Dec. 6-10, 2002, *American Society of Hematology*.

Hussein et al., "Doxil (D), vincristine (V), reduced frequency dexamethasone (d) and Revlimid (DVd-R) a phase I/II trial in advanced relapsed/refractory multiple myeloma (Rmm) patients," *Blood, Abstract* #208, *American Society of Hematology*, Dec. 4-7, 2004.

Kyle et al., "Multiple myeloma," *New England Journal of Medicine*, 2004, 351:1860-1873.

Kyle, "Current therapy of multiple myeloma," *Internal Medicine*, 2002, 41 (3)175-180.

Leblanc et al., "Immunomodulatory drug costimulates T cells via the B7-CD28 pathway," *Blood*, 2004, 103:1787-1790, *American Society of Hematology*.

Lentzsch et al., "Immunomodulatory derivative of thalidomide (IMiD CC-4047) determine the lineage commitment of hematopoietic progenitors by down regulation of GATA-1 and modulation of cytokine secretion," Abstract # 3073, *American Society of Hematology*, Dec. 6-9, 2003.

Lentzsch et al., "Immunomodulatory derivative of thalidomide (IMiD CC-4047) down regulates CAAT/enhancer-binding protein $^\beta$(C/EBP $^\beta$) in multiple myeloma (MM)," Abstract # 3456, *American Society of Hematology*, Dec. 6-9, 2003.

Lentzsch et al., "In vivo activity of thalidomide and immunomodulatory drugs against multiple myeloma," *VIIIth International Myeloma Workshop, Abstract* #P225, May 4-8, 2001.

Lentzsch et al., 2003, "Immunomodulatory analogs of thalidomide inhibit growth of Hs Sultan cells and angiogenesis in vivo," *Leukemia* 17(1):41-44.

Liu et al., "Phase I study of CC-5013 (Revimid), a thalidomide derivative, in patients with refractory metastatic cancer," *American Society of Oncology, Abstract* #927, 2003.

Luzzio et al., "Thalidomide analogues: derivatives of an orphan drug with diverse biological activity," *Expert Opin. Ther. Patents*, 2004, 14 (2):215-229.

Man et al., "α- Fluoro-substituted thalidomide analogues," *Bioorganic & Medicinal Chemistry Letters 13*, 2003, 3415-3417.

Marriott et al., "A novel subclass of thalidomide analogue with anti-solid tumor activity in which caspase-dependent apoptosis is associated with altered expression of bcl-2 family proteins'," *Cancer Research*, 2003, 63:593-599.

Marriott et al., "Immunotherapeutic and antitumour potential of thalidomide analogues," *Expert Opin. Biol. Ther.*, 2001, 1 (4):1-8.

Marriott et al., "New thalidomide analogues; anti-cancer, anti-angiogenic and immunostimulatory," *British Journal of Cancer*, 85:25, Jul. 6, 2001.

Marriott et al., "Thalidomide and its analogues have distinct and opposing effects on TNF-α and TNFR2 during co-stimulation of both CD4$^+$ and CD8$^+$ T cells," *Clin. Exp. Immunol*, 2002, 130:75-84.

Marriott et al., "Thalidomide derived immunomodulatory drugs (IMiDs) as potential therapeutic agents," *Current Drug Targets—Immune, Endocrine & Metabolic Disorders*, 2003, 3:181-186.

Masellis et al., "Changes in gene expression in bone marrow mesenchymal progenitor cells as a consequence of IMiD therapy in multiple myeloma patients," *Blood, Abstract* # 1548, Dec. 7-11, 2001, *American Society of Hematology*.

McCarty, "Thalidomide may impede cell migration in primates by down-regulating integrin β-chains: potential therapeutic utility in solid malignancies, proliferative retinopathy, inflammatory disorders, neointimal hyperplasia, and osteoporosis," *Medical Hypotheses*, 1997, 49:123-131.

Mitsiades et al., "Apoptic signaling induced by immunomodulatory thalidomide analogs (Imids) in human multiple myeloma cells: therapeutic implications," Abstract # 3224, Dec. 7-11, 2001, *American Society of Hematology*.

Mitsiades et al., "Apoptic signaling induced by immunomodulatory thalidomide analogs in human multiple myeloma cells: therapeutic implications," *Blood*, 2002, 99:4525-4530, *American Society of Hematology*.

Mitsiades et al., "CC-5013 Celgene," *Current Opinion in Investigational Drugs*, 2004, 5 (6):635-647.

Miyachi et al., 1997, "Novel biological response modifiers: phthalimides with tumor necrosis factor-alpha production-regulating activity," J. Med. Chem. 40:2858-2865.

Moutouh et al., "Novel immunomodulatory drugs (IMiDs®): A potential, new therapy for β-hemoglobinopathies," Abstract # 3740, *American Society of Hematology*, Dec. 4-7, 2004.

Patten et al., "The early use of the serum free light chain assay in patients with relapsed refractory myeloma receiving treatment with a thalidomide analogue (CC-4047)," Abstract # 1640, *American Society of Hematology*, Dec. 6-9, 2003.

Payvandi et al., "CC-5013 inhibits the expression of adhesion molecules ICAM-1 and CD44 and prevents metastasis of B16 F10 mouse melanoma cells in an animal model," *American Society of Clinical Oncology, Abstract* # 992, 2003.

Payvandi et al., "Effects of a thalidomide analog on binding activity of transcription factors and cell cycle progression of multiple myeloma cell lines," *Blood, Abstract* #2487. Dec. 1-5, 2000, *American Society of Hematology*.

Payvandi et al., "Immunomodulatory drugs inhibit expression of cyclooxygenase-2 from TNF-α, IL-Iβ, and LPS-stimulated human PBMC in a partially IL-10-dependent manner," *Cellular Immunology*, 2004, 81-88.

Payvandi ct al., "Thalidomide and IMiDS inhibit microvessel formation from human arterial rings in the absence of human liver microsomes," *Blood, Abstract* # 5046, Dec. 6-10, 2002, *American Society of Hematology*.

Payvandi et al., "Thaliomide analogs IMiDs inhibit expression of cyclooxygenase-2 in multiple myeloma cell line and LPS stimulated PBMCs," *Blood, Abstract* # 2689, Dec. 7-11, 2001, *American Society of Hematology*.

Payvandi Yvandi et al., "The thalidomide analogs IMiDs enhance expression of CD69 stimulatory receptor on natural killer cells," Abstract # 1793, *American Association for Cancer Research*, Mar. 24-28, 2001.

Raje et al., "Combination of the mTOR inhibitor rapamycin and CC-5013 has synergistic activity in multiple myeloma," *Blood*, Dec. 15, 2004, 104 (13)4188-4193.

Rajkumar et al., "Combination therapy with lenalidomide plus dexamethasone (Rev/Dex) for newly diagnosed myeloma," *Blood*, Dec. 15, 2005, 106 (13)4050-4053.

Richardson et al., "A multi-center, randomized, phase 2 study to evaluate the efficacy and safety of 2 CDC-5013 dose regimens when used alone or in combination with dexamethasone (Dex) for the treatment of relapsed or refractory multiple myeloma (MM)," *Blood, Abstract* # 825, *American Society of Hematology*, Dec. 6-9, 2003.

Richardson et al., "A multicenter, single-arm, open-label study to evaluate the efficacy and safety of single-agent lenalidomide in patients with relapsed and refractory multiple myeloma; preliminary results," *10$^{th}$ International Myeloma Workshop*, Apr. 10-14, 2005.

Richardson et al., "A Phase I study of oral CC5013, an immunomodulatory thalidomide (Thal) derivative, in patients with relapsed and refractory multiple myeloma (MM)," *Blood, Abstract* #3225, Dec. 7-11, 2001, *American Society of Hematology*.

Richardson et al., "A phase 1 trial of lenalidomide (REVLIMID®) with bortezomib (VELCADE® ) in relapsed and refractory multiple myeloma," *Blood, Abstract* # 365, *American Society of Hematology*, Dec. 10-13, 2005.

Richardson et al., "Immunomodulatory analogs of thalidomide: an emerging new therapy in myeloma," *Journal of Clinical Oncology*, 2004, 22(16) 3212-3214.

Richardson et al., "Immunomodulatory drug CC-55013 overcomes drug resistance and is well tolerated in patients with relapsed multiple myeloma," *Blood*, 2002 100:3063-3067, *American Society of Hematology*.

Richardson et al., "Novel biological therapies for the treatment of multiple myeloma," *Best Practice & Research Clinical Haematology*, 2005, 18 (4):619-634.

Rubin et al., "Principles of cancer treatment-1," 2003, 12 ONCO IV 1.

Schafer et al., "Enhancement of cytokine production and AP-1 transcriptional activity in T cells by thalidomide-related immunomodulatory drugs," *Journal of Pharmacology and Experimental Therapeutics*, 2003, 305(3)1222-1232.

Schey et al., "A phase I study of an immunomodulatory thalidomide analog, CC-4047, in relapsed or refractory multiple myeloma," *Journal of Clinical Oncology*, 2004, 22 (16):1-8.

Schey et al., "A phase I study of an immunomodulatory thalidomide analogue (CC4047) in relapse/refractory multiple myeloma," *International Society for Experimental Hematology, Abstract* #248, 2002.

Shah et al., 1999, "Synthesis and enantiomeric separation of 2-phthalimidino-glutaric acid analogues: potent inhibitors of tumor metastasis," J. Med. Chem. 42:3014-3017.

Shaughnessy et al., "Global gene expression analysis shows loss of C-MYC and IL-6 receptor gene mRNA after exposure of myeloma to thalidomide and IMiD," *Abstract* # 2485, *The American Society of Hematology*, Dec. I -5, 2000.

Shire et al., "TNF-α inhibitors and rheumatoid arthritis," *Exp. Opin. Ther. Patents*, 1998, 8 (5):531-544.

Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 2003, 28(5):425-431.

Streetly et al., "An update of the use and outcomes of the new immunomodulatory agent CC-4047 (Actimid) in patients with relapsed/refractory myeloma," *Abstract* #829, *American Society of Hematology*, Dec. 6-9, 2003.

Streetly et al., "Changes in neutrophil phenotype following the administration of CC-4047 (Actimid) to patients with multiple myeloma," *Abstract* # 2543, *American Society of Hematology*, Dec. 6-9, 2003.

Streetly et al., "Thalidomide analogue CC-4047 is effective in the treatment of patients with relapsed and refractory multiple myeloma (MM) and induces T-cell activation and IL-12 production," *Abstract* # 367, *International Multiple Myeloma Workshop*, May 23-27, 2003.

Teo et al., "A phase I, single-blind, placebo-controlled, ascending single oral dose, safety, tolerability and pharmacokinetic study of CDC-501, a novel immunomodulatory- oncologic agent, in healthy male subjects with a comparison of fed and fasted," *Clinical Pharmacology and Therapeutics*, 2002, 71 (2)93.

Teo et al., "Chiral inversion of the second generation IMiD™ CC-4047 (ACTIMID™) in human plasma and phosphate-buffered saline," *Chirality*, 2003. 15:348-351.

Thertulien et al., "Hybrid MEL/DT PACE autotransplant regimen for Multiple Myeloma (MM)- safety and efficacy data in pilot study of 15 patients," *Blood, Abstract* # 2869, *American Society of Hematology*, Dec. 7-11, 2001.

Tohnya et al., "A phase I study of oral CC-5013 (lenalidomide, Revlimid™ ), a thalidomide derivative, in patients with refractory metastatic cancer." *Clinical Prostate Cancer*, 2004, 2:241-243.

Tricot et al., "Angiochemotherapy (ACT) for multiple myloma (MM) with DT-PACE results in a high response rate, but in contrast to tandem transplants with melphalan does not affect durable disease control," *Blood, Abstract* # 3531, *American Society of Hermatology*, Dec. 7-11, 2001.

Tsenova et al., "Use of IMiD3, a thalidomide analog, as an adjunct to therapy for experimental tuberculous meningitis," *Antimicrobial Agents and Chemotherapy*, 2002, 46 (6)1887-1895.

Weber et al., "A multicenter, randomized, parallel-group, double-blind. placebo-controlled study of lenalidomide plus dexamethasone versus dexamethasone alone in previously treated subjects with multiple myeloma," *Abstract* # PO.738, *International Multiple Myeloma Workshop*, Apr. 10-14, 2005.

Weber, "Lenalidomide (CC-5013, Revlimid™ ) and other ImiDs," *Abstract* # PL5.02, *International Multiple Myeloma Workshop*, Apr. 10-14, 2005.

Ye et al., "Novel IMiD drugs enhance expansion and regulate differentiation of human cord blood CD34+ cells with cytokines," *Blood, Abstract* #4099, *American Society of Hematology*, Dec. 6-10, 2002.

Zangari et al, "Results of phase I study of CC-5013 for the treatment of multiple myeloma (MM) patients who relapse after high dose chemotherapy (HDCT)," *American Society of Hematology, Abstract* # 3226, 2001.

Zangari et al., "Revimid 25 mg (Rev 25) × 20 versus 50 mg (REV 50) × 10 q 28 days with bridging of 5 mg × 10 versus 10 mg × 5 as post-transplant salvage therapy for multiple myeloma (MM)," *Blood, Abstract* # 1642, *American Society of Hematology*, Dec. 6-9, 2003.

Zangari et al., "Risk factors for deep vein thrombosis (DVT) in a large group of myeloma patients (PTS) treated with thalidomide (Thal): The Arkansas Experience," *Blood, Abstract* # 681, *American Society of Hematology*, Dec. 7-11, 2001.

Zeldis et al., "Potential new therapeutics for Waldenstrom's macroglobulinemia," *Seminars in Oncology*, 2003, 30 (2):275-281.

Zeldis et al, "Update on the evolution of the IMiD™," *International Society for Biological Therapy of Cancer. Oral Abstract*, 2003.

Zhang et al., "CC-5079, a novel microtubule and TNF-α inhibitor with anti-angiogenic and antimetastasis activity," Abstract # B012, *International Conference on Molecular Targets and Cancer Therapeutics*, Nov. 17-21, 2003.

Haleblian, J.; McCrone, W.; "Pharmaceutical Applications of Polymorphism", Journal of Pharmaceutical Sciences, Aug. 1969, 58(8):911-929.

Davies, F.E.; et al., "Thalidomide and immunomodulatory derivatives augment natural killer cell cytotoxicity in multiple myeloma," Blood, Jul. 2001, 98(1):210-216.

Kyle, R.A.; Rajkumar, S.V., "Therapeutic Application of Thalidomide in Multiple Myeloma," Seminars in Oncology, Dec. 2001, 28(6):583-587.

USPTO Office Action dated Dec. 31, 2007 in currently pending U.S. Appl. No. 10/438,213.

Office Action dated Apr. 16, 2010 in corresponding Japanese Patent Application No. 2006-525471 (with summary).

USPTO Office Action dated Oct. 10, 2007 in U.S. Appl. No. 7,465,800.

Bernstein, 2002, Polymorphism in Molecular Crystals, Clarendon Press, 115-18.

Bernstein, 2004, "Crystal Structure Prediction and Polymorphism," ACA Transactions, 39, 14-23.

Bond et al., 2002, "Controlling Crystal Architecture in Molecular Solids: the Supramolecular Approach," *in* Supramolecular Organization and Materials Design, Jones & Rao eds., Cambridge University Press, Chapter 12, pp. 391-443.

Brittain, 1999, "Methods for the Characterization of Polymorphs and Solvates," *in* Polymorphism in Pharmaceutical Solids, Brittain ed., Chapter 6, pp. 227-278.

Brittain, 2002, "Polymorphism: Pharmaceutical Aspects," *in* Encyclopedia of Pharmaceutical Technology, $2^{nd}$ Edition, vol. 3, Swarbrick & Boylan eds., pp. 2239-2249.

U.S. Appl. No. 60/499,723, filed Sep. 4, 2003, Jaworsky.
U.S. Appl. No. 60/372,348, filed Apr. 12, 2002, Hariri et al.
U.S. Appl. No. 09/545,654, filed Apr. 10, 2000, D'Amato.
U.S. Appl. No. 09/287,377, filed Apr. 7, 1999, D'Amato.

Brittain, 2007, "Polymorphism and Solvatomorphism 2005," Journal of Pharmaceutical Sciences, 96(4), 705-28.

Bruns et al., 1984, "Thermochemical Investigation of Theophylline, Theophylline Hydrate and Their Aqueous Solutions," Thermochimica Acta, 72, 31-40.

Byrn et al., 1999, "Drugs as Molecular Solids," *in* Solid-State Chemistry of Drugs, $2^{nd}$ Edition, Chapter 1, pp. 3-43.

Cruz Cabeza et al., 2006, "Prediction and Observation of Isostructurality Induced by Solvent Incorporation in Multicomponent Crystals," J. Am. Chem. Soc., 128, 14466-67.

Cruz Cabeza et al., 2007, "Importance of Molecular Shape for the Overall Stability of Hydrogen Bond Motifs in the Crystal Structures of Various Carbamazepine-Type Drug Molecules," Crystal Growth & Design, 7(1), 100-07.

Day et al., 2004, "An Assessment of Lattice Energy Minimization for the Prediction of Molecular Organic Crystal Structures," Crystal Growth & Design, 4(6), 1327-40.

Day et al., 2006, "Investigating the Latent Polymorphism of Maleic Acid," Chemical Communications, 54-56.

Dean, 1993, Analytical Chemistry Handbook, 10.24-10.26.

Gadamasetti et al., 2007, "Process Chemistry in the Pharmaceutical Industry," in Encyclopedia of Pharmaceutical Technology, $3^{rd}$ Edition, vol. 5, Swarbrick ed., pp. 2993-3007.

Jones et al., 2006, "Pharmaceutical Cocrystals: An Emerging Approach to Physical Property Enhancement," MRS Bulletin, 31, 875-79.

Kirk-Othmer, 2002, "Crystallization," in Encyclopedia of Chemical Technology, vol. 8, pp. 95-147.

Knapman, 2000, "Polymorphic Predictions," Modern Drug Discovery, 3(2), 53-57.

Office Action dated Jun. 18, 2010 in U.S. Appl. No. 12/220,336.

Richardson et al., "A Multi-Center, Randomized, Phase II Study To Evaluate the Efficacy and Safety of Two CDC-5013 Dose Regimens When Used Alone or in Combination with Dexamethasone (Dex) for the Treatment of Relapsed or Refractory Multiple Myeloma (MM)," *Blood*, Journal of the American Society of Hematology, Dec. 6-10, 2002, 100(11):Abstract #386.

Seddon, 2004, "Pseudopolymorph: A Polemic," Crystal Growth & Design, 4(6), 1087.

Sharma et al., 2006, "Toxicity Profile of the Immunomodulatory Thalidomide Analogue, Lenalidomide: Phase I Clinical Trial of Three Dosing Schedules in Patients with Solid Malignancies," European Journal of Cancer, 42, 2318-25.

Vippagunta et al., 2001, "Crystalline Solids," Advanced Drug Delivery Reviews, 48, 3-26.

Caira, 1998, "Crystalline Polymorphism of Organic Compounds," Topics in Current Chemistry, 198, 163-208.

Fauci et al, 1998, "Harrison's Principles of Internal Medicine, Chronic Visual Loss," in Harrison's Principles of Internal Medicine, 168.

Notice of Allowability mailed Nov. 3, 2008 in U.S. Appl. No. 10/934,863.

Office Action mailed Jun. 17, 2010 in U.S. Appl. No. 10/557,302.

Figure 31:
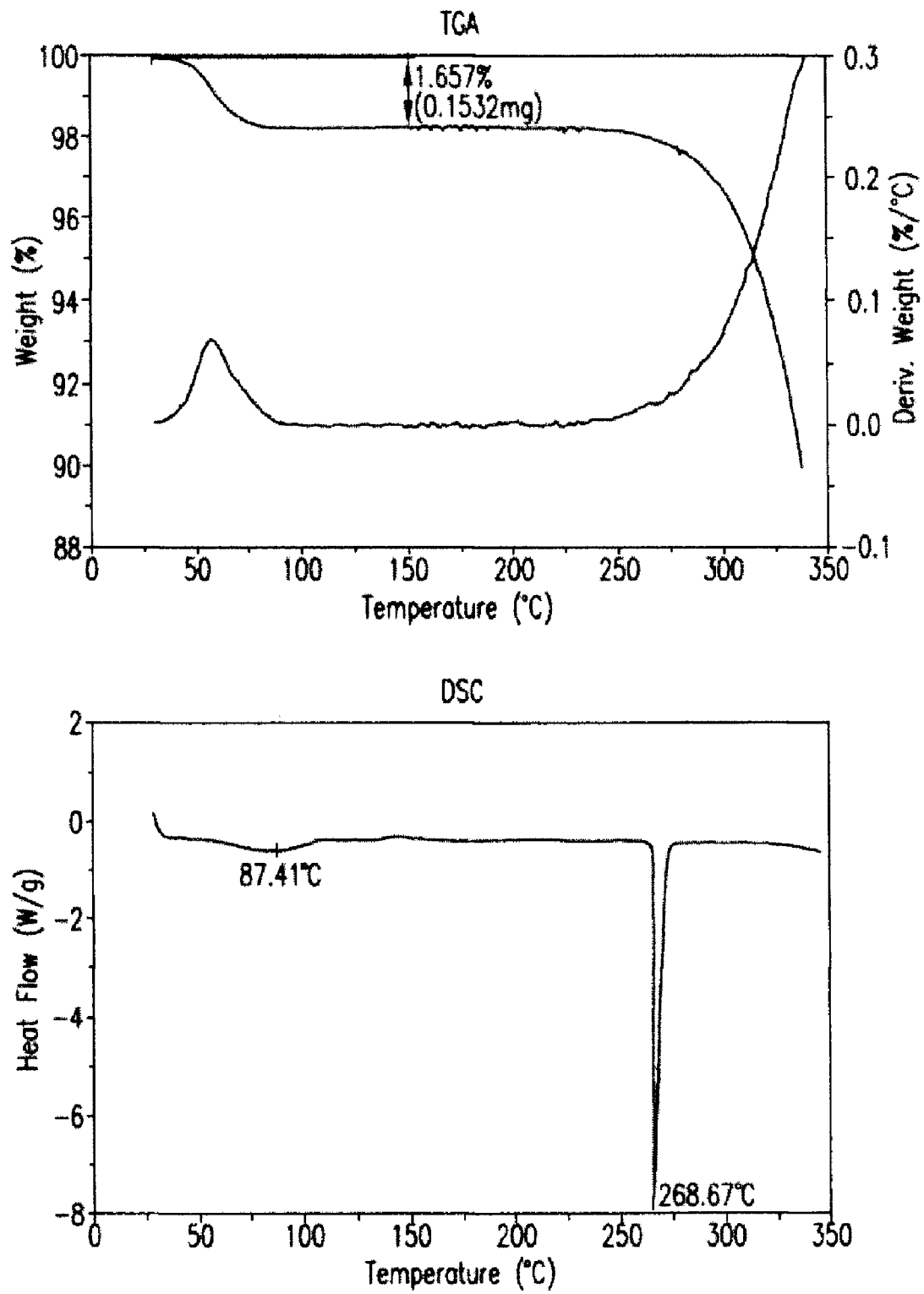
Figure 32:
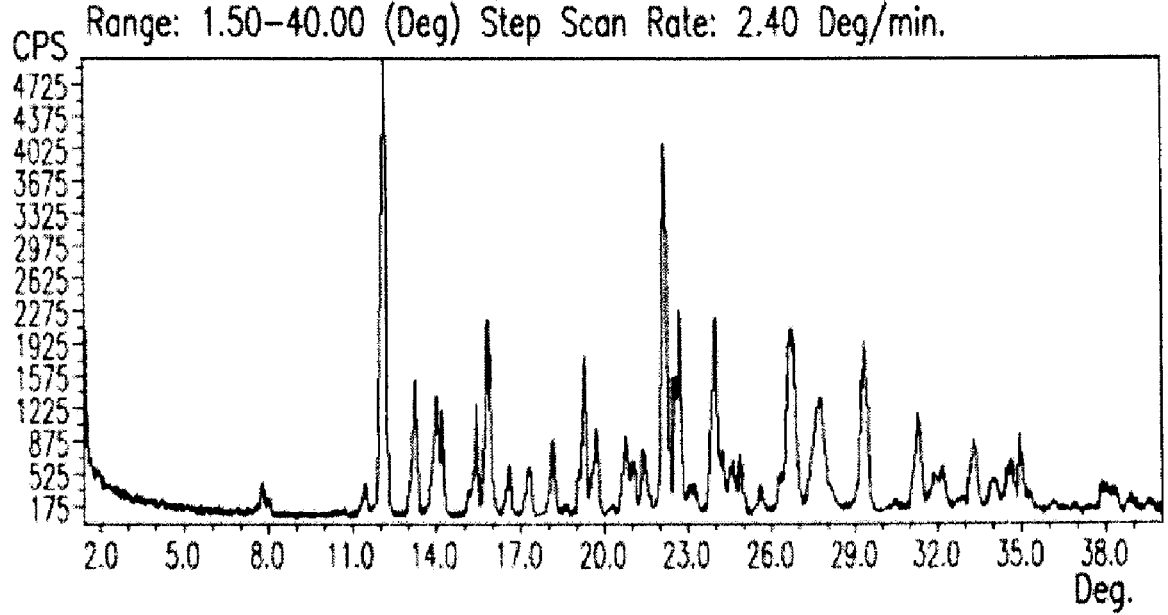
Figure 33:
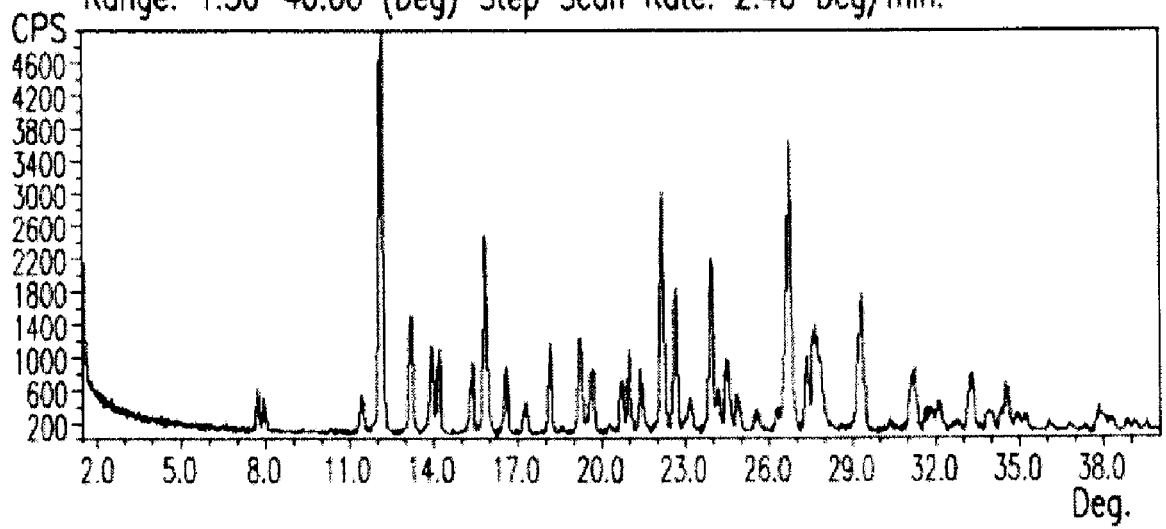
Figure 34:
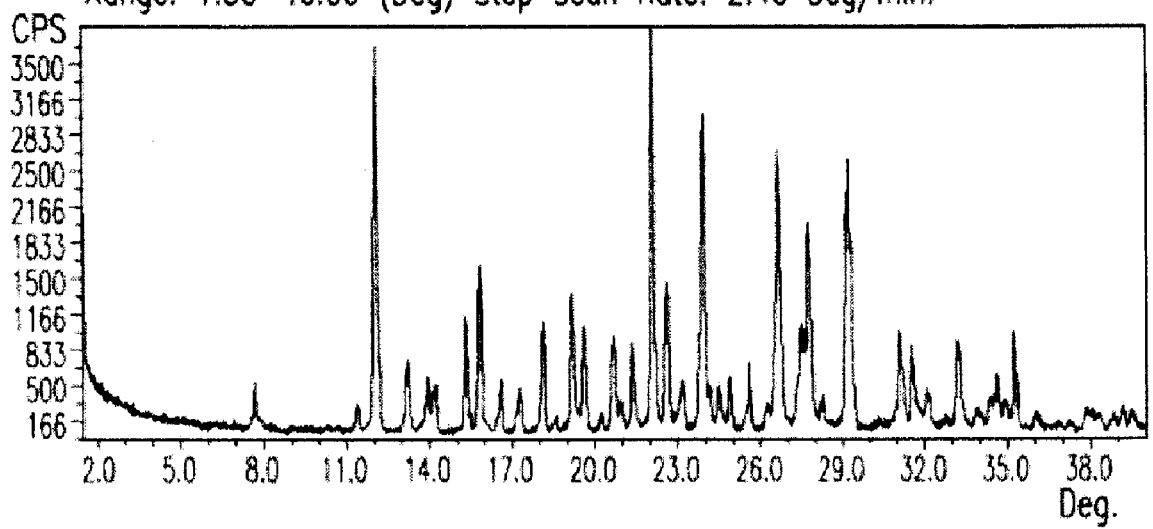
Figure 35:
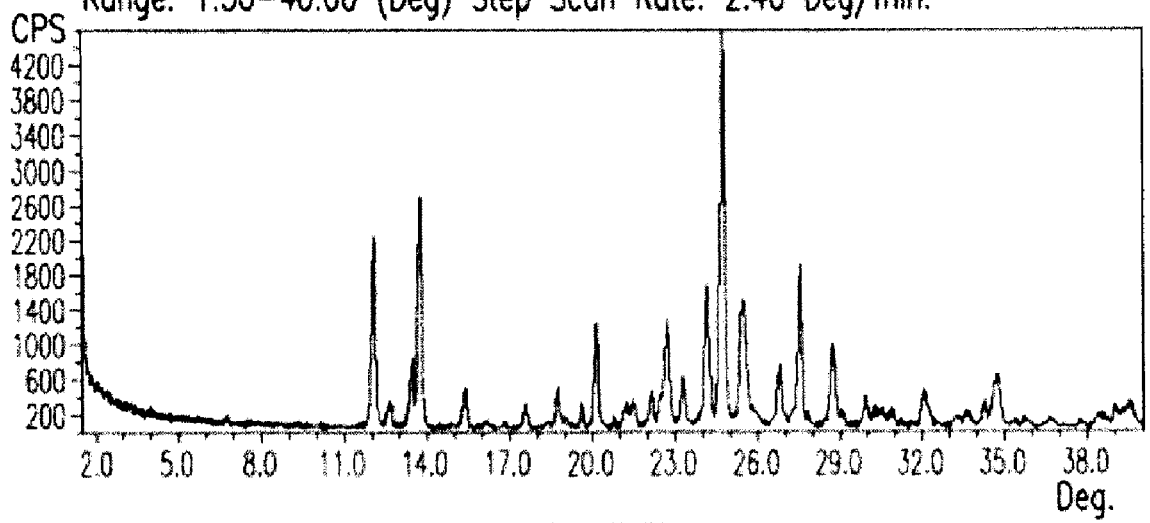
Figure 37:
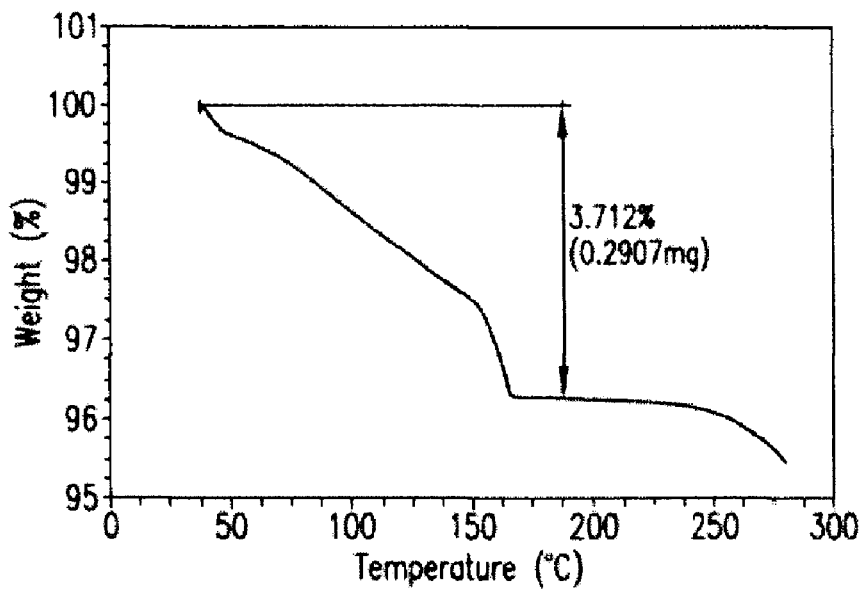
Figure 38:
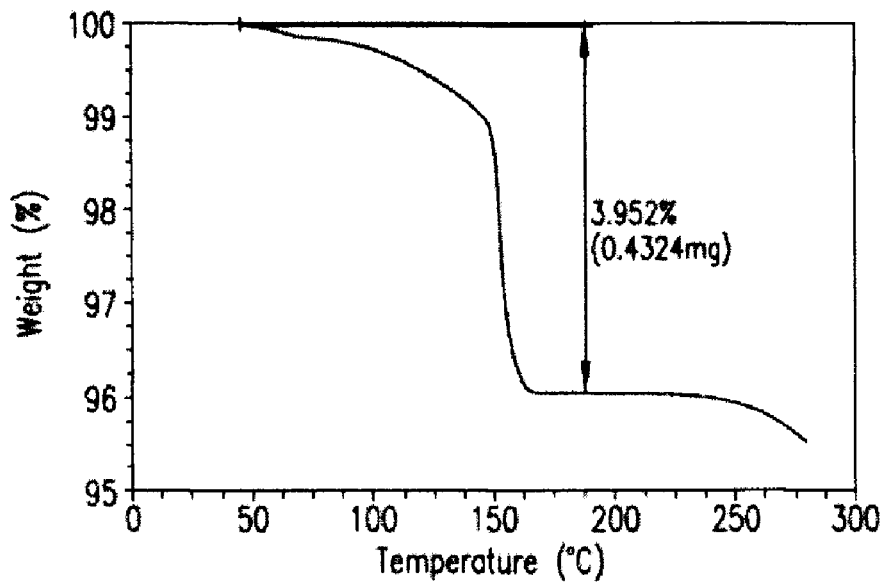
Figure 39:
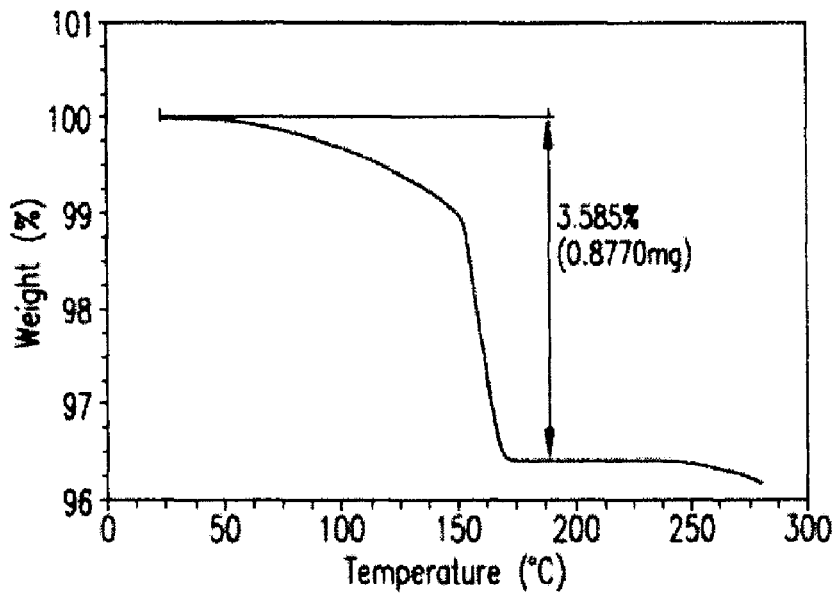
Figure 40:
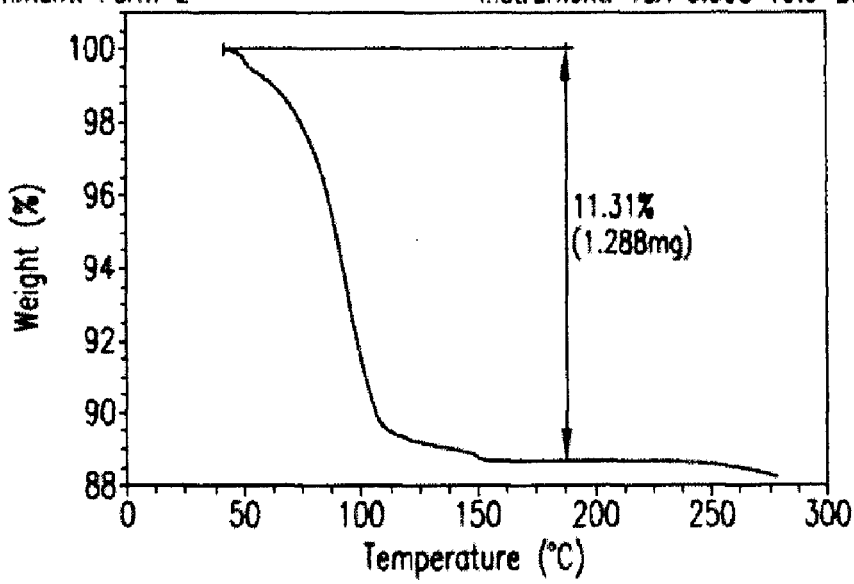
Figure 42:
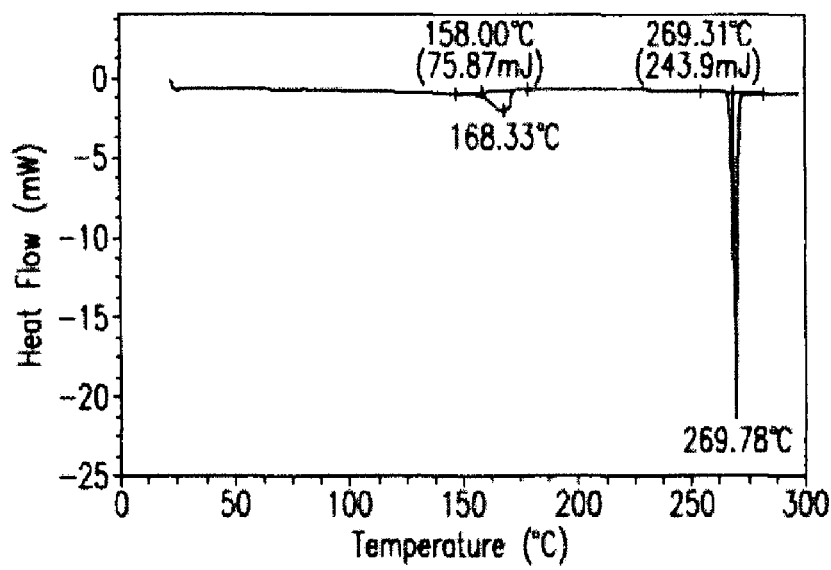
Figure 43:
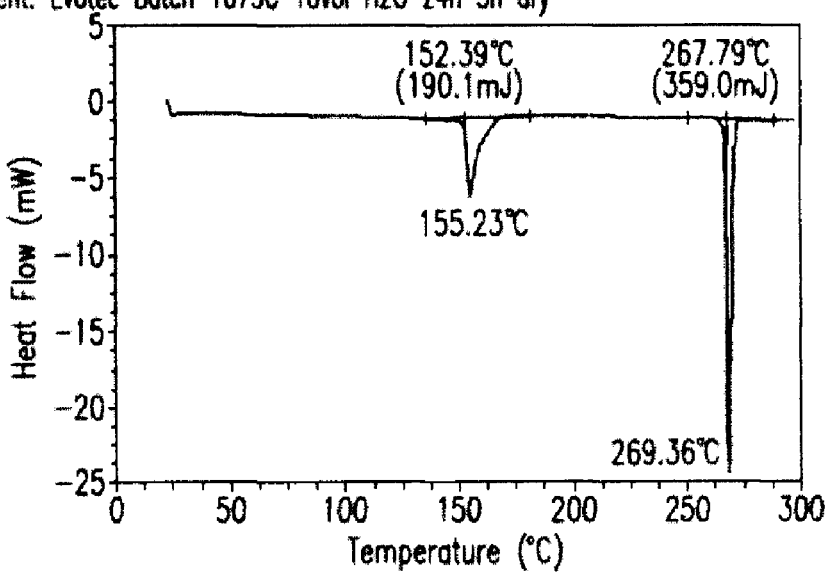
Figure 44:
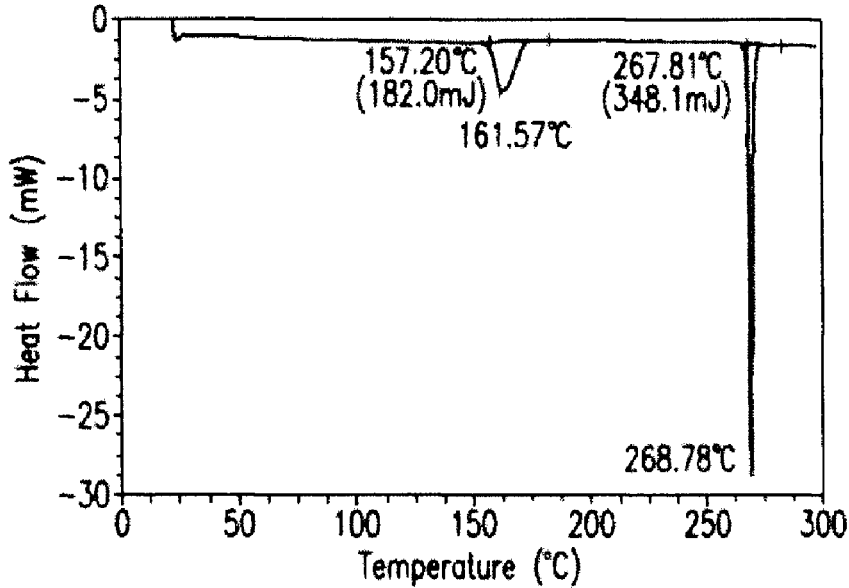
Figure 45:
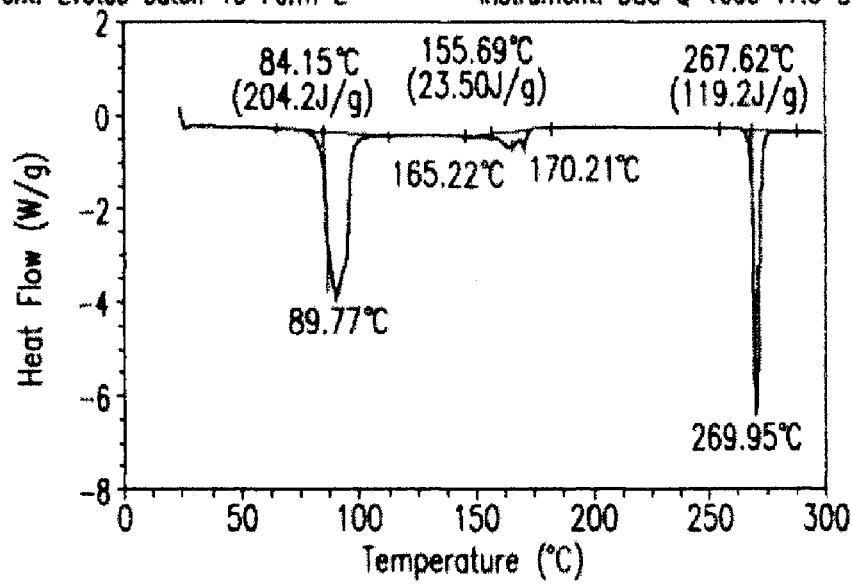
Figure 46:
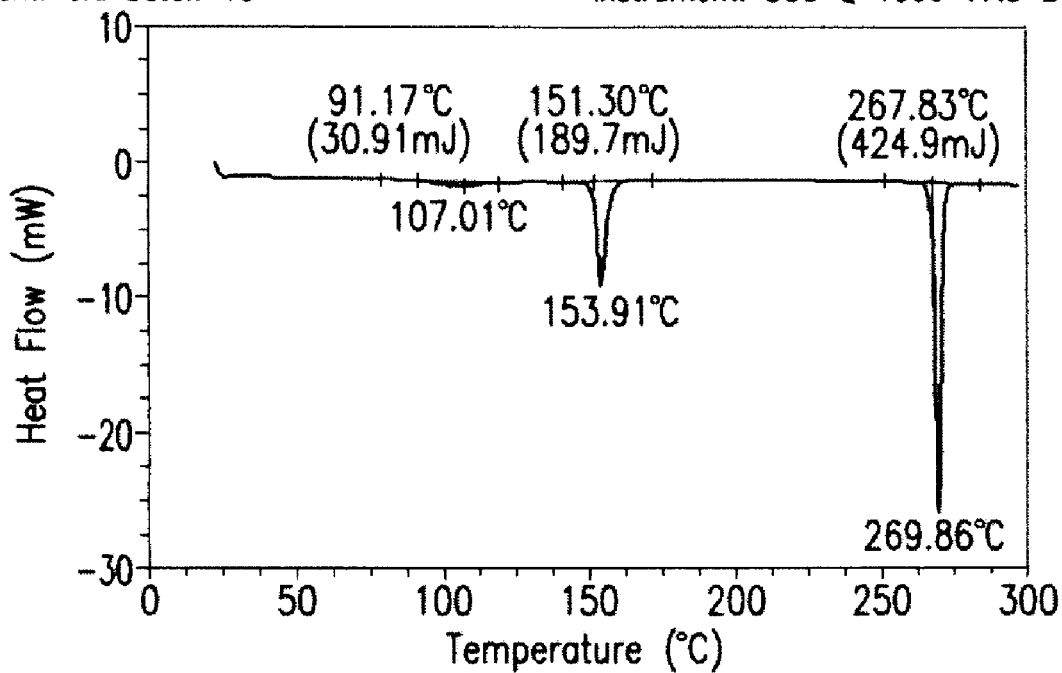

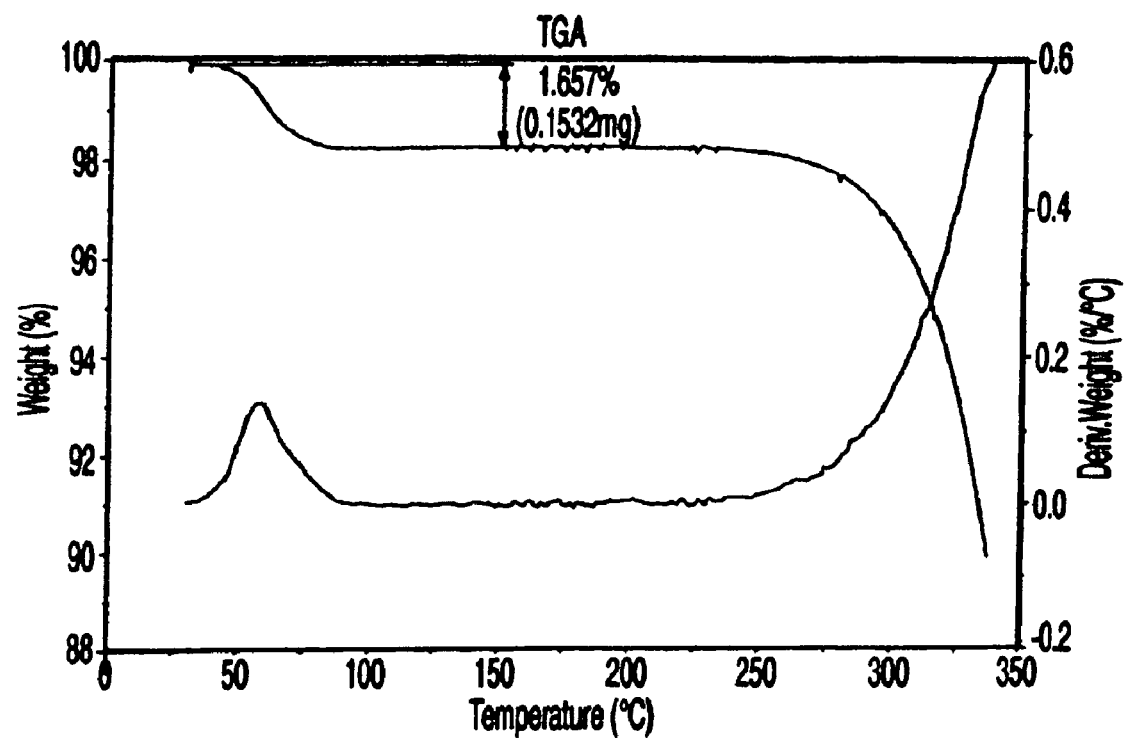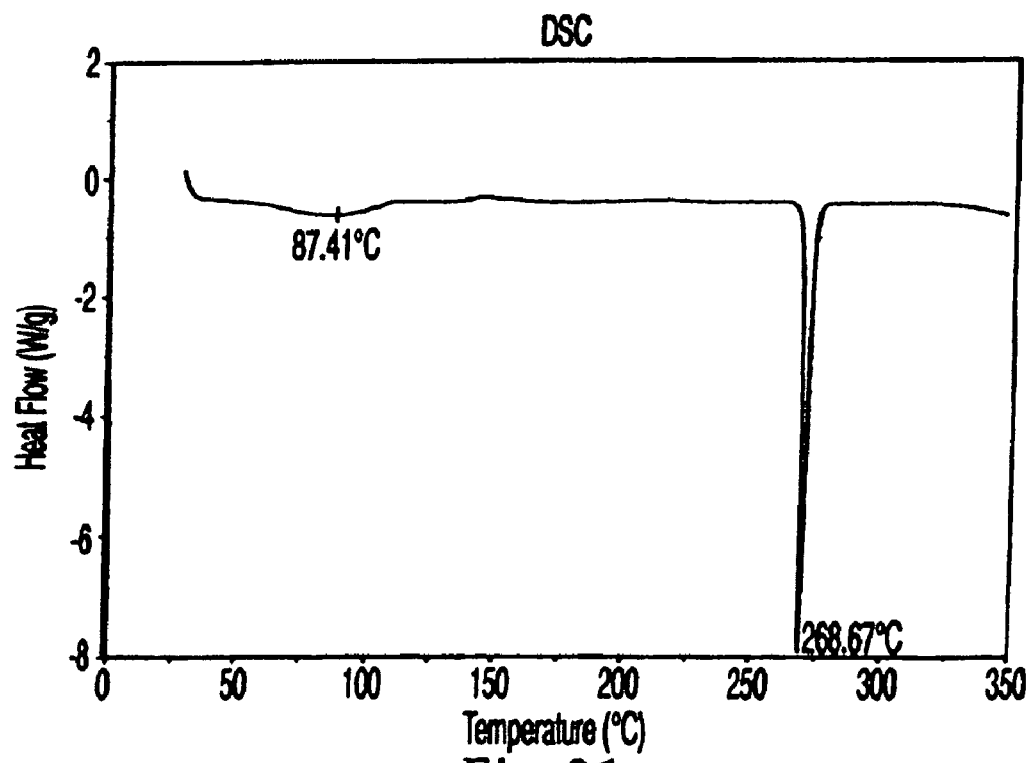
Fig. 31

POLYMORPHIC FORMS OF 3-(4-AMINO-1-OXO-1,3 DIHYDRO-ISOINDOL-2-YL)-PIPERIDINE-2,6-DIONE

This application is a divisional application of U.S. patent application Ser. No. 10/934,863, filed Sep. 3, 2004, now U.S. Pat. No. 7,465,800 presently pending, which claims the benefit of U.S. provisional application 60/499,723, filed Sep. 4, 2003, the contents of each of which are incorporated by reference herein in their entireties.

1. FIELD OF THE INVENTION

This invention relates to polymorphic forms of 3-(4-amino-1-oxo-1,3 dihydro-isoindol-2-yl)-piperidine-2,6-dione, compositions comprising the polymorphic forms, methods of making the polymorphic forms and methods of their use for the treatment of diseases and conditions including, but not limited to, inflammatory diseases, autoimmune diseases, and cancer.

2. BACKGROUND OF THE INVENTION

Many compounds can exist in different crystal forms, or polymorphs, which exhibit different physical, chemical, and spectroscopic properties. For example, certain polymorphs of a compound may be more readily soluble in particular solvents, may flow more readily, or may compress more easily than others. See, e.g., P. DiMartino, et al., *J. Thermal Anal.*, 48:447-458 (1997). In the case of drugs, certain solid forms may be more bioavailable than others, while others may be more stable under certain manufacturing, storage, and biological conditions. This is particularly important from a regulatory standpoint, since drugs are approved by agencies such as the U.S. Food and Drug Administration only if they meet exacting purity and characterization standards. Indeed, the regulatory approval of one polymorph of a compound, which exhibits certain solubility and physico-chemical (including spectroscopic) properties, typically does not imply the ready approval of other polymorphs of that same compound.

Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. *Modern Drug Discoveries*, 2000, 53. Therefore, the discovery of new polymorphs of a drug can provide a variety of advantages.

U.S. Pat. Nos. 5,635,517 and 6,281,230, both to Muller et al., disclose 3-(4-amino-1-oxo-1,3 dihydro-isoindol-2-yl)-piperidine-2,6-dione, which is useful in treating and preventing a wide range of diseases and conditions including, but not limited to, inflammatory diseases, autoimmune diseases, and cancer. New polymorphic forms of 3-(4 amino-1-oxo-1,3 dihydro-isoindol-2-yl)-piperidine-2,6-dione can further the development of formulations for the treatment of these chronic illnesses, and may yield numerous formulation, manufacturing and therapeutic benefits.

3. SUMMARY OF THE INVENTION

This invention encompasses polymorphs of 3-(4-amino-1-oxo-1,3 dihydro-isoindol-2-yl)-piperidine-2,6-dione. In certain aspects, the invention provides polymorphs of the compound identified herein as forms A, B, C, D, E, F, G, and H. The invention also encompasses mixtures of these forms. In further embodiments, this invention provides methods of making, isolating and characterizing the polymorphs.

This invention also provides pharmaceutical compositions and single unit dosage forms comprising a polymorph of 3-(4-amino-1-oxo-1,3 dihydro-isoindol-2-yl)-piperidine-2,6-dione. The invention further provides methods for the treatment or prevention of a variety of diseases and disorders, which comprise administering to a patient in need of such treatment or prevention a therapeutically effective amount of a polymorph of 3-(4-amino-1-oxo-1,3 dihydro-isoindol-2-yl)-piperidine-2,6-dione.

4. BRIEF DESCRIPTION OF THE DRAWINGS

Figure 2:
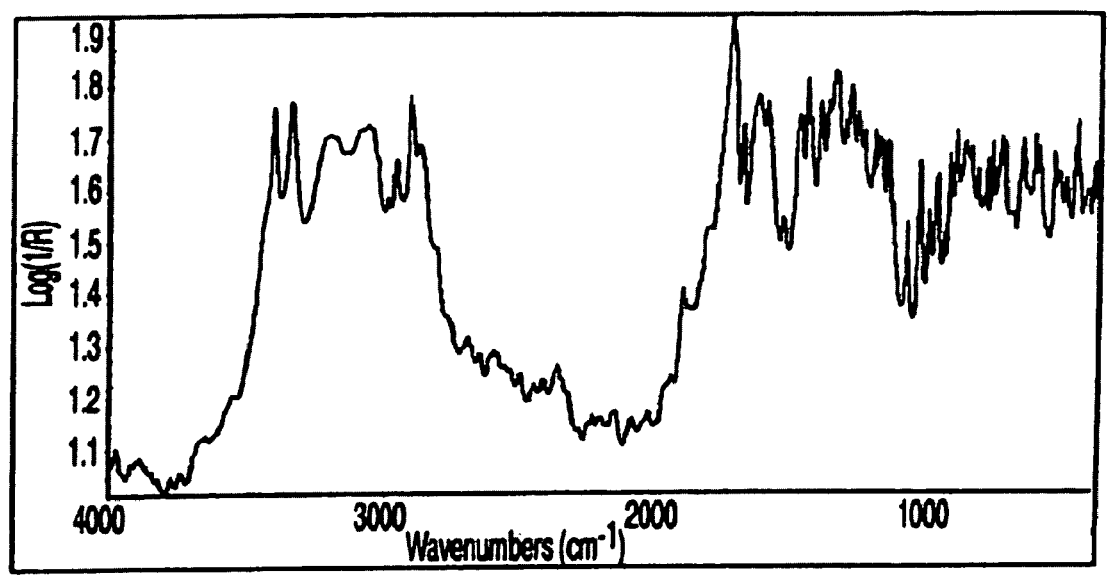
Figure 3:
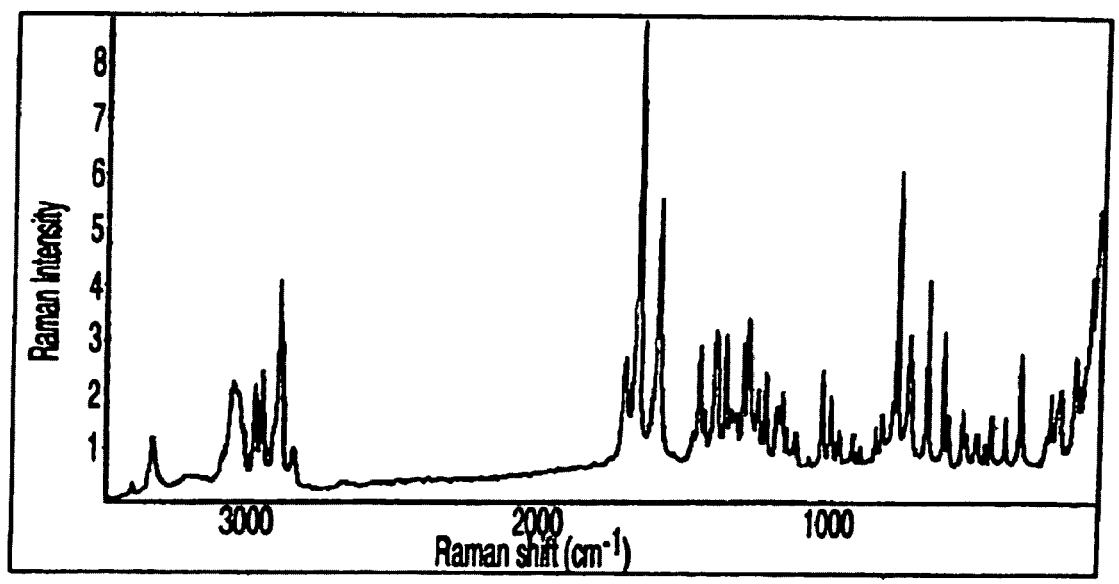
Figure 4:
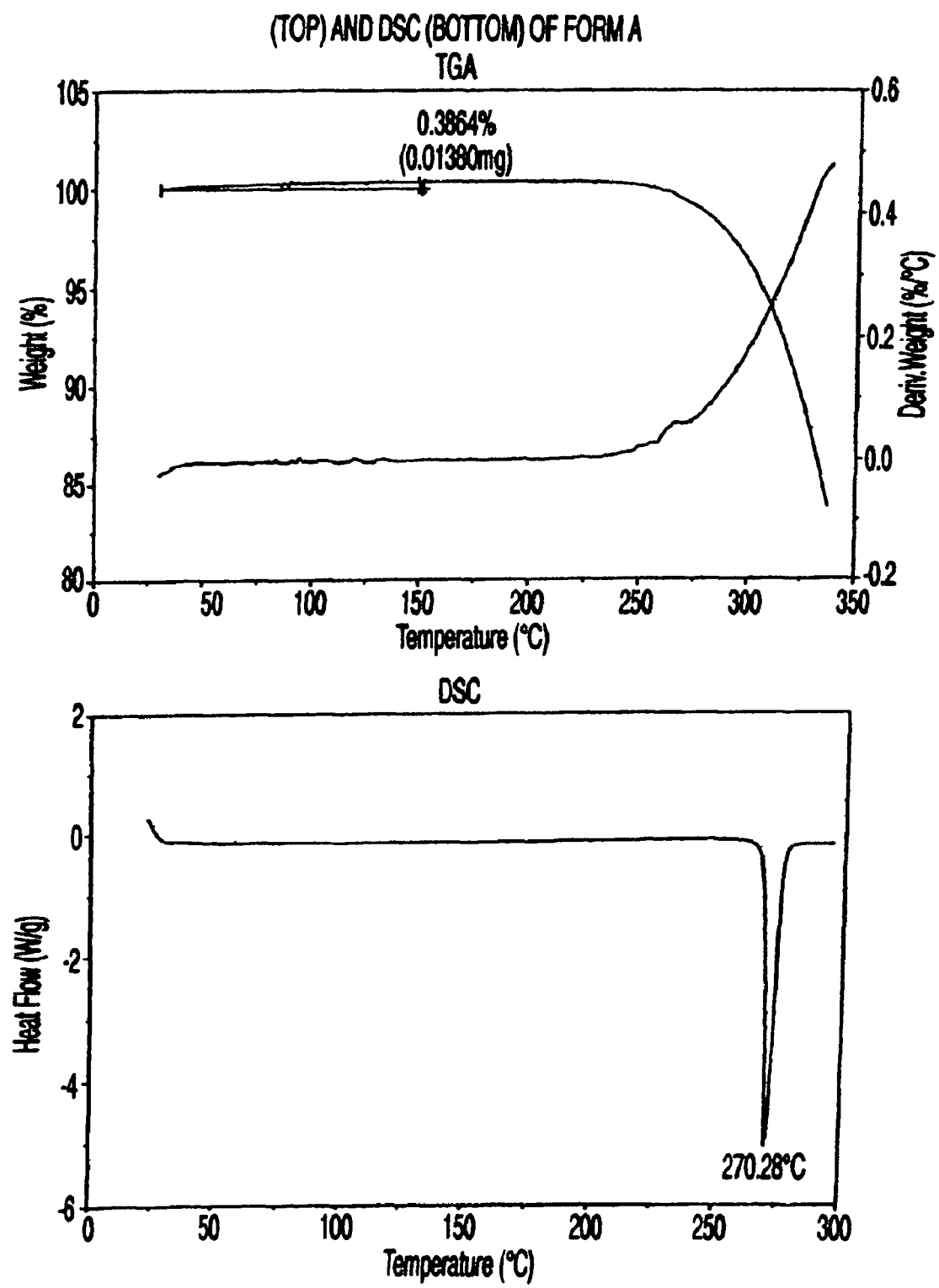
Figure 5:
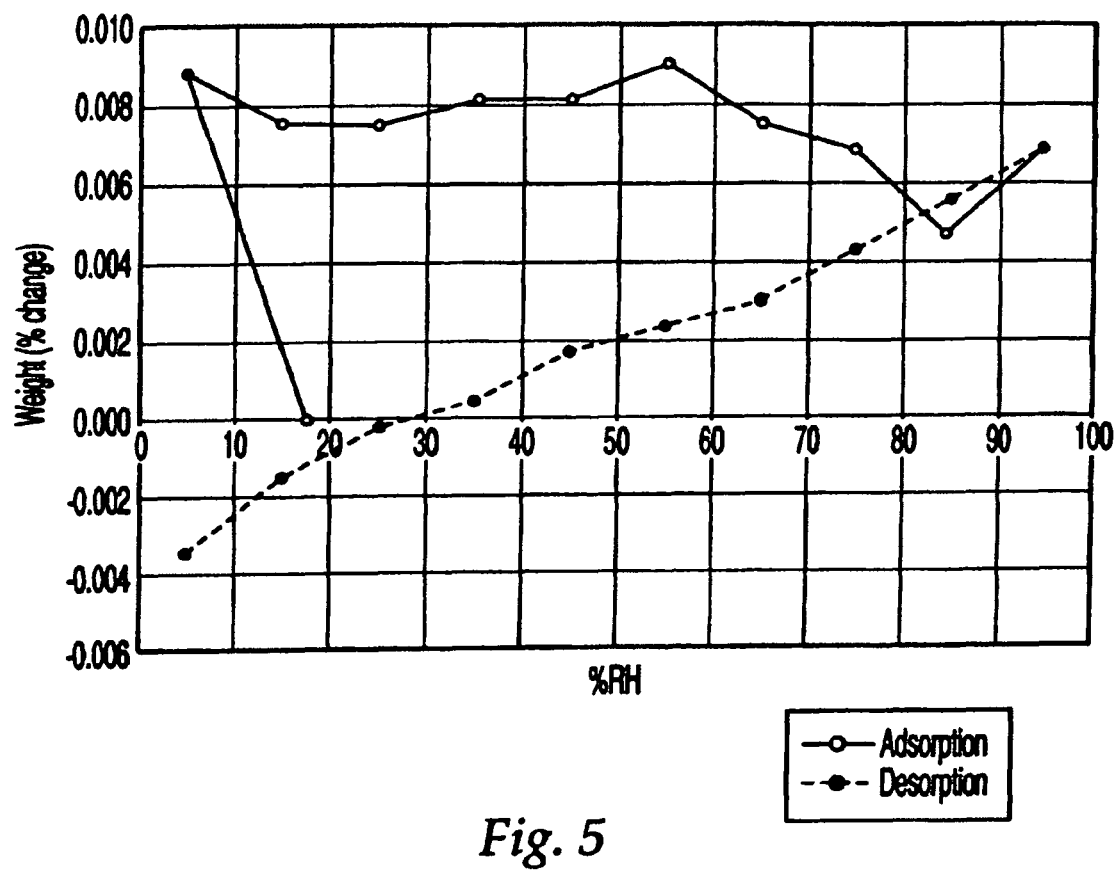
Figure 6:
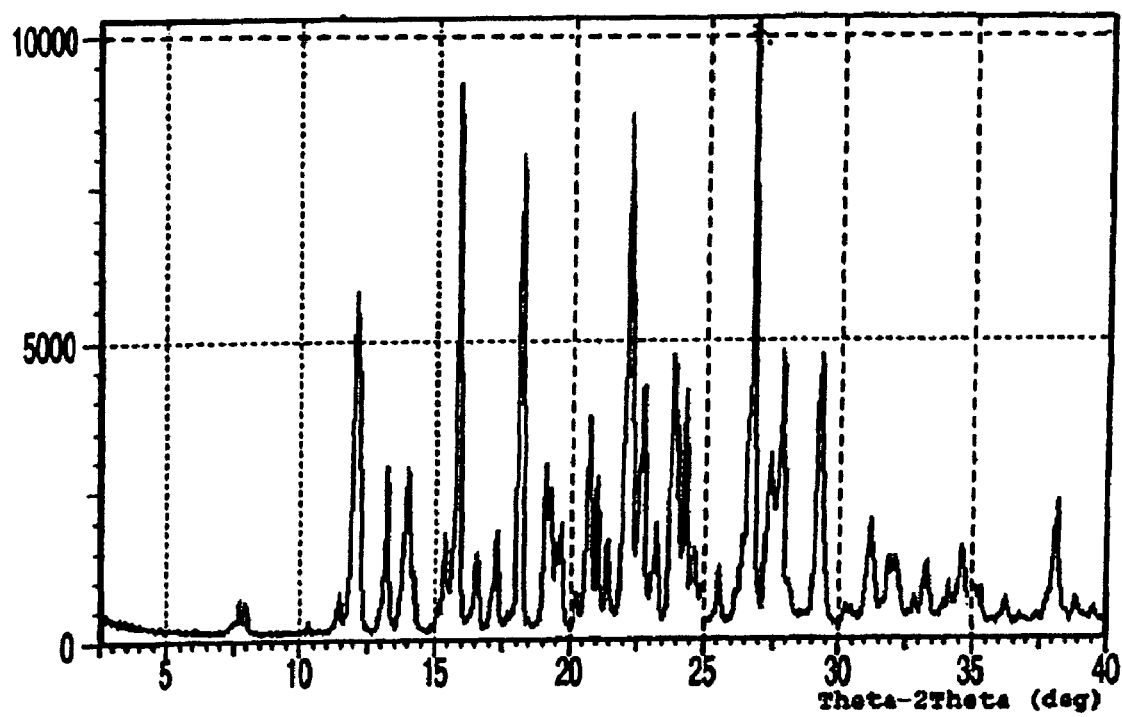
Figure 7:
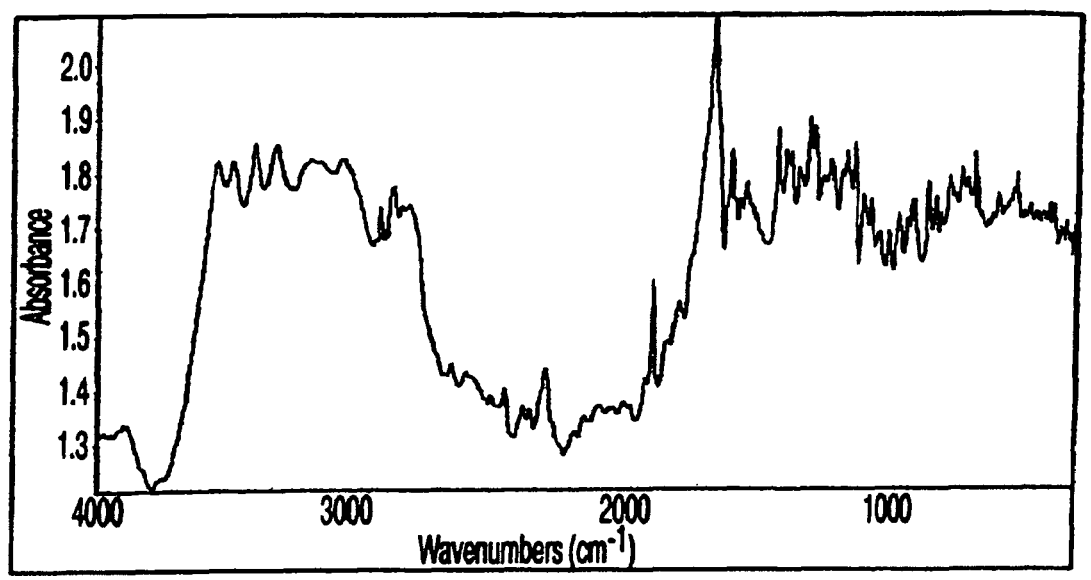
Figure 8:
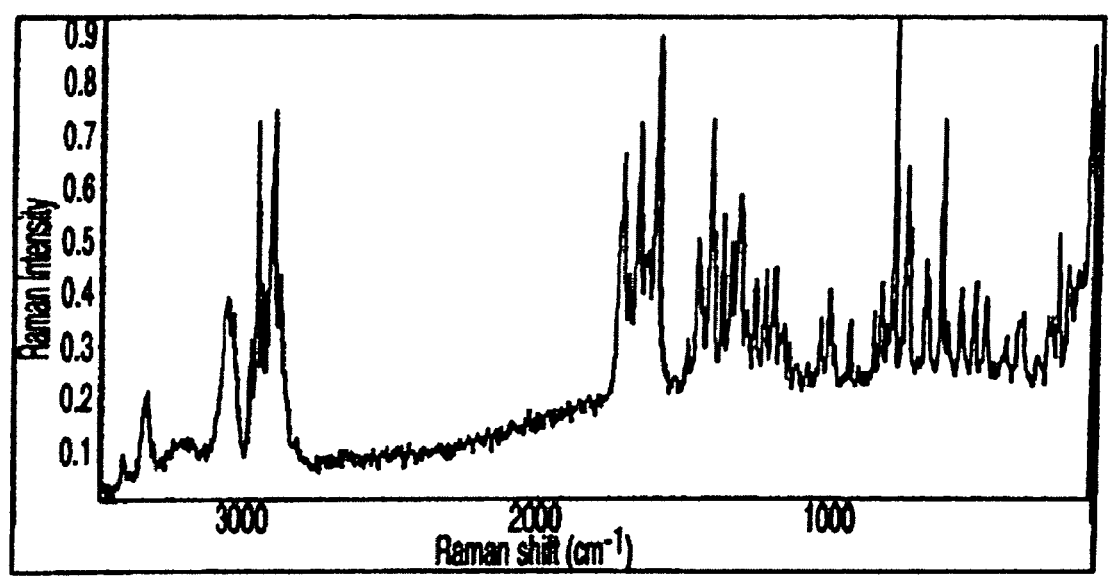
Figure 9:
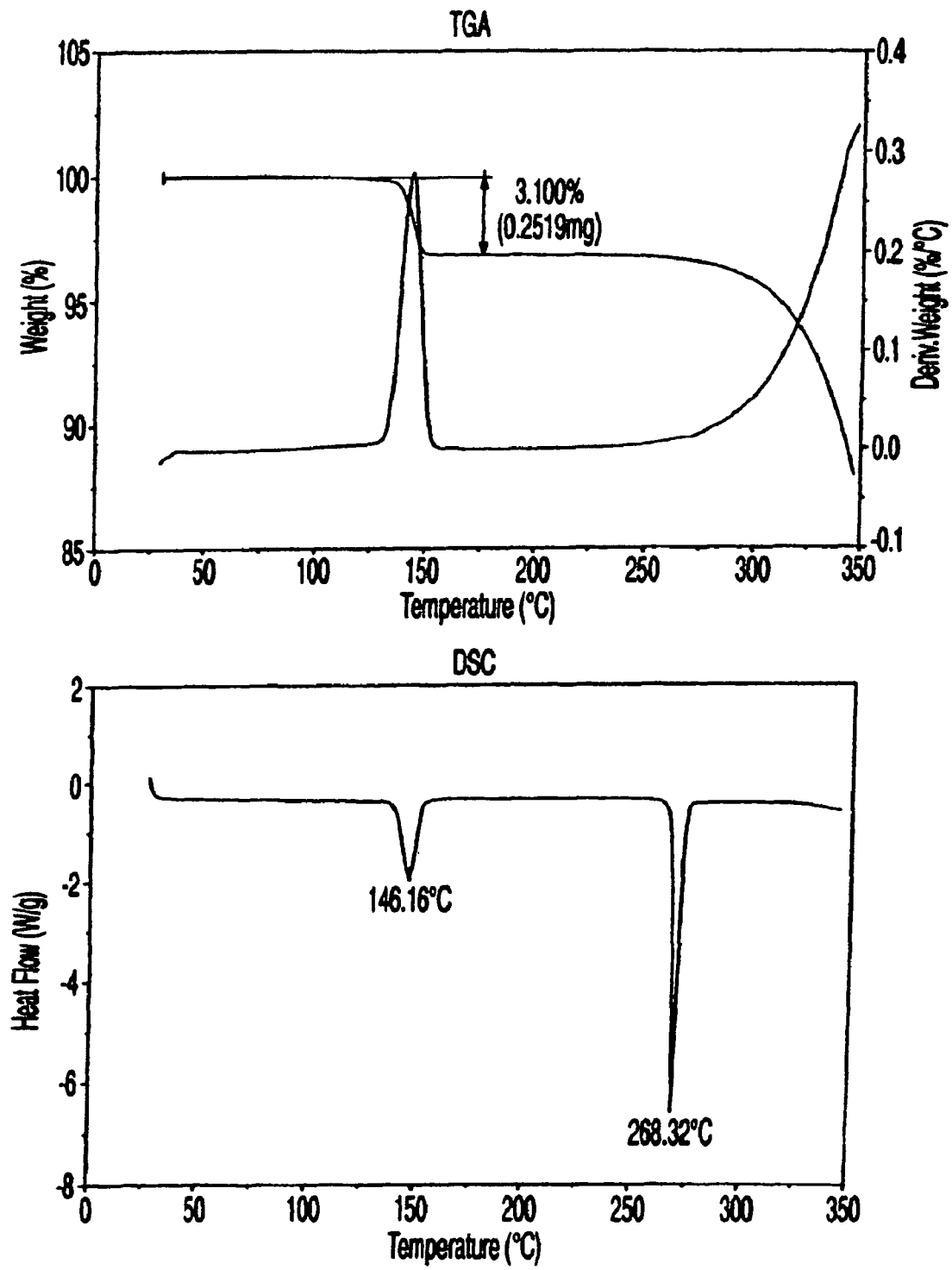
Figure 10:
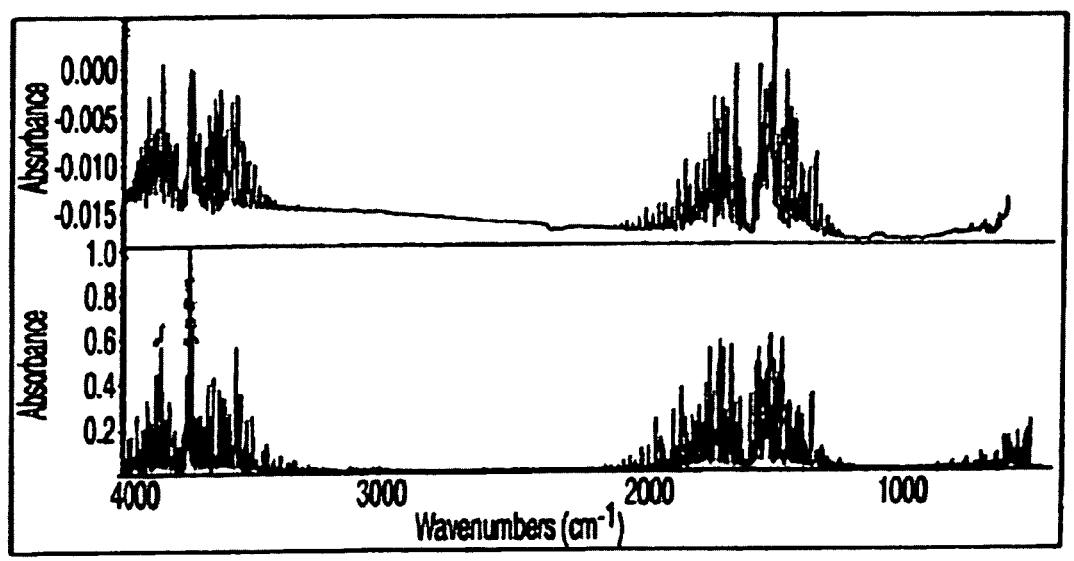
Figure 11:
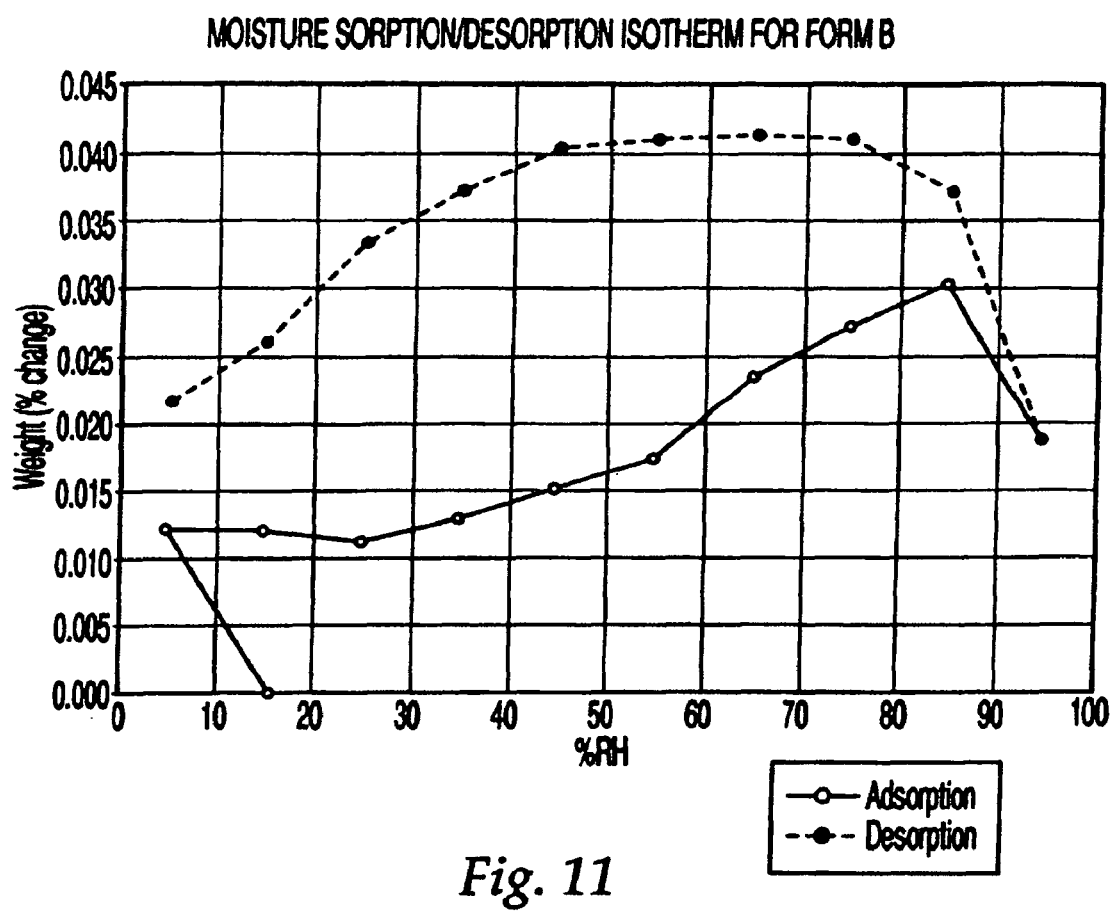
Figure 12:
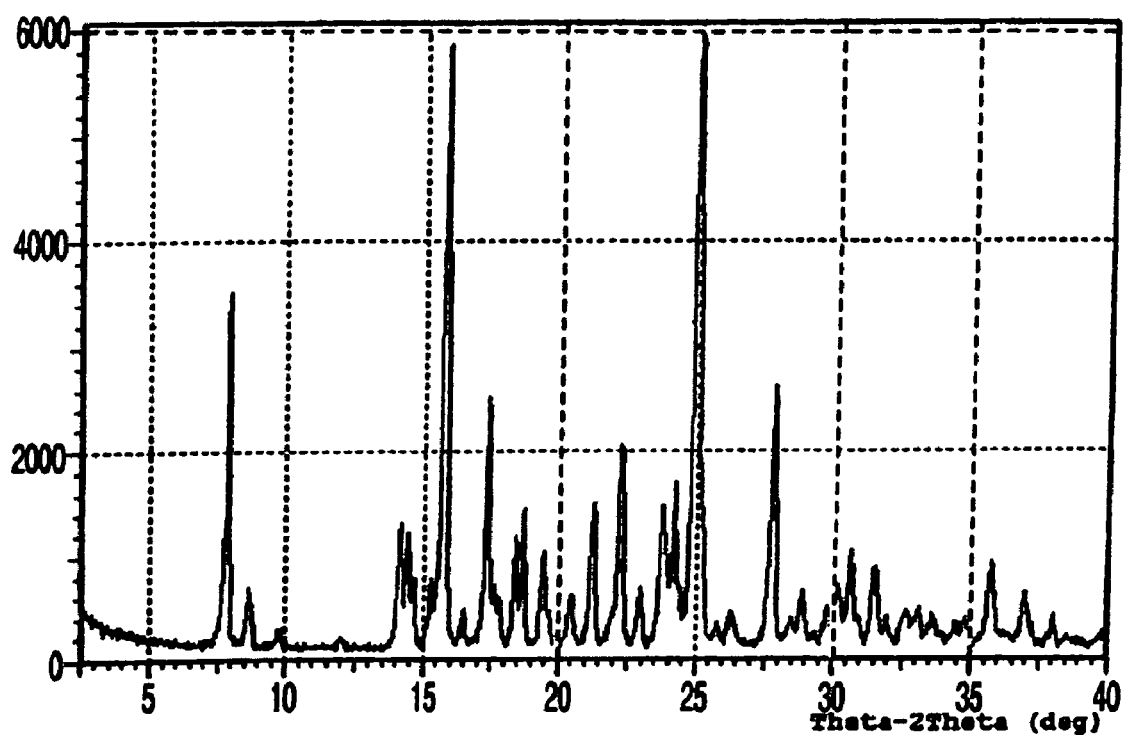
Figure 13:
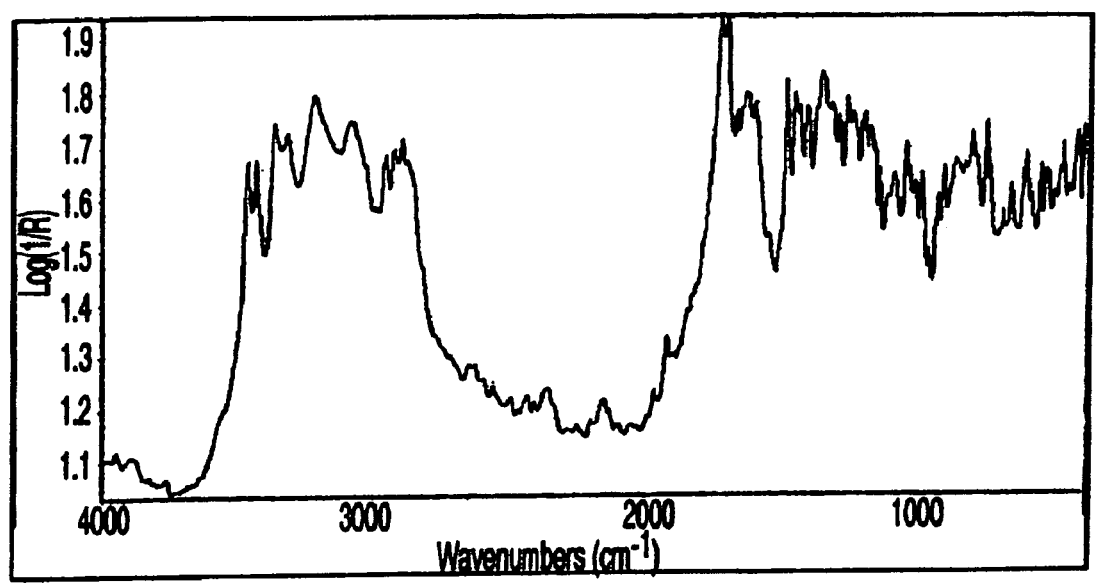
Figure 14:
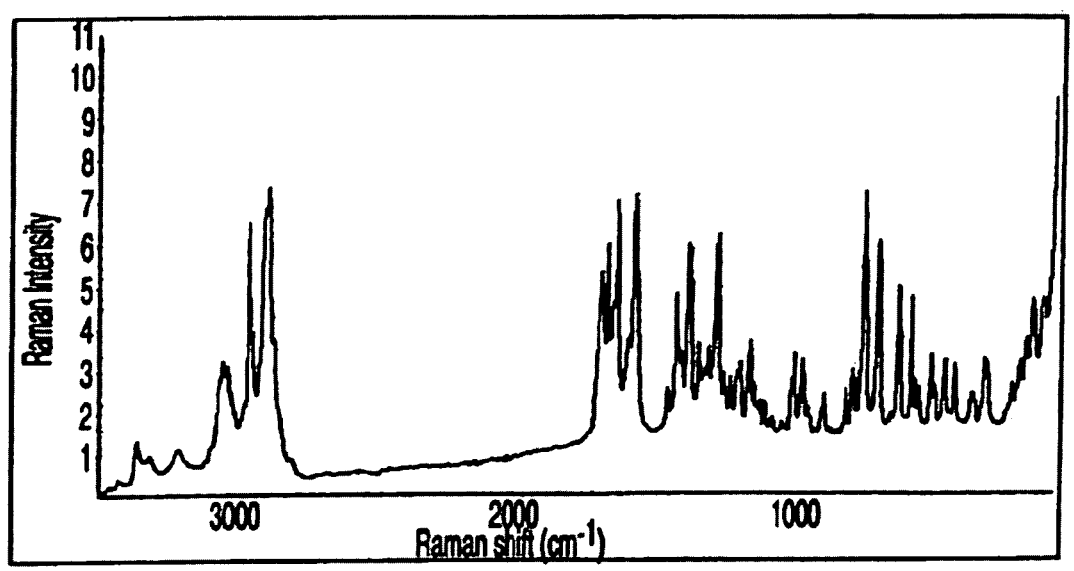
Figure 15:
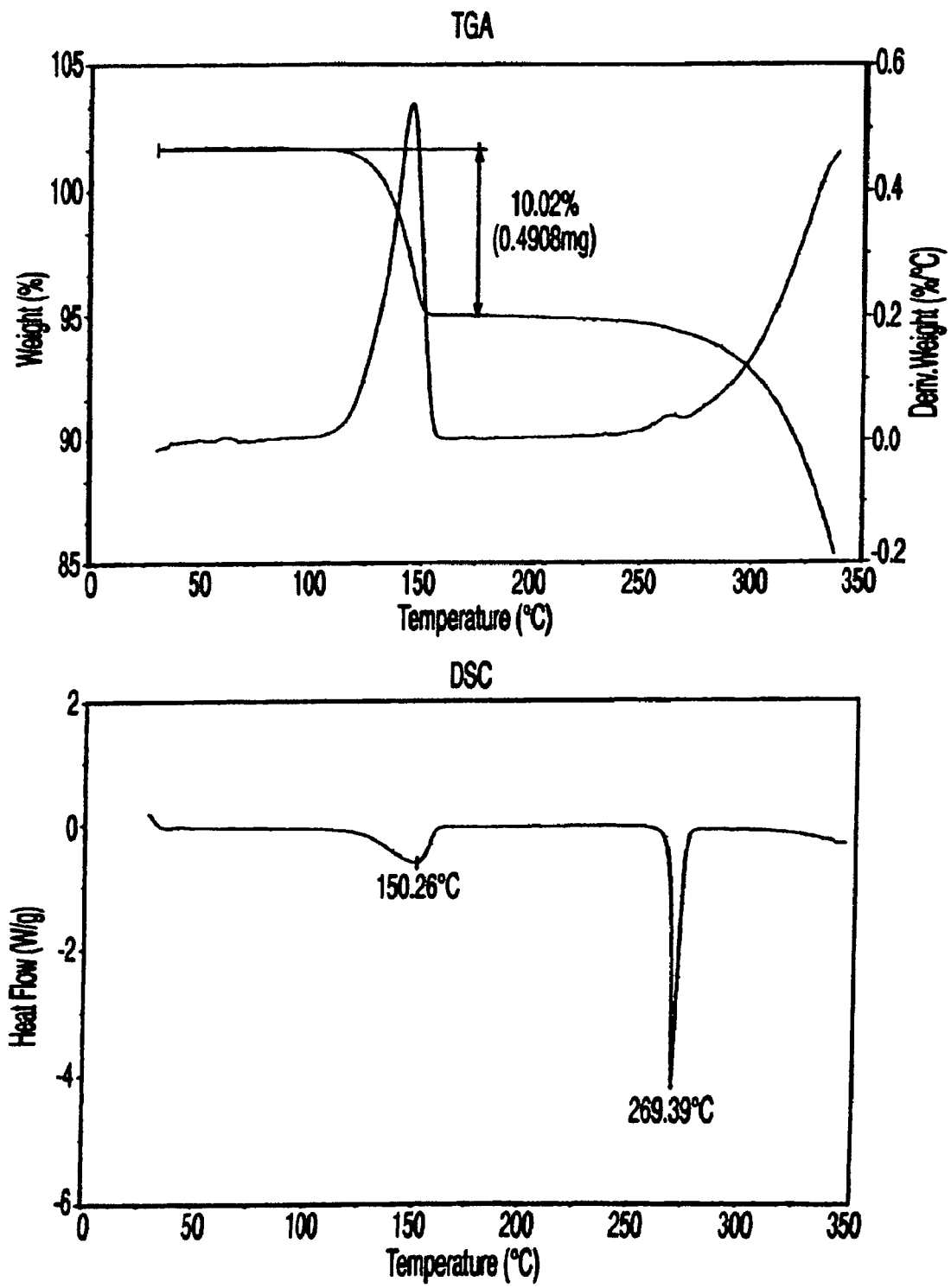
Figure 16:
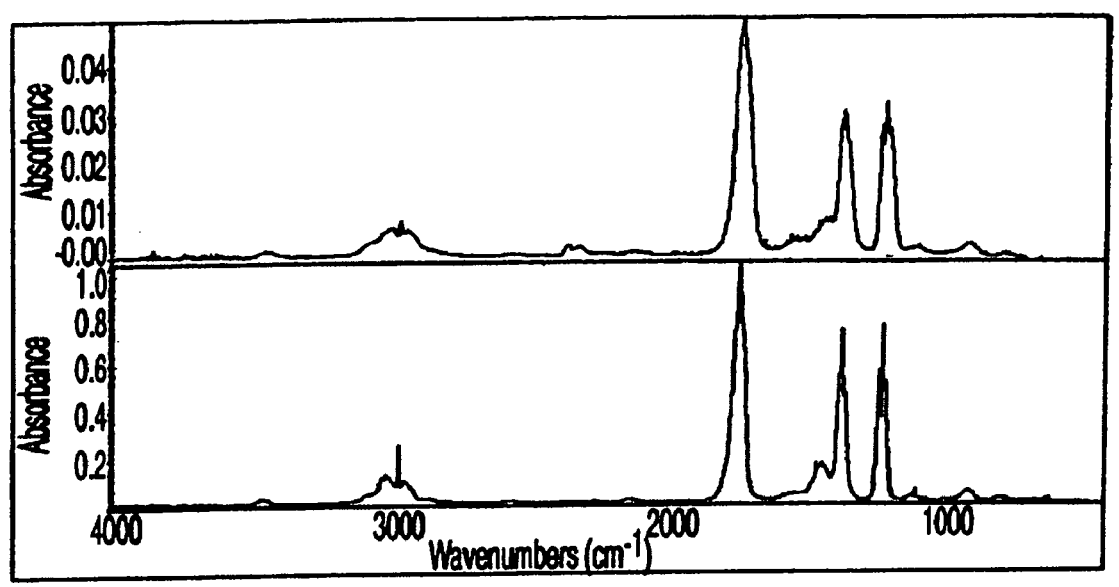
Figure 17:
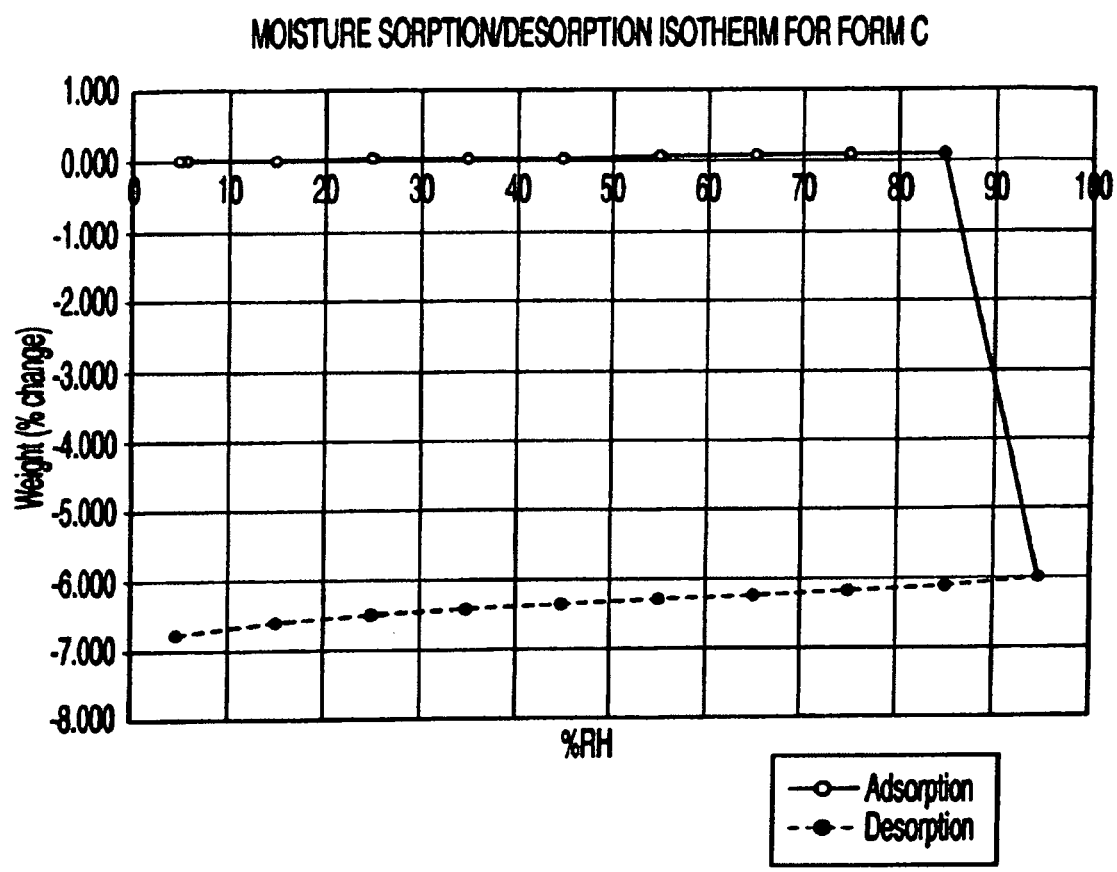
Figure 18:
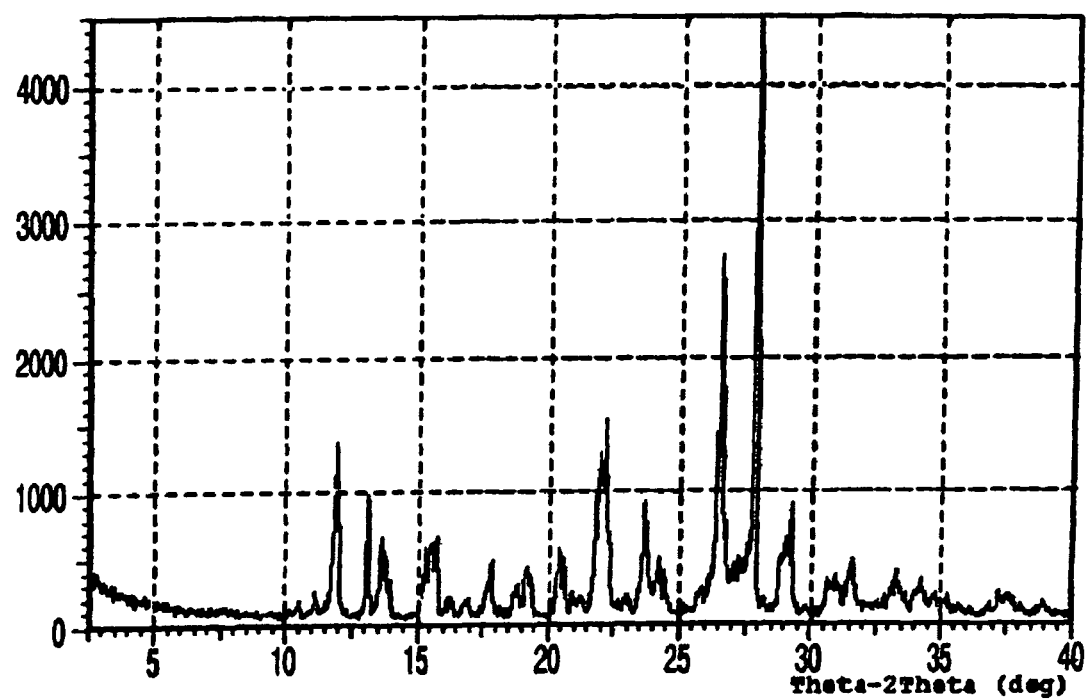
Figure 19:
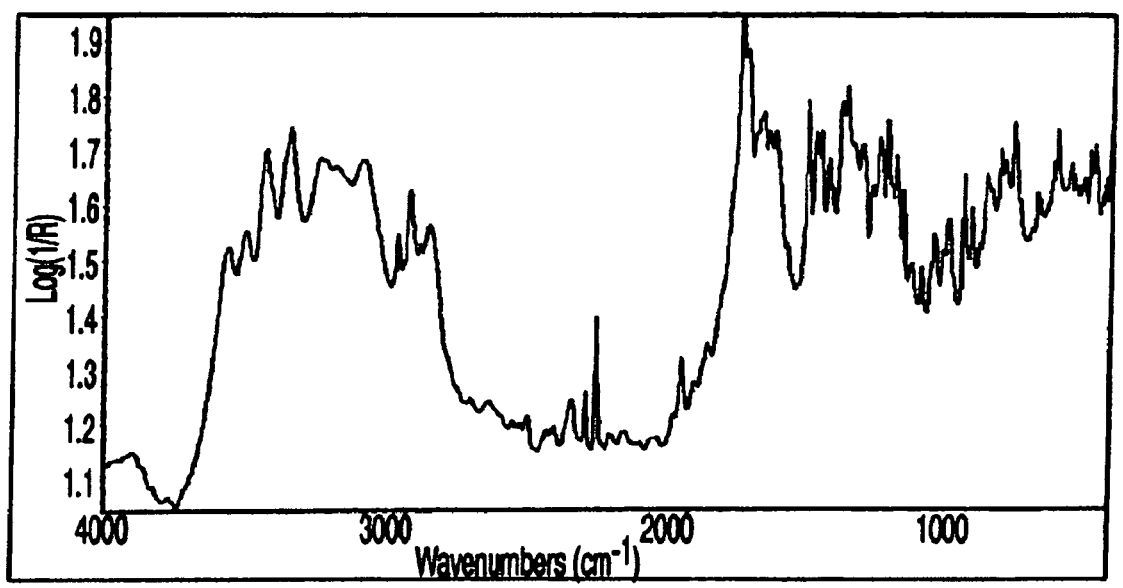
Figure 20:
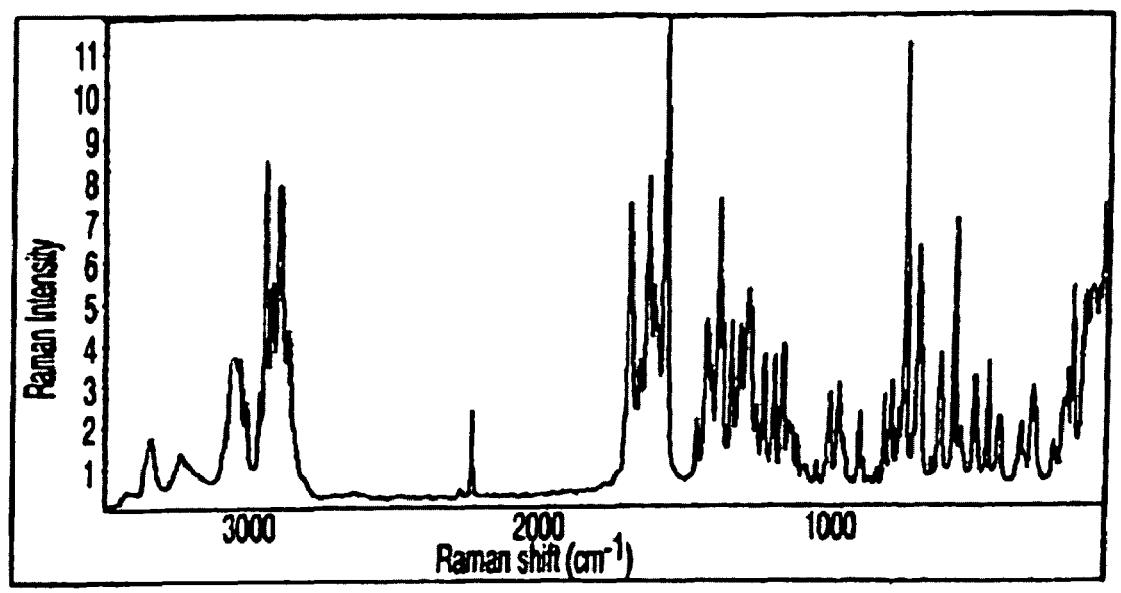
Figure 21:
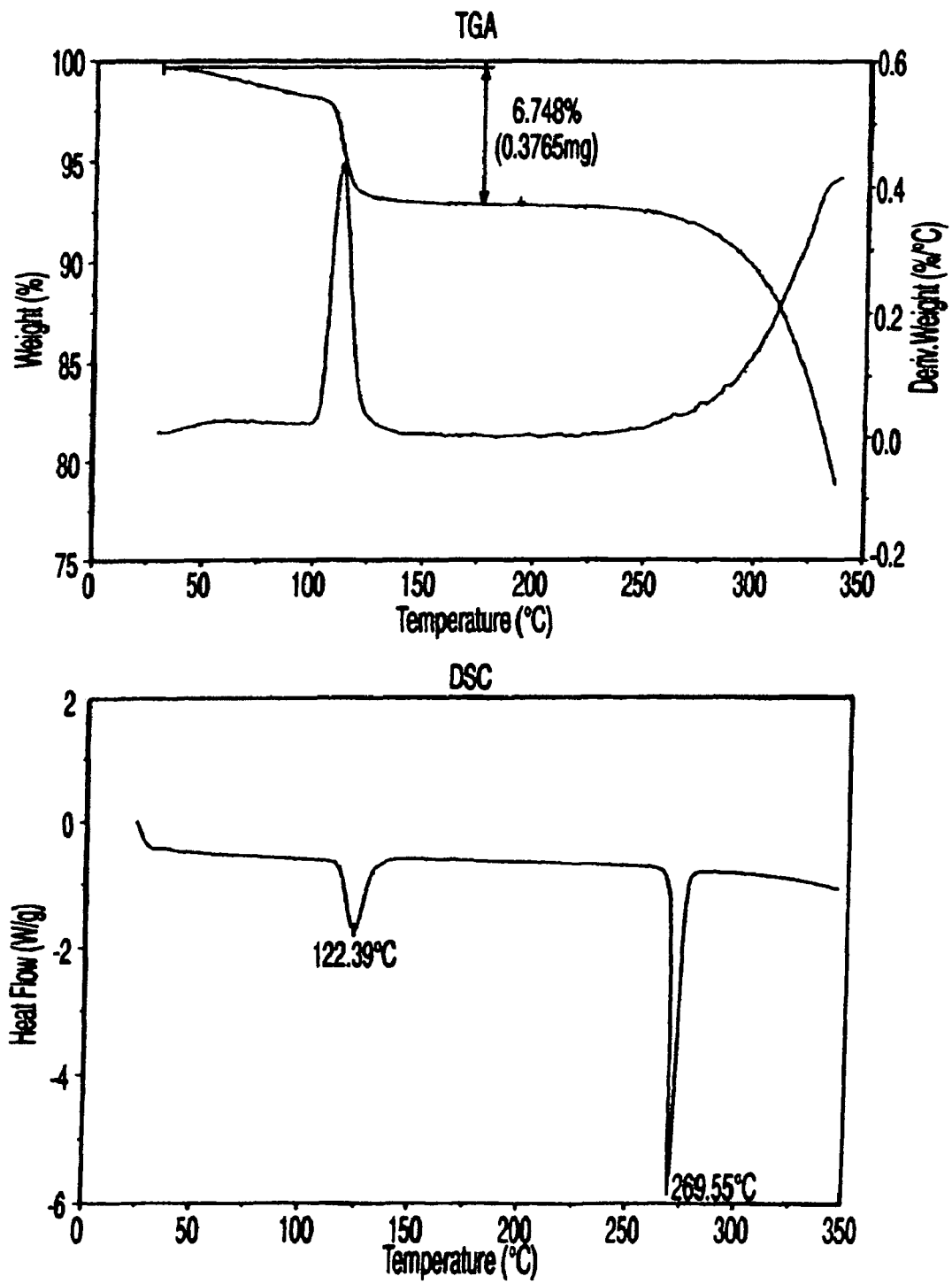
Figure 22:
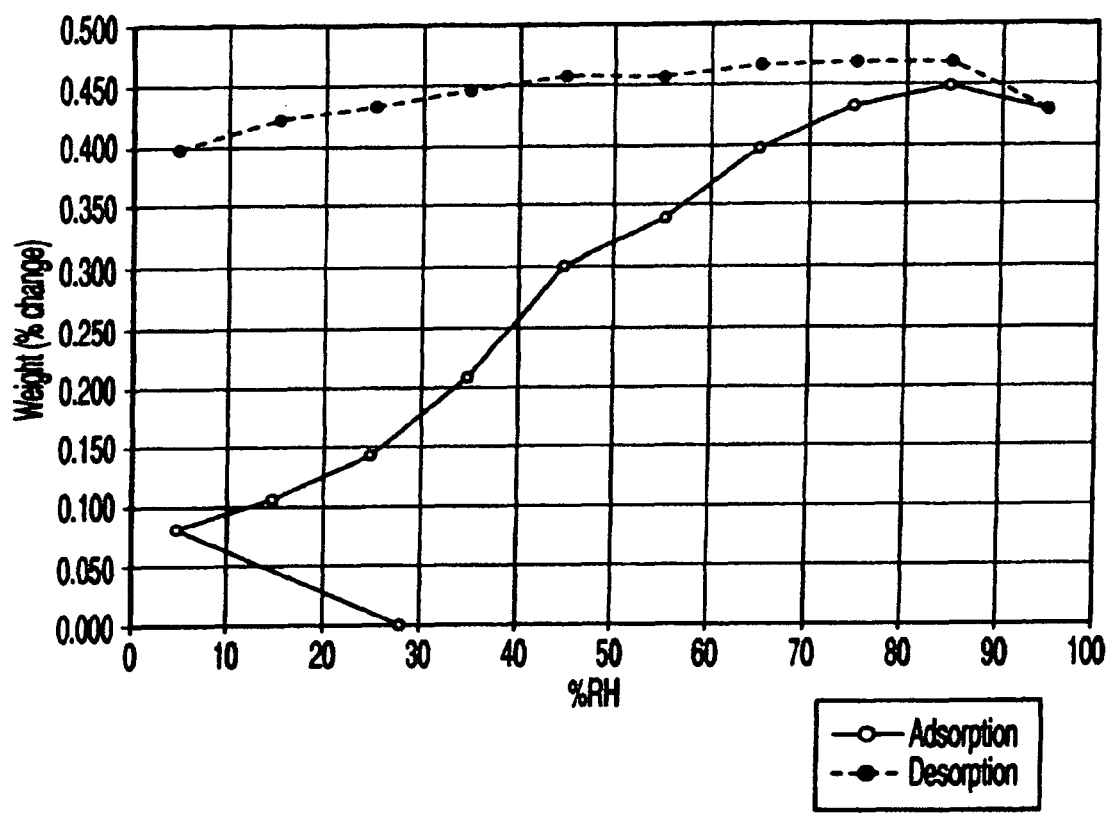
Figure 23:
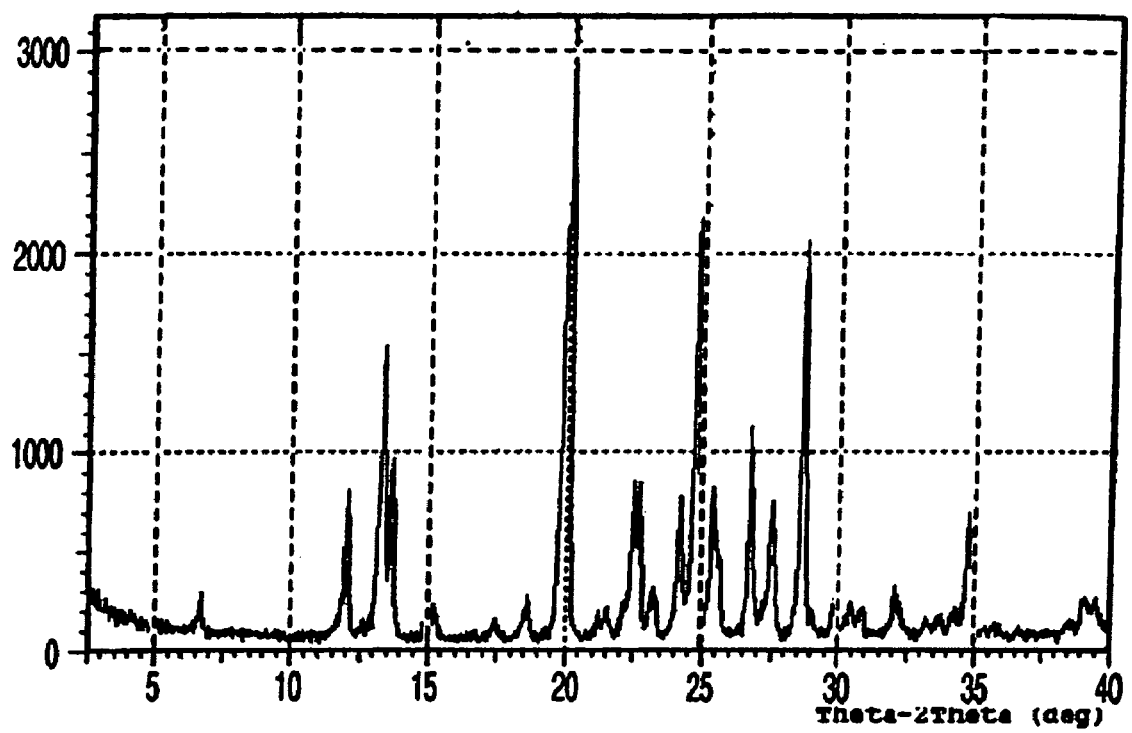
Figure 24:
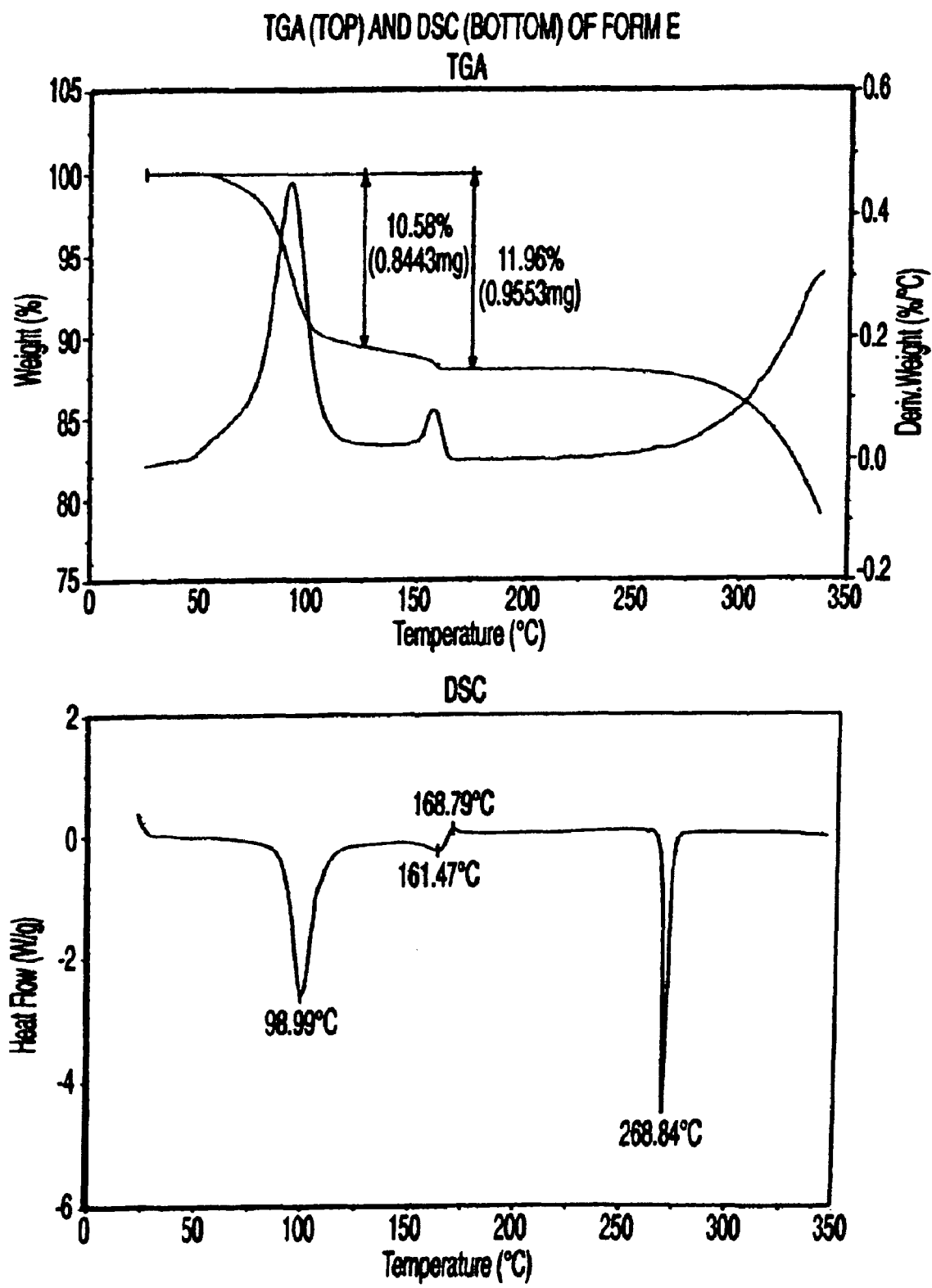
Figure 25:
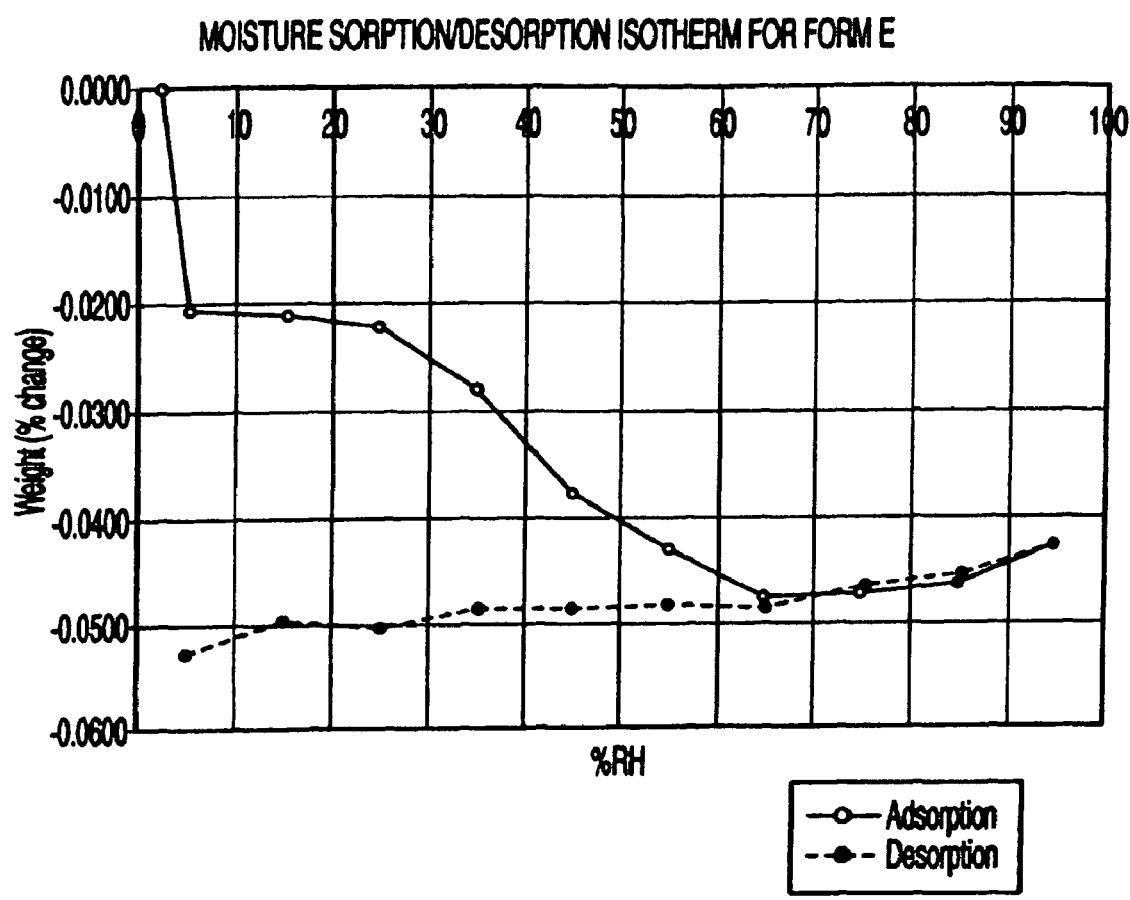
Figure 26:
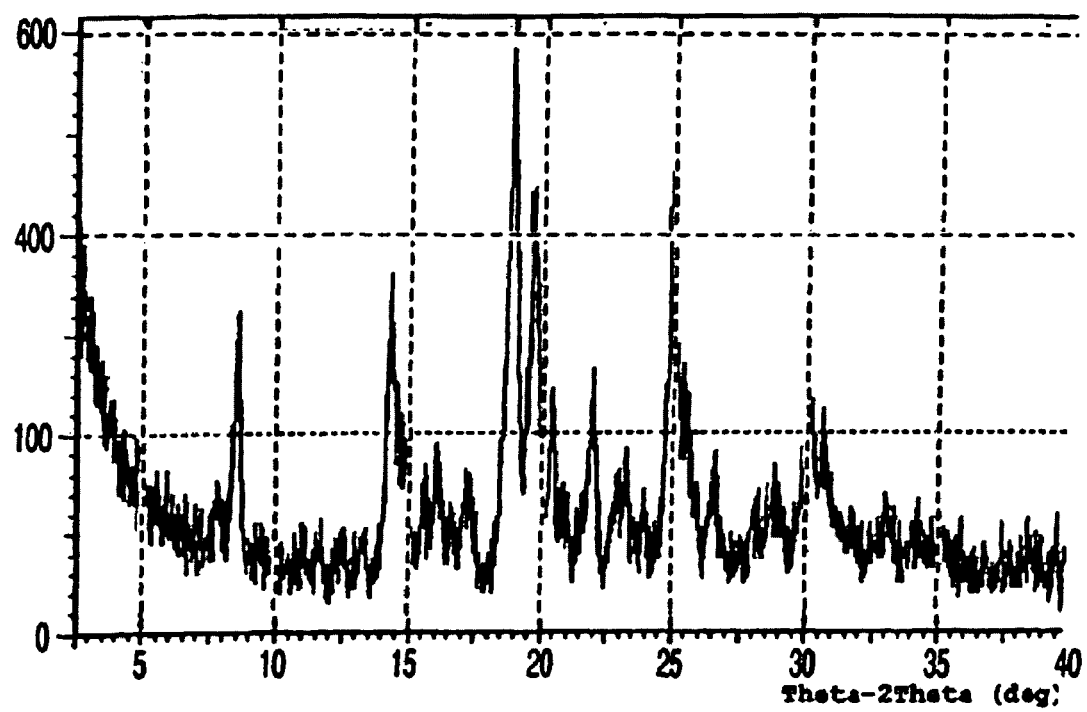
Figure 27:
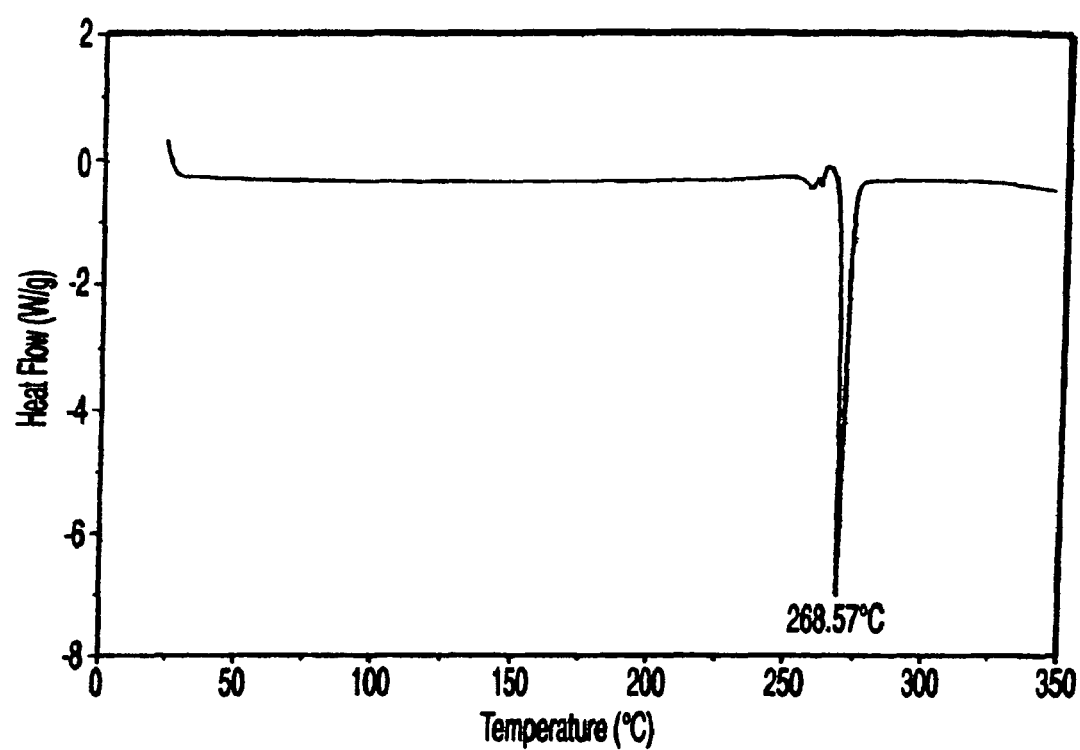
Figure 28:
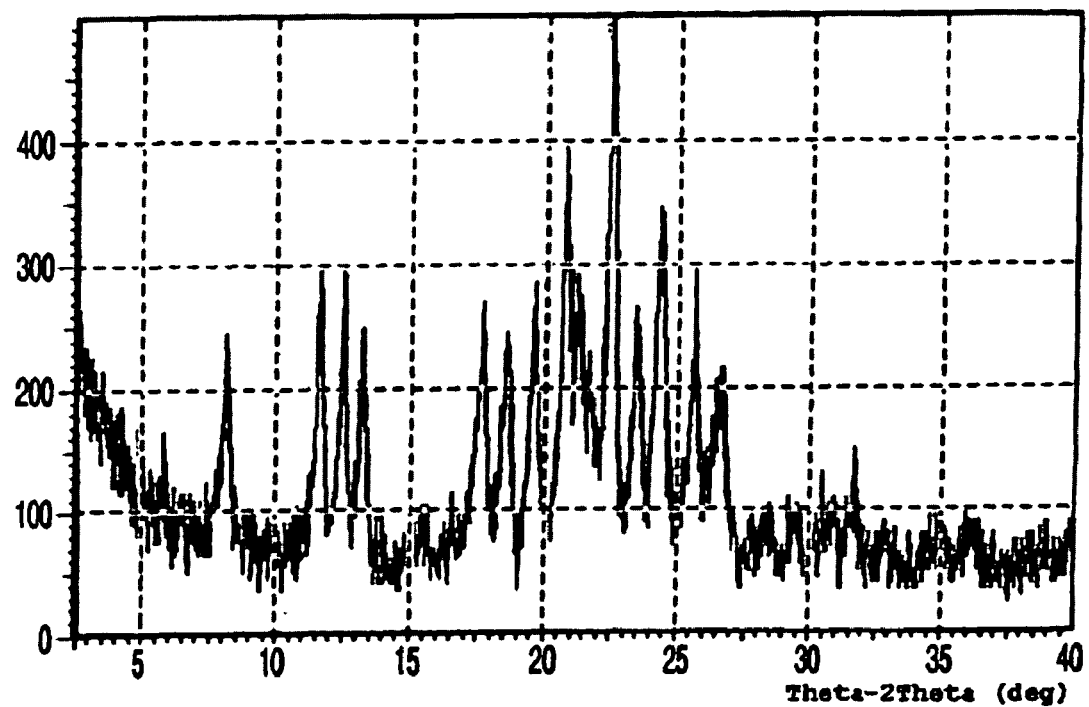
Figure 29:
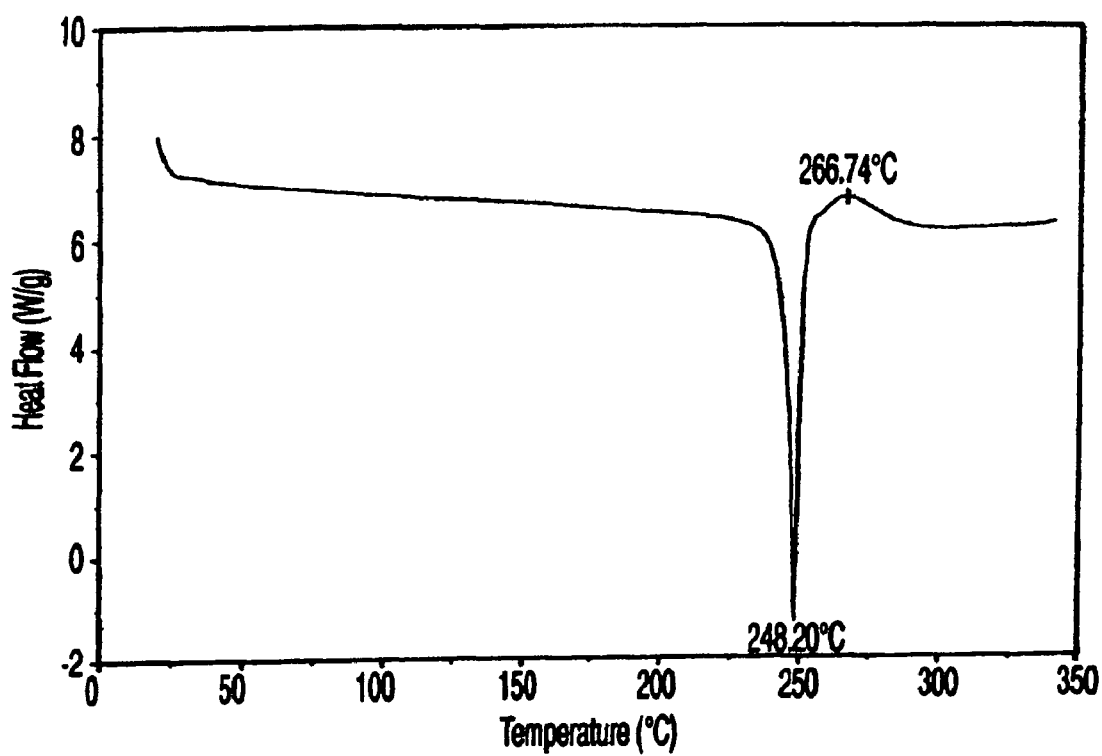
Figure 30:
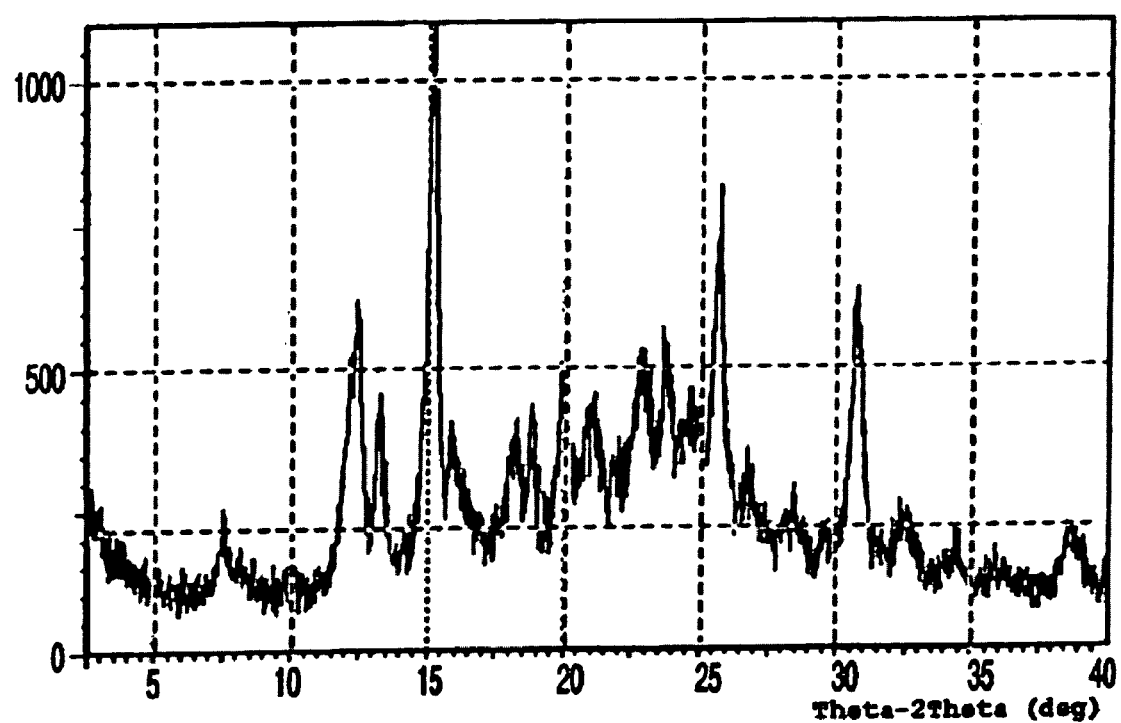
Figure 32:
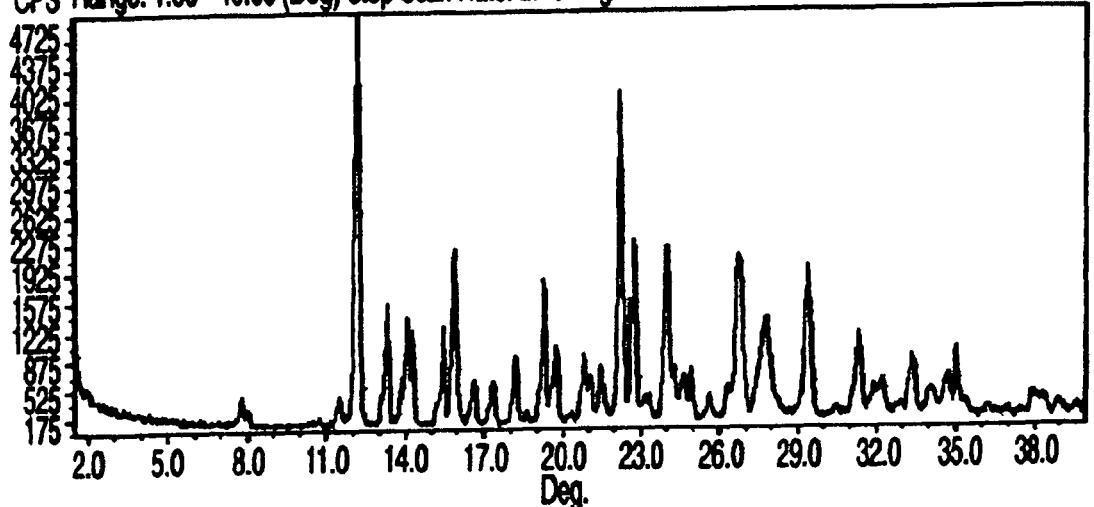
Figure 33:
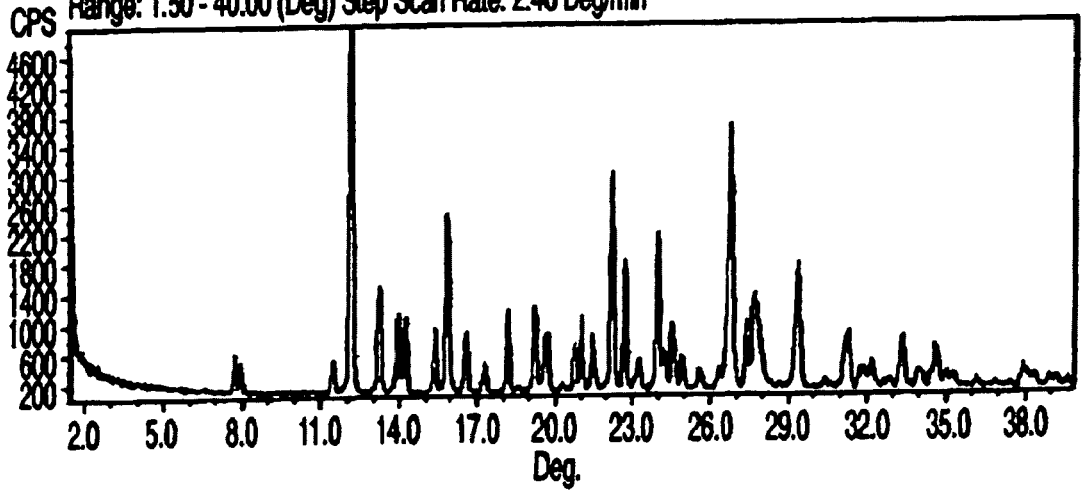
Figure 34:
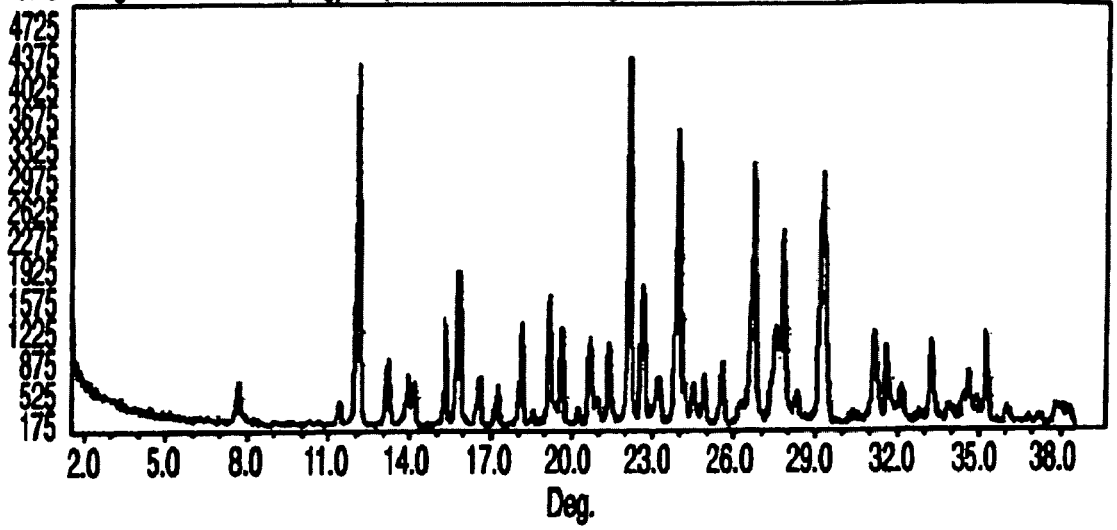
Figure 35:
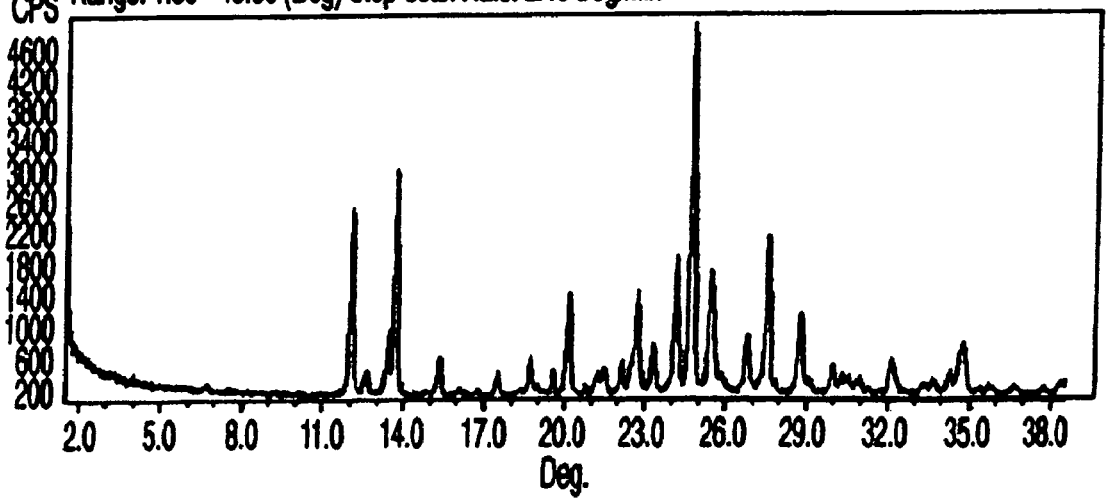
Figure 36:
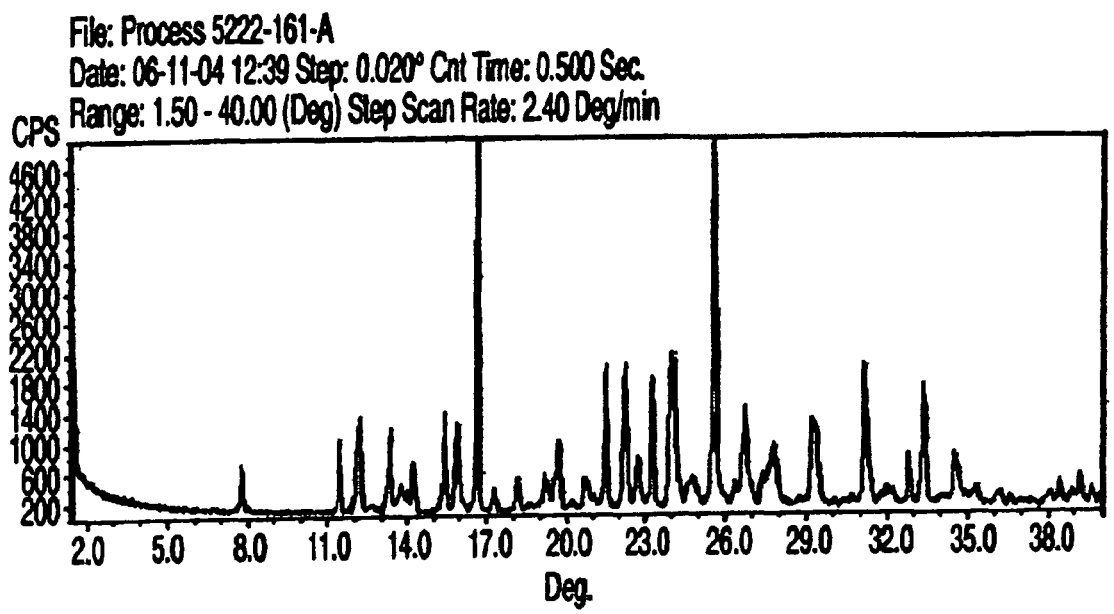
Figure 37:
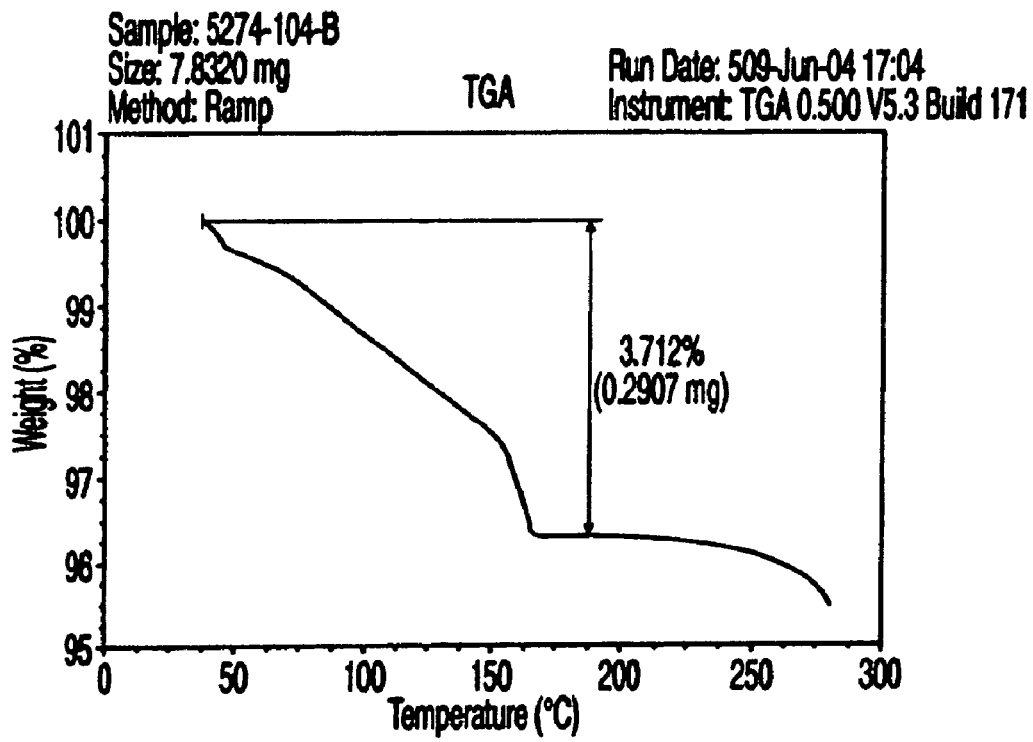
Figure 38:
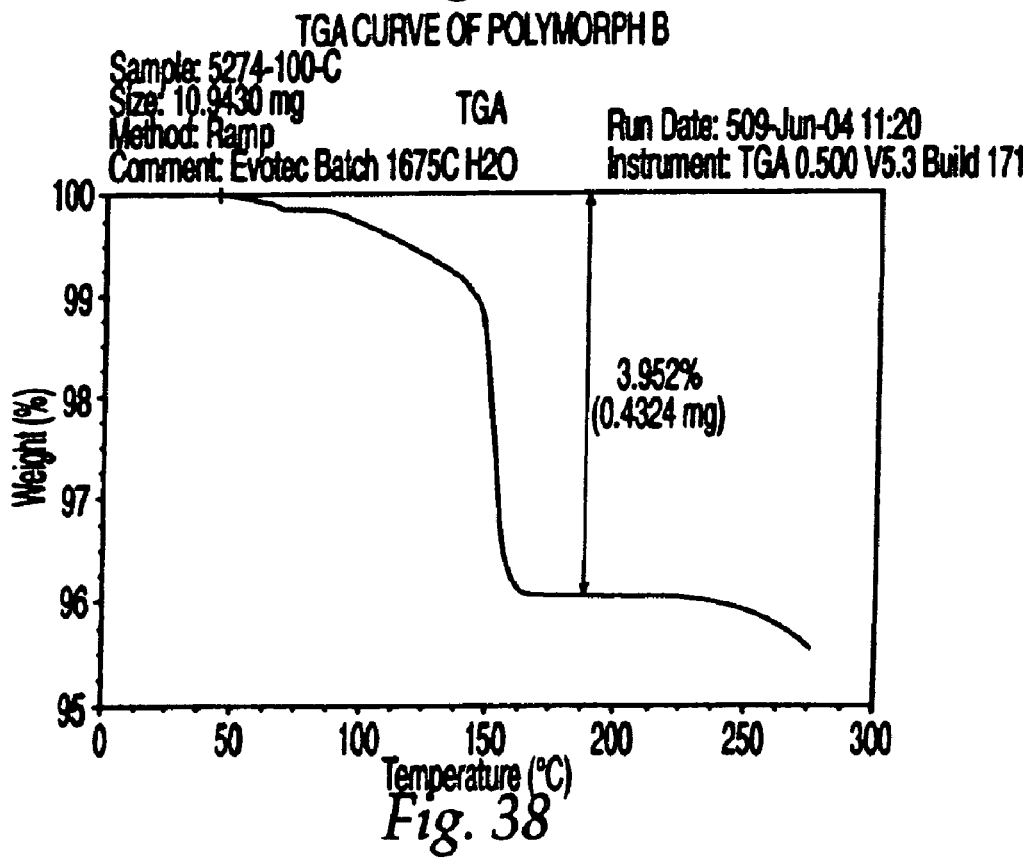
Figure 39:
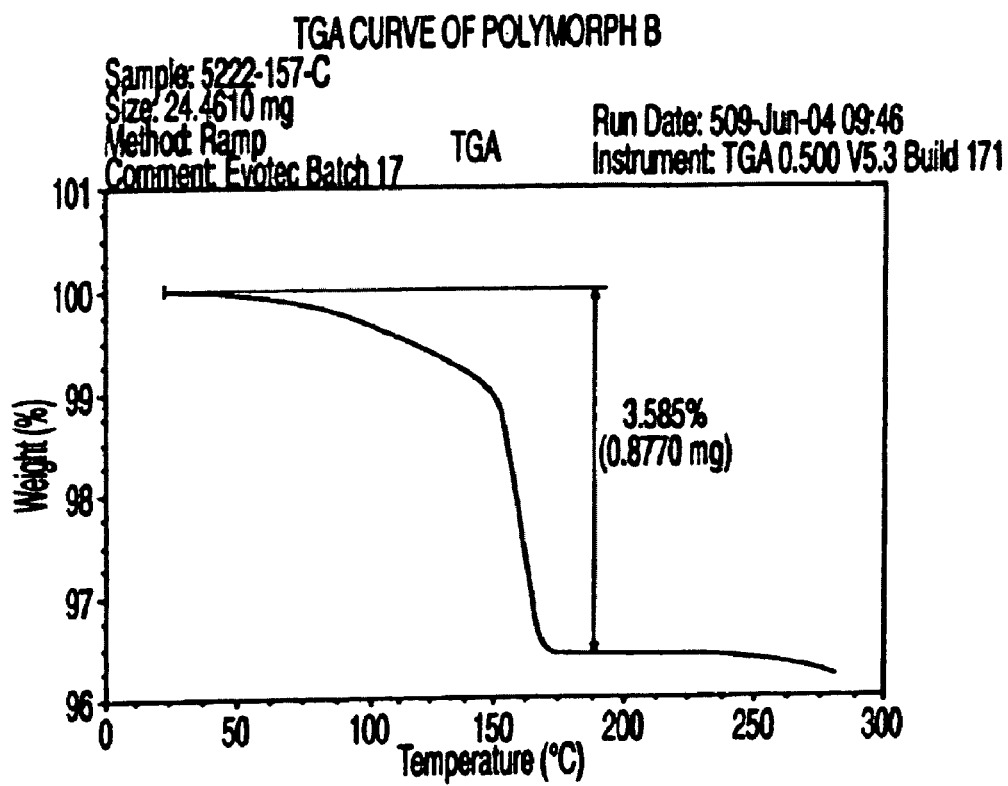
Figure 40:
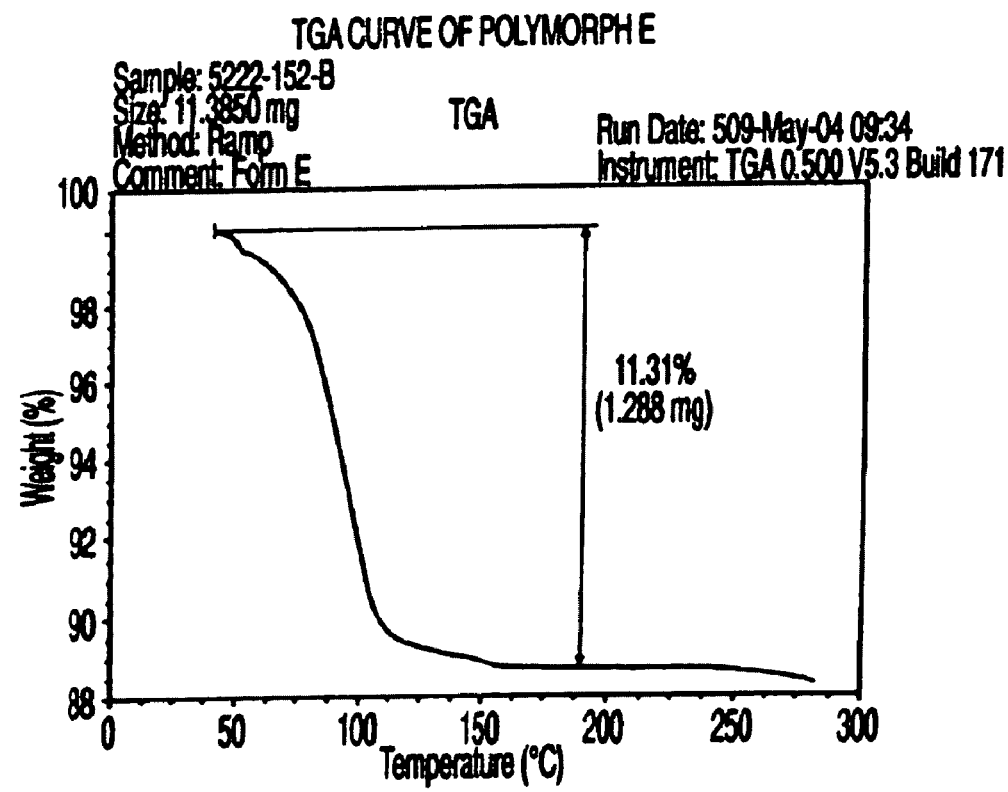
Figure 41:
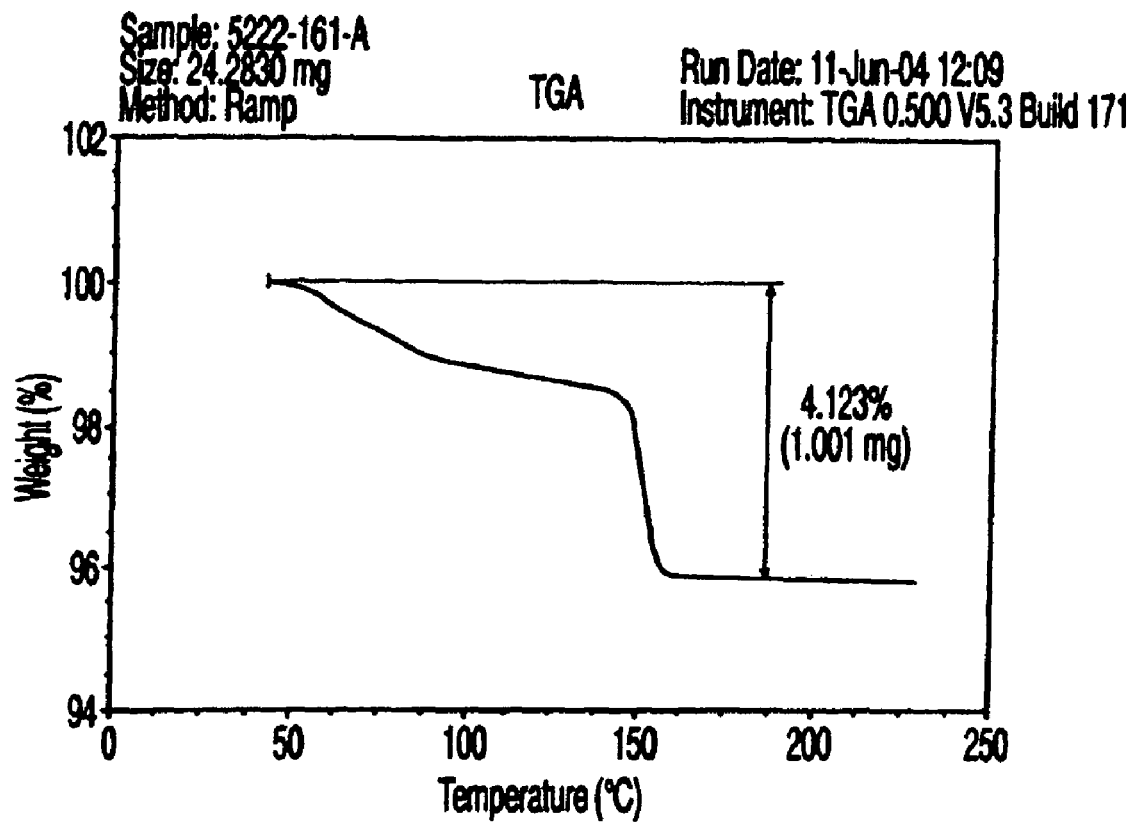
Figure 42:
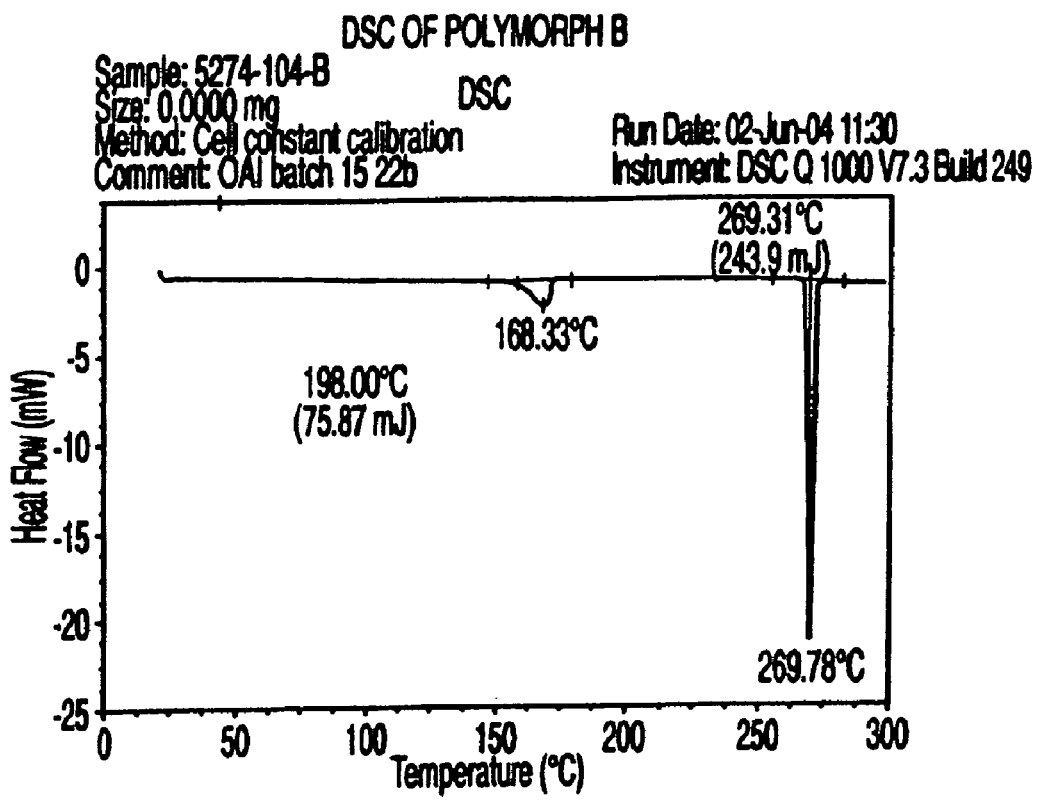
Figure 43:
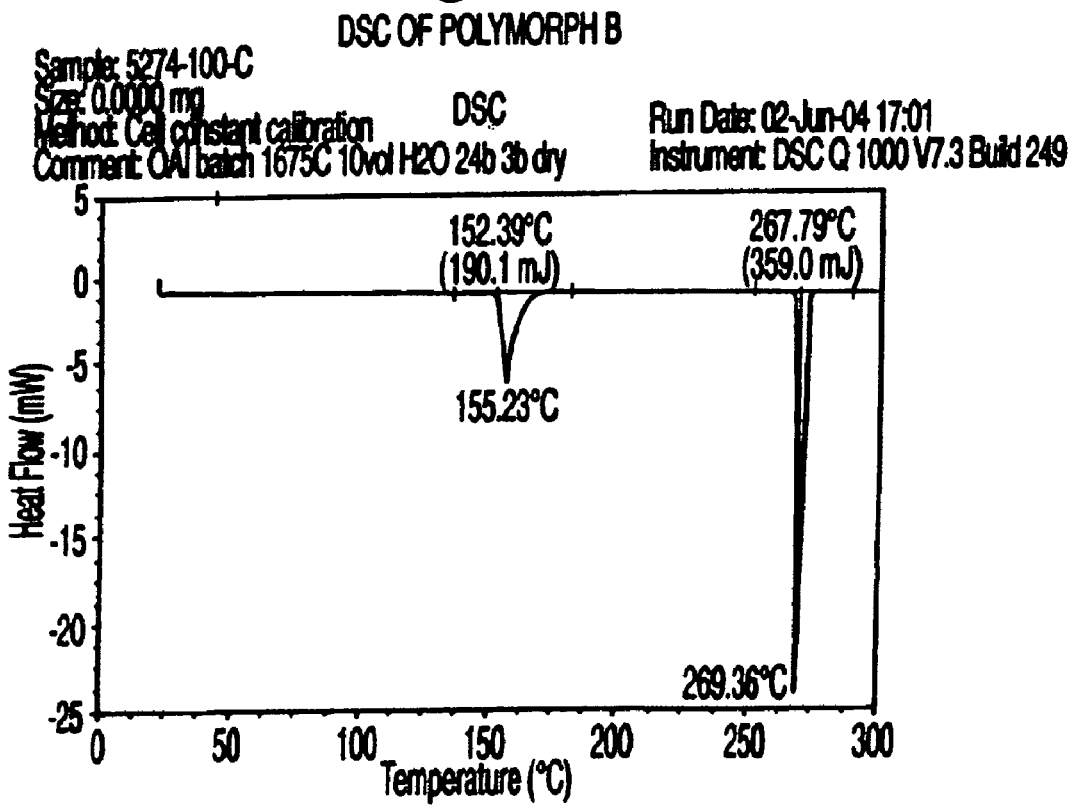
Figure 44:
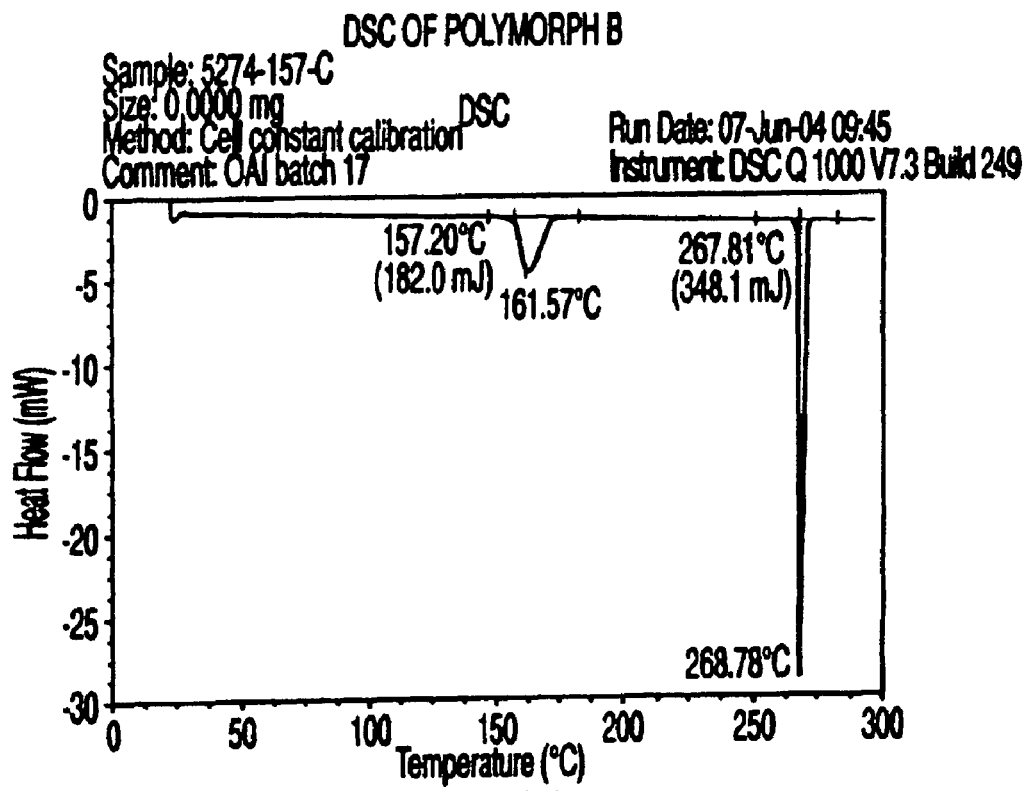
Figure 45:
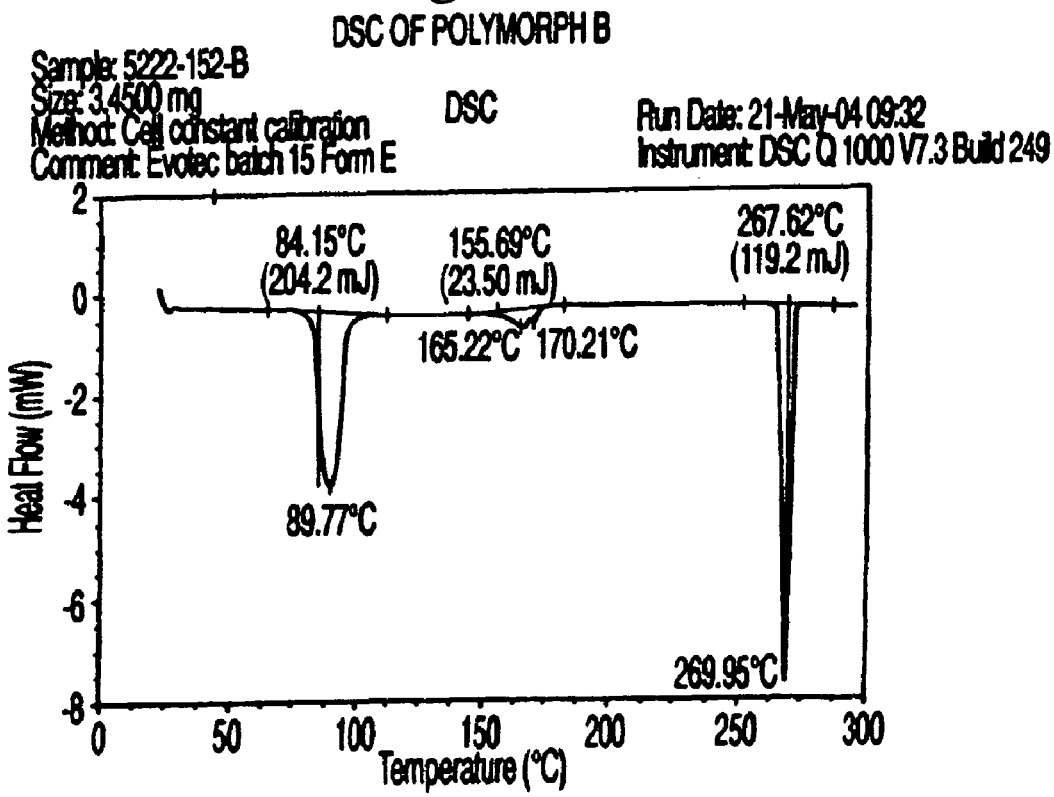
Figure 46:
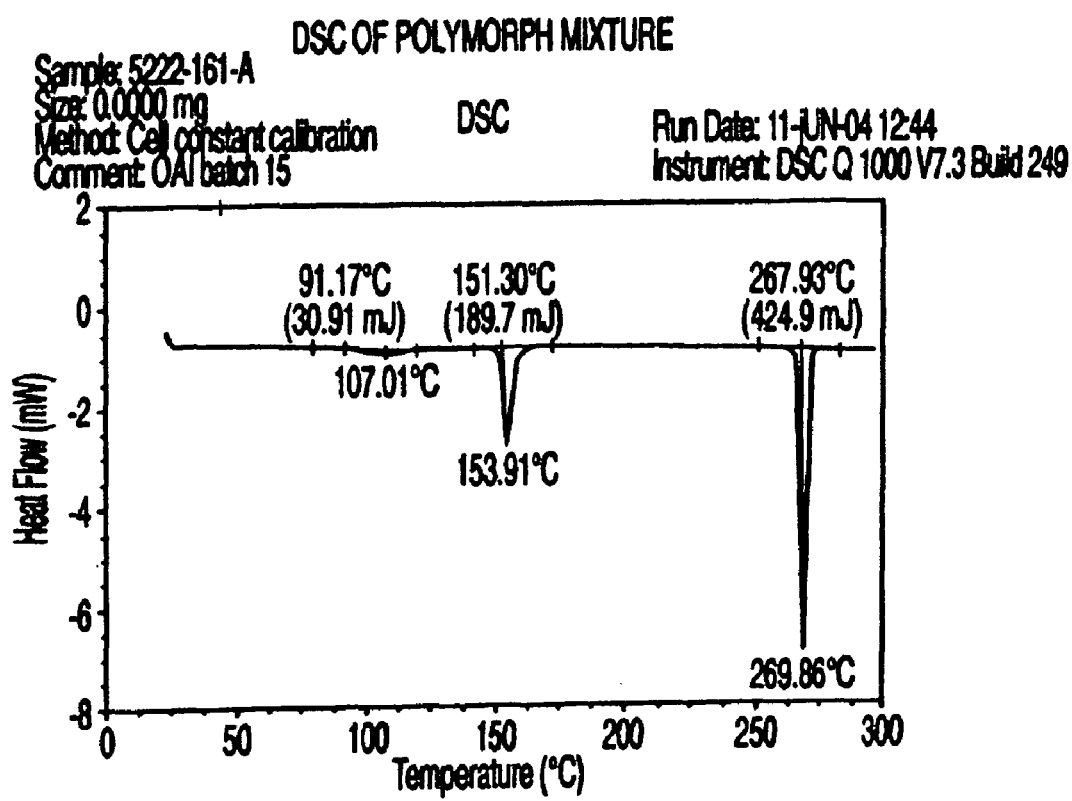
Figure 47:
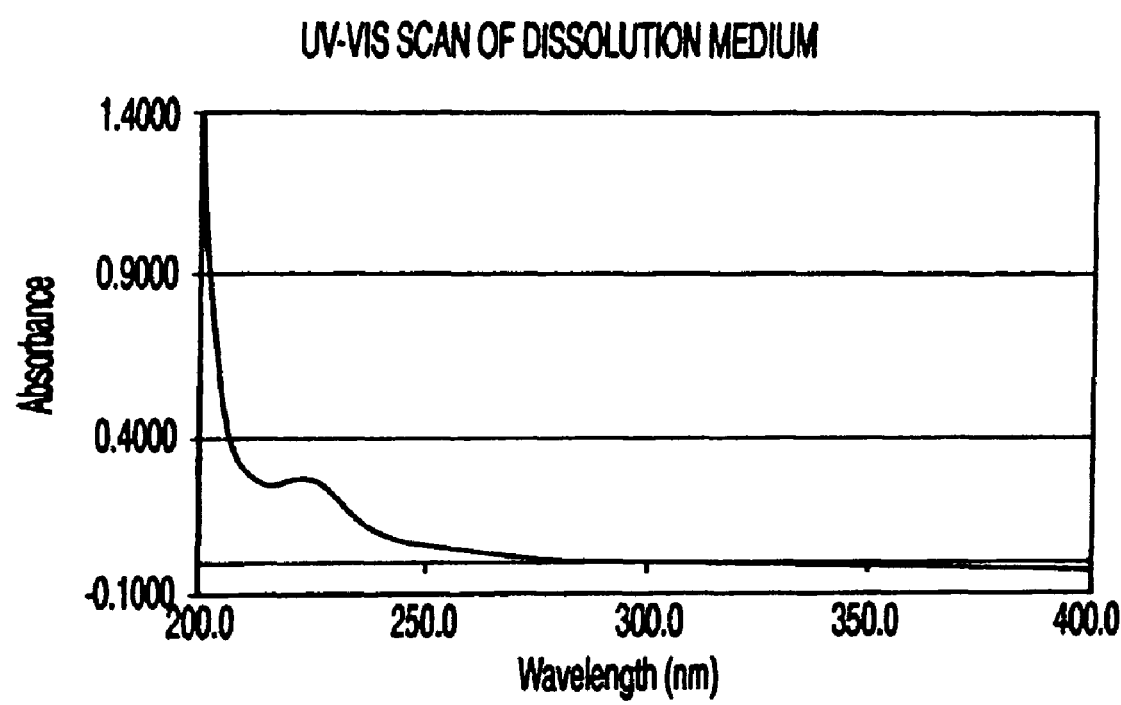
Figure 48:
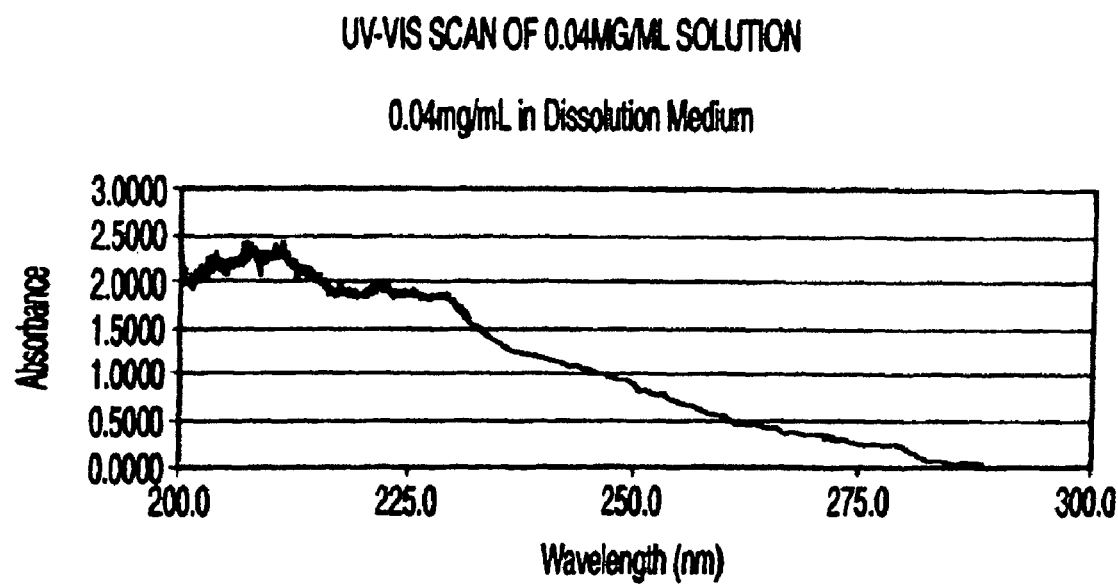
Figure 49:
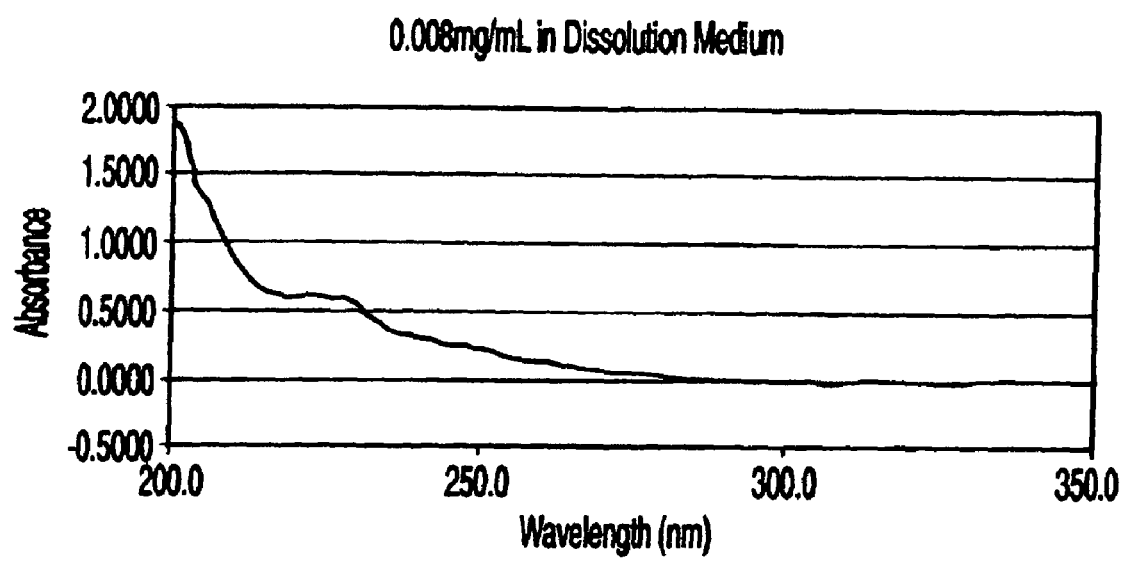
Figure 50:
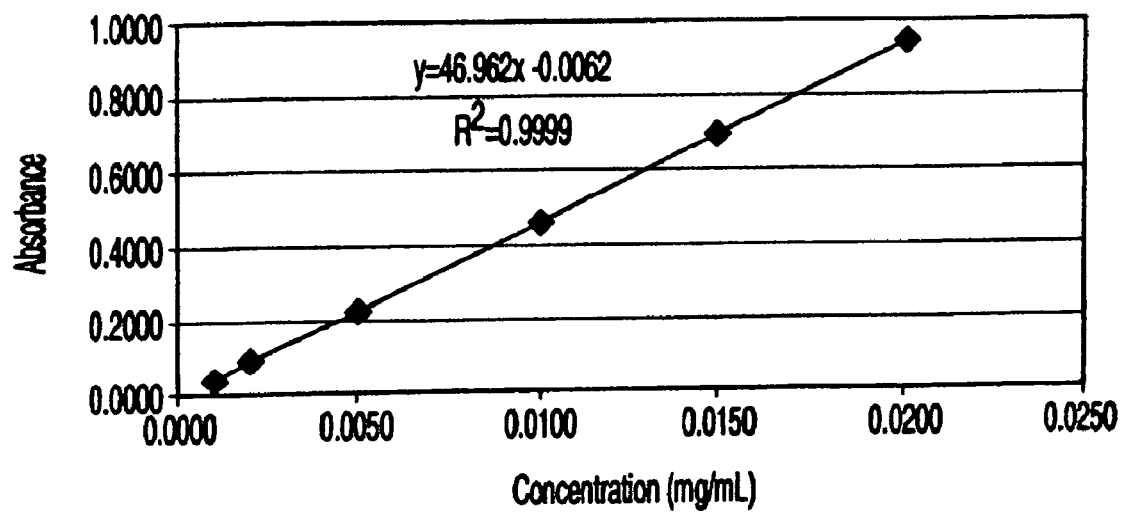
Figure 51:
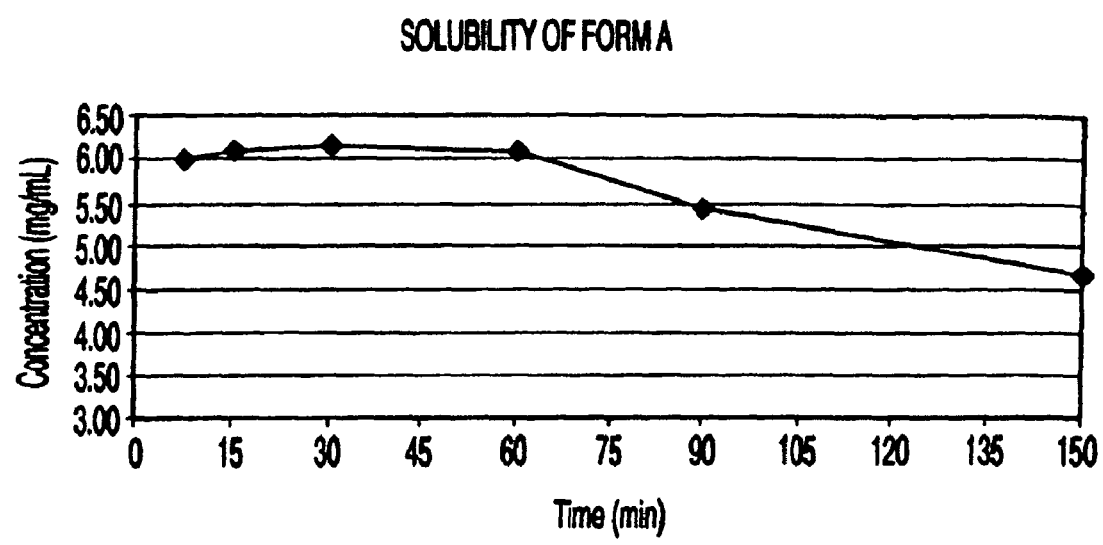
Figure 52:
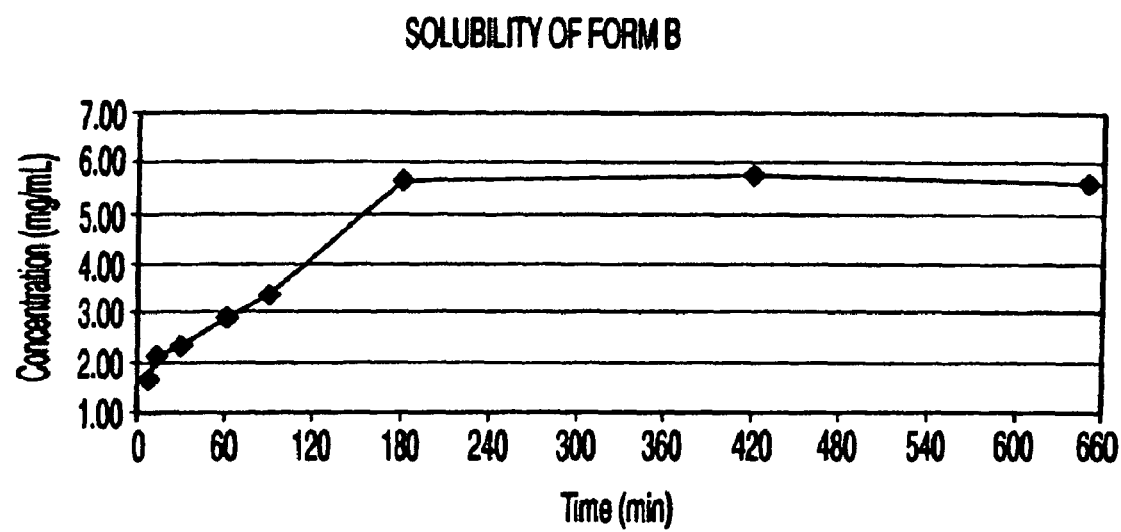
Figure 53:
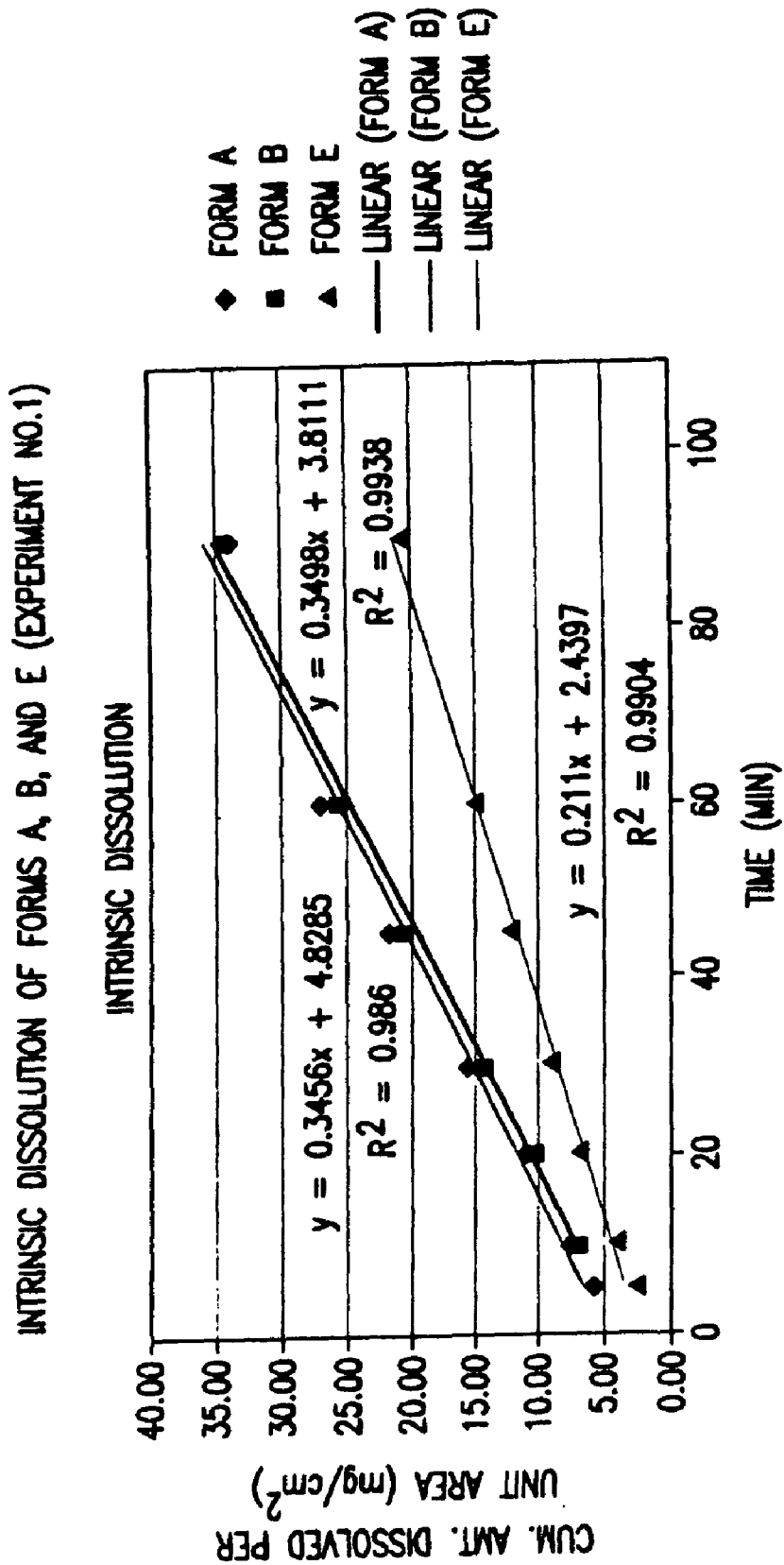

Specific aspects of the invention can be understood with reference to the attached figures:

FIG. 1 provides a representative X-ray powder diffraction (XRPD) pattern of Form A;

FIG. 2 provides a representative IR spectrum of Form A;

FIG. 3 provides a representative Raman spectrum of Form A;

FIG. 4 provides a representative thermogravimetric analysis (TGA) curve and a representative differential scanning calorimeter (DSC) thermogram of Form A;

FIG. 5 provides a representative moisture sorption/desorption isotherm of Form A;

FIG. 6 provides a representative XRPD pattern of Form B;

FIG. 7 provides a representative IR spectrum of Form B;

FIG. 8 provides a representative Raman spectrum of Form B;

FIG. 9 provides a representative TGA curve and a representative DSC thermogram of Form B;

FIG. 10 provides representative TG-IR results of Form B;

FIG. 11 provides a representative moisture sorption/desorption isotherm of Form B;

FIG. 12 provides a representative XRPD pattern of Form C;

FIG. 13 provides a representative IR spectrum of Form C;

FIG. 14 provides a representative Raman spectrum of Form C;

FIG. 15 provides a representative TGA curve and a representative DSC thermogram of Form C;

FIG. 16 provides representative TG-IR results of Form C;

FIG. 17 provides a representative moisture sorption/desorption isotherm of Form C;

FIG. 18 provides a representative XRPD pattern of Form D;

FIG. 19 provides a representative IR spectrum of Form D;

FIG. 20 provides a representative Raman spectrum of Form D;

FIG. 21 provides a representative TGA curve and a representative DSC thermogram of Form D;

FIG. 22 provides a representative moisture sorption/desorption isotherm of Form D;

FIG. 23 provides a representative XRPD pattern of Form E;

FIG. 24 provides a representative TGA curve and a representative DSC thermogram of Form E;

FIG. 25 provides a representative moisture sorption/desorption isotherm of Form E;

FIG. 26 provides a representative XRPD pattern for a sample of Form F;

FIG. 27 provides a representative thermogram of Form F;

FIG. 28 provides a representative XRPD pattern of Form G;

FIG. 29 provides a representative DSC thermogram for a sample of Form G;

FIG. 30 provides a representative XRPD pattern of Form H;

FIG. 31 provides a representative TGA curve and a representative DSC thermogram of Form H;

FIG. 32 provides a representative XRPD pattern of Form B;

FIG. 33 provides a representative XRPD pattern of Form B;

FIG. 34 provides a representative XRPD pattern of Form B;

FIG. 35 provides a representative XRPD pattern of Form E;

FIG. 36 provides a representative XRPD pattern of polymorph mixture;

FIG. 37 provides a representative TGA curve of Form B;

FIG. 38 provides a representative TGA curve of Form B;

FIG. 39 provides a representative TGA curve of Form B;

FIG. 40 provides a representative TGA curve of Form E;

FIG. 41 provides a representative TGA curve of polymorph mixture;

FIG. 42 provides a representative DSC thermogram of Form B;

FIG. 43 provides a representative DSC thermogram of Form B;

FIG. 44 provides a representative DSC thermogram of Form B;

FIG. 45 provides a representative DSC thermogram of Form E;

FIG. 46 provides a representative DSC thermogram of polymorph mixture;

FIG. 47 provides a UV-Vis scan of dissolution medium;

FIG. 48 provides a UV-Vis scan of 0.04 mg/ml of 3-(4-amino-1-oxo-1,3 dihydro-isoindol-2-yl)-piperidine-2,6-dione in dissolution medium;

FIG. 49 provides a UV-Vis scan of 0.008 mg/ml of 3-(4-amino-1-oxo-1,3 dihydro-isoindol-2-yl)-piperidine-2,6-dione in dissolution medium;

FIG. 50 provides a calibration curve for 3-(4-amino-1-oxo-1,3 dihydro-isoindol-2-yl)-piperidine-2,6-dione;

FIG. 51 provides a solubility curve of Form A;

FIG. 52 provides a solubility curve of Form B;

FIG. 53 provides an intrinsic dissolution of Forms A, B and E; and

Figure 54:
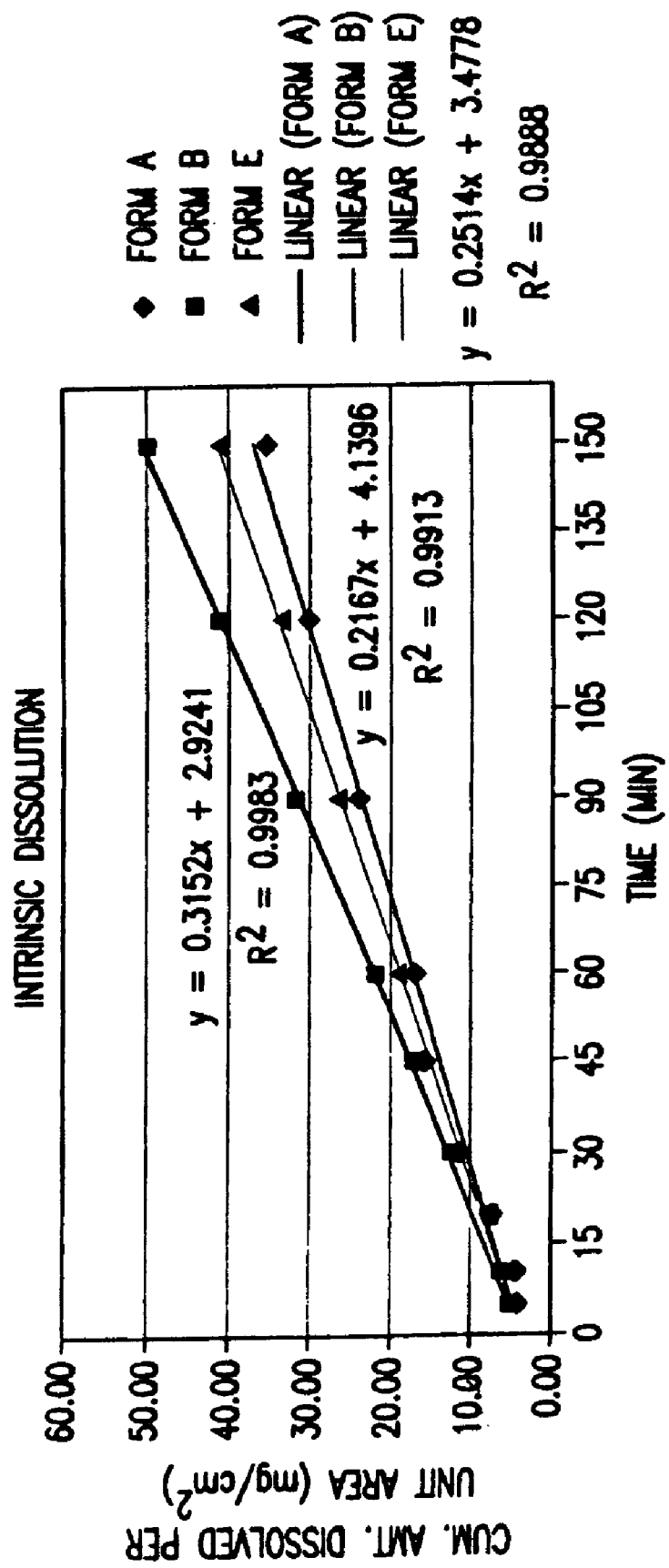
Figure 26:
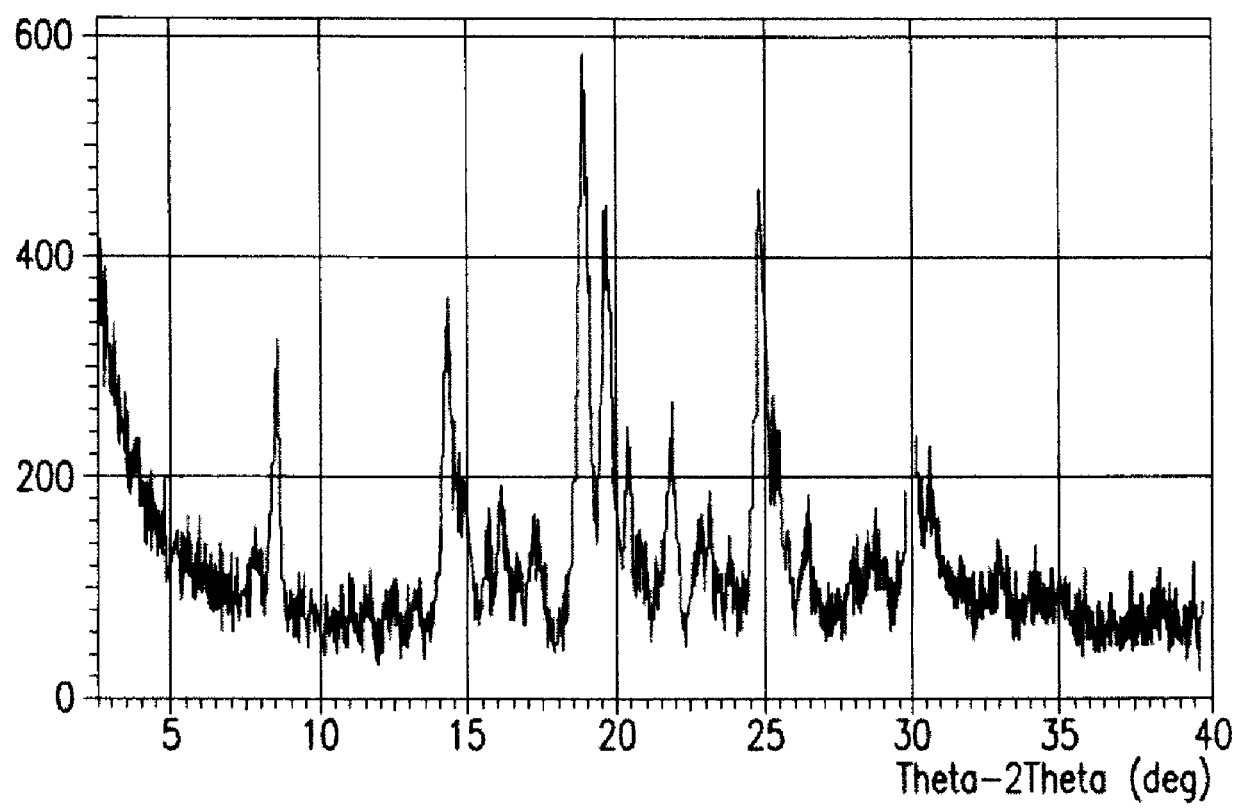

FIG. 54 provides an intrinsic dissolution of Forms A, B and E.

5. DETAILED DESCRIPTION OF THE INVENTION

5.1 Definitions

As used herein and unless otherwise indicated, the terms "treat," "treating" and "treatment" refer to the alleviation of a disease or disorder and/or at least one of its attendant symptoms.

As used herein and unless otherwise indicated, the terms "prevent," "preventing" and "prevention" refer to the inhibition of a symptom of a disease or disorder or the disease itself.

As used herein and unless otherwise indicated, the terms "polymorph" and "polymorphic form" refer to solid crystalline forms of a compound or complex. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot stage optical microscopy, scanning electron microscopy (SEM), electron crystallography and quantitative analysis, particle size analysis (PSA), surface area analysis, solubility, and rate of dissolution.

As used herein to refer to the spectra or data presented in graphical form (e.g., XRPD, IR, Raman and NMR spectra), and unless otherwise indicated, the term "peak" refers to a peak or other special feature that one skilled in the art would recognize as not attributable to background noise. The term "significant peaks" refers to peaks at least the median size (e.g., height) of other peaks in the spectrum or data, or at least 1.5, 2, or 2.5 times the median size of other peaks in the spectrum or data.

As used herein and unless otherwise indicated, the term "substantially pure" when used to describe a polymorph of a compound means a solid form of the compound that comprises that polymorph and is substantially free of other polymorphs of the compound. A representative substantially pure polymorph comprises greater than about 80% by weight of one polymorphic form of the compound and less than about 20% by weight of other polymorphic forms of the compound, more preferably greater than about 90% by weight of one polymorphic form of the compound and less than about 10% by weight of the other polymorphic forms of the compound, even more preferably greater than about 95% by weight of one polymorphic form of the compound and less than about 5% by weight of the other polymorphic forms of the compound, and most preferably greater than about 97% by weight of one polymorphic forms of the compound and less than about 3% by weight of the other polymorphic forms of the compound.

5.2 Polymorphic Forms

This invention is directed to polymorphic forms of 3-(4-amino-1-oxo-1,3 dihydro-isoindol-2-yl)-piperidine-2,6-dione, which has the structure shown below:

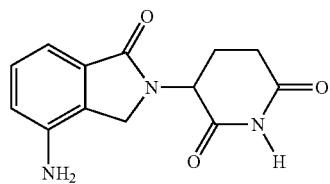

This compound can be prepared according to the methods described in U.S. Pat. Nos. 6,281,230 and 5,635,517, the entireties of which are incorporated herein by reference. For example, the compound can be prepared through catalytic hydrogenation of 3-(4-nitro-1-oxo-1,3 dihydro-isoindol-2-yl)-piperidine-2,6-dione. 3-(4-Nitro-1-oxo-1,3 dihydro-isoindol-2-yl)-piperidine-2,6-dione can be obtained by allowing 2,6-dioxopiperidin-3-ammonium chloride to react with methyl 2-bromomethyl-4-nitrobenzoate in dimethylformamide in the presence of triethylamine. The methyl 2-bromomethyl-4-nitrobenzoate in turn is obtained from the corresponding methyl ester of nitro-ortho-toluic acid by conventional bromination with N-bromosuccinimide under the influence of light.

Polymorphs of 3-(4-amino-1-oxo-1,3 dihydro-isoindol-2-yl)-piperidine-2,6-dione can be obtained by techniques known in the art, including solvent recrystallization, desolvation, vapor diffusion, rapid evaporation, slow evaporation, rapid cooling and slow cooling. Polymorphs can be made by dissolving a weighed quantity of 3-(4-amino-1-oxo-1,3 dihydro isoindol-2-yl)-piperidine-2,6-dione in various solvents at elevated temperatures. The solutions of the compound can then be filtered and allowed to evaporate either in an open vial (for fast hot evaporation) or in a vial covered with aluminum foil containing pinholes (hot slow evaporation). Polymorphs can also be obtained from slurries. Polymorphs can be crystallized from solutions or slurries using several methods. For example, a solution created at an elevated temperature (e.g., 60° C.) can be filtered quickly then allowed to cool to room temperature. Once at room temperature, the sample that did not crystallize can be moved to a refrigerator then filtered. Alternatively, the solutions can be crash cooled by dissolving the solid in a solvent at an increased temperature (e.g., 45-65° C.) followed by cooling in a dry ice/solvent bath.

One embodiment of the invention encompasses Form A of 3-(4-amino-1-oxo-1,3 dihydro-isoindol-2-yl)-piperidine-2,6-dione. Form A is an unsolvated, crystalline material that can be obtained from non-aqueous solvent systems. Another embodiment of the invention encompasses Form B of 3-(4-amino-1-oxo-1,3 dihydro-isoindol-2-yl)-piperidine-2,6-dione. Form B is a hemihydrated, crystalline material that can be obtained from various solvent systems. Another embodiment of the invention encompasses Form C of 3-(4-amino-1-oxo-1,3 dihydro-isoindol-2-yl)-piperidine-2,6-dione. Form C is a hemisolvated crystalline material that can be obtained from solvents such as, but not limited to, acetone. Another embodiment of the invention encompasses Form D of 3-(4-amino-1-oxo-1,3 dihydro-isoindol-2-yl)-piperidine-2,6-dione. Form D is a crystalline, solvated polymorph prepared from a mixture of acetonitrile and water. Another embodiment of the invention encompasses Form E of 3-(4-amino-1-oxo-1,3 dihydro-isoindol-2-yl)-piperidine-2,6-dione. Form E is a dihydrated, crystalline material. Another embodiment of the invention encompasses Form F of 3-(4-amino-1-oxo-1,3 dihydro-isoindol-2-yl)-piperidine-2,6-dione. Form F is an unsolvated, crystalline material that can be obtained from the dehydration of Form E. Another embodiment of the invention encompasses Form G of 3-(4-amino-1-oxo-1,3 dihydro-isoindol-2-yl)-piperidine-2,6-dione. Form G is an unsolvated, crystalline material that can be obtained from slurrying forms B and E in a solvent such as, but not limited to, tetrahydrofuran (THF). Another embodiment of the invention encompasses Form H of 3-(4-amino-1-oxo-1,3 dihydro-isoindol-2-yl)-piperidine-2,6-dione. Form H is a partially hydrated crystalline material that can be obtained by exposing Form E to 0% relative humidity. Each of these forms is discussed in detail below.

Another embodiment of the invention encompasses a composition comprising amorphous 3-(4-amino-1-oxo-1,3 dihydro-isoindol-2-yl)-piperidine-2,6-dione and crystalline 3-(4-amino-1-oxo-1,3 dihydro-isoindol-2-yl)-piperidine-2,6-dione of form A, B, C, D, E, F, G or H. Specific compositions can comprise greater than about 50, 75, 90 or 95 weight percent crystalline 3-(4-amino-1-oxo-1,3 dihydro-isoindol-2-yl)-piperidine-2,6-dione.

Another embodiment of the invention encompasses a composition comprising at least two crystalline forms of 3-(4-amino-1-oxo-1,3 dihydro-isoindol-2-yl)-piperidine-2,6-dione (e.g., a mixture of polymorph forms B and E).

5.2.1 Form A

The data described herein for Form A, as well as for Forms B-H, were obtained using the experimental methods described in Examples 6.3-6.7, provided below.

Form A can be obtained from various solvents, including, but not limited to 1-butanol, butyl acetate, ethanol, ethyl acetate, methanol, methyl ethyl ketone, and THF. FIG. 1 shows a representative XRPD pattern of Form A. The pattern is characterized by peaks, preferably significant peaks, at approximately 8, 14.5, 16, 17.5, 20.5, 24, and 26 degrees 2θ. Representative IR and Raman spectra data are provided in FIGS. 2 and 3.

Representative thermal characteristics of Form A are shown in FIG. 4. TGA data show a small weight increase up to about 150° C., indicating an unsolvated material. Weight loss above 150° C. is attributed to decomposition. The DSC curve of Form A exhibits an endotherm at about 270° C.

Representative moisture sorption and desorption data are plotted in FIG. 5. Form A does not exhibit a significant weight gain from 5 to 95% relative humidity. Equilibrium can be obtained at each relative humidity step. As the form dries from 95% back down to 5% relative humidity, it tends to maintain its weight such that at 5% relative humidity it has typically lost only about 0.003% by weight from start to finish Form A is capable of remaining a crystalline solid for about 11 days when stored at about 22, 45, 58, and 84% relative humidity.

Interconversion studies show that Form A can convert to Form B in aqueous solvent systems and can convert to Form C in acetone solvent systems. Form A tends to be stable in anhydrous solvent systems. In water systems and in the presence of Form E, Form A tends to convert to Form E.

When stored for a period of about 85 days under two different temperature/relative humidity stress conditions (room temperature/0% relative humidity (RH) and 40° C./93% RH), Form A typically does not convert to a different form.

In sum, Form A is a crystalline, unsolvated solid that melts at approximately 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

5.2.2 Form B

Form B can be obtained from many solvents, including, but not limited to, hexane, toluene, and water. FIG. 6 shows a representative XRPD pattern of Form B, characterized by peaks at approximately 16, 18, 22 and 27 degrees 2θ.

Solution proton NMR confirm that Form B is a form of 3-(4-amino-1-oxo-1,3 dihydro-isoindol-2-yl)-piperidine-2,6-dione. Representative IR and Raman spectra are shown in FIGS. 7 and 8, respectively. Compared to Form A, the IR spectrum for Form B has peaks at approximately 3513 and 1960 cm$^{-1}$.

Representative DSC and TGA data for Form B are shown in FIG. 9. The DSC curve exhibits endotherms at about 146 and 268° C. These events are identified as dehydration and melting by hot stage microscopy experiments. Form B typically loses about 3.1% volatiles up to about 175° C. (per approximately 0.46 moles of water). Comparison of the IR spectrum of the volatiles with that of water indicates that they are water (See FIG. 10). Calculations from TGA data indicate that Form B is a hemihydrate. Karl Fischer water analysis also supports this conclusion.

Representative moisture sorption and desorption data are shown in FIG. 11. Form B typically does not exhibit a significant weight gain from 5% to 95% relative humidity, when equilibrium is obtained at each relative humidity step. As Form B dries from 95% back down to 5% relative humidity, it tends to maintain its weight such that at 5% relative humidity it typically has gained only about 0.022% by weight (about 0.003 mg) from start to finish Form B does not convert to a different form upon exposure to about 84% relative humidity for about ten days.

Interconversion studies show that Form B typically converts to Form A in a THF solvent system, and typically converts to Form C in an acetone solvent system. In aqueous solvent systems such as pure water and 10% water solutions, Form B is the most stable of the polymorphic forms of 3-(4-amino-1-oxo-1,3 dihydro-isoindol-2-yl)-piperidine-2,6-dione. However, it can convert to Form E in the presence of water. Desolvation experiments show that upon heating at about 175° C. for about five minutes, Form B typically converts to Form A.

When stored for a period of about 85 days under two different temperature/relative humidity stress conditions (room temperature/0% RH and 40° C./93% RH), Form B does not convert to a different form.

In sum, Form B is a hemihydrated, crystalline solid which has a DSC thermogram exhibiting endotherms at about 146 and about 268° C. Interconversion studies show that Form B converts to Form E in aqueous solvent systems, and converts to other forms in acetone and other anhydrous systems.

5.2.3 Form C

Form C can be obtained from evaporations, slurries and slow cools in acetone solvent systems. A representative XRPD pattern of this form is shown in FIG. 12. The data are characterized by peaks at approximately 15.5 and 25 degrees 2θ.

Solution proton NMR indicates that the 3-(4-amino-1-oxo-1,3 dihydro-isoindol-2-yl)-piperidine-2,6-dione molecule is intact. Representative IR and Raman spectra are shown in FIGS. 13 and 14, respectively. The IR spectrum of Form C is characterized by peaks at approximately 3466, 3373, and 3318 cm$^{-1}$. The Raman spectrum of Form C is characterized by peaks at about 3366, 3321, 1101, and 595 cm$^{-1}$.

Representative thermal characteristics for Form C are plotted in FIG. 15. Form C loses about 10.02% volatiles up to about 175° C., indicating it is a solvated material. Weight loss above about 175° C. is attributed to decomposition. Identification of volatiles in Form C can be accomplished with TG-IR experiments. The representative IR spectrum captured after several minutes of heating, as depicted in FIG. 13, when compared with a spectral library, shows acetone to be the best match. Calculations from TGA data show that Form C is a hemisolvate (approximately 0.497 moles of acetone). The DSC curve for Form C, shown in FIG. 15, exhibits endotherms at about 150 and about 269° C. The endotherm at about 150° C. is attributed to solvent loss based on observations made during hot stage microscopy experiments. The endotherm at about 269° C. is attributed to the melt based on hot stage experiments.

Representative moisture sorption and desorption balance data are shown in FIG. 17. Form C does not exhibit a significant weight gain from 5 to 85% relative humidity, when equilibrium is obtained at each relative humidity step up to 85% relative humidity. At 95% relative humidity, Form C experiences a significant weight loss of about 6.03%. As the sample dries from 95% back down to 5% relative humidity, the sample maintains the weight achieved at the end of the adsorption phase at each step down to 5% relative humidity. Form C is capable of converting to Form B when stored at about 84% relative humidity for approximately ten days.

Interconversion studies show that Form C typically converts to Form A in a THF solvent system and typically converts to Form E in an aqueous solvent system. In an acetone solvent system, Form C is the most stable form of 3-(4-amino-1-oxo-1,3 dihydro-isoindol-2-yl)-piperidine-2,6-dione. Desolvation experiments performed on Form C show that upon heating at about 150° C. for about five minutes, Form C will typically convert to Form A.

In sum, Form C is a crystalline, hemisolvated solid, which has a DSC thermogram exhibiting endotherms at about 150 and about 269° C. Form C is not hygroscopic below about 85% RH, but can convert to Form B at higher relative humidities.

5.2.4 Form D

Form D can be obtained from evaporation in acetonitrile solvent systems. A representative XRPD pattern of the form is shown in FIG. 18. The pattern is characterized by peaks at approximately 27 and 28 degrees 2θ.

Solution proton NMR indicates that the 3-(4-amino-1-oxo-1,3 dihydro-isoindol-2-yl)-piperidine-2,6-dione molecule is intact. Representative IR and Raman spectra are shown in FIGS. 19 and 20, respectively. The IR spectrum of Form D is characterized by peaks at approximately 3509, 2299, and 2256 cm$^{-1}$. The Raman spectrum of Form D is characterized by peaks at approximately 2943, 2889, 2297, 2260, 1646, and 1150 cm$^{-1}$.

Representative thermal characteristics for Form D are plotted in FIG. 21. Form D loses about 6.75% volatiles up to about 175° C., indicating a solvated material. Weight loss above about 175° C. is attributed to decomposition. TG-IR experiments indicate that the volatiles are water and acetonitrile. Calculations from TG data show that about one mole of water is present in the sample. A representative DSC curve for Form D exhibits endotherms at about 122 and about 270° C. The endotherm at about 122° C. is attributed to loss of volatiles based on observations made during hot stage microscopy experiments. The endotherm at about 270° C. is attributed to the melt based on hot stage experiments.

Representative moisture sorption and desorption data are plotted in FIG. 22. Form D does not exhibit a significant weight gain from 5 to 95% relative humidity when equilibrium is obtained at each relative humidity step. As the form dries from 95% back down to 5% relative humidity, it maintains its weight such that at 5% relative humidity the form has typically gained only about 0.39% by weight (about 0.012 mg) from start to finish. Form A is capable of converting to Form B when stored at about 84% relative humidity for approximately ten days.

Interconversion studies show that Form D is capable of converting to Form A in a THF solvent system, to Form E in an aqueous solvent system, and to Form C in an acetone solvent system. Desolvation experiments performed on Form D show that upon heating at about 150° C. for about five minutes Form D will typically convert to Form A.

In sum, Form D is a crystalline solid, solvated with both water and acetonitrile, which has a DSC thermogram exhibiting endotherms at about 122 and about 270° C. Form D is either weakly or not hygroscopic, but will typically convert to Form B when stressed at higher relative humidities.

5.2.5 Form E

Form E can be obtained by slurrying 3-(4-amino-1-oxo-1,3 dihydro-isoindol-2-yl)-piperidine-2,6-dione in water and by a slow evaporation of 3-(4-amino-1-oxo-1,3 dihydro-isoindol-2-yl)-piperidine-2,6-dione in a solvent system with a ratio of about 9:1 acetone:water. A representative XRPD pattern is shown in FIG. 23. The data are characterized by peaks at approximately 20, 24.5 and 29 degrees 2θ.

Representative thermal characteristics of Form E are plotted in FIG. 24. Form E typically loses about 10.58% volatiles up to about 125° C., indicating that it is a solvated material. A second weight loss of an additional about 1.38% was observed between about 125° C. and about 175° C. Weight loss above about 175° C. is attributed to decomposition. Karl Fischer and TG-IR experiments support the conclusion that the volatile weight loss in Form E is due to water. The representative DSC curve for Form E exhibits endotherms at about 99, 161 and 269° C. Based on observations made during hot stage microscopy experiments, the endotherms at about 99 and about 161° C. are attributed to loss of volatiles. The endotherm at about 269° C. is attributed to the melt based on hot stage experiments.

Representative moisture sorption and desorption data are plotted in FIG. 25. Form E typically does not exhibit a significant weight change from 5 to 95% relative humidity when equilibrium is obtained at each relative humidity step. As the sample dried from 95% back down to 5% relative humidity, the sample continues to maintain weight such that at 5% relative humidity the sample has lost only about 0.0528% by weight from start to finish.

Interconversion studies show that Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

When stored for a period of 85 days under two different temperature/relative humidity stress conditions (room temperature/0% RH and 40° C./93% RH) Form E typically does not convert to a different form. When stored for seven days at room temperature/0% RH, Form E can convert to a new form, Form H.

5.2.6 Form F

Form F can be obtained by complete dehydration of Form E. A representative XRPD pattern of Form F, shown in FIG. 26, is characterized by peaks at approximately 19, 19.5 and 25 degrees 2θ.

Representative thermal characteristics of Form F are shown in FIG. 27. The representative DSC curve for Form F exhibits an endotherm at about 269° C. preceded directly by two smaller endotherms indicative of a crystallized form of 3-(4-amino-1-oxo-1,3 dihydro-isoindol-2-yl)-piperidine-2,6-dione. The DSC thermogram does not show any thermal events prior to the melt, suggesting that it is an unsolvated material.

5.2.7 Form G

Form G can be obtained by slurrying forms B and E in THF. A representative XRPD pattern of this form, shown in FIG. 28, is characterized by a peak at approximately 23 degrees 2θ. Two other peaks unique to Form G appear at approximately 21 and 24.5 degrees 2θ.

Representative thermal characteristics of Form G are plotted in FIG. 29. A representative DSC curve for Form G exhibits an endotherm at about 248° C. followed by a small, broad exotherm at about 267° C. No thermal events are seen in the DSC thermogram at lower temperatures, suggesting that it is an unsolvated material.

5.2.8 Form H

Form H can be obtained by storing Form E at room temperature and 0% RH for about 7 days. A representative XRPD pattern is shown in FIG. 30. The pattern is characterized by a peak at 15 degrees 2θ, and two other peaks at 26 and 31 degrees 2θ.

Representative thermal characteristics are shown in FIG. 31. Form H loses about 1.67% volatiles up to about 150° C. Weight loss above about 150° C. is attributed to decomposition. Karl Fischer data shows that Form H typically contains about 1.77% water (about 0.26 moles), suggesting that the weight loss seen in the TG is due to dehydration. The DSC thermogram shows a broad endotherm between about 50° C. and about 125° C., corresponding to the dehydration of Form H and a sharp endotherm at about 269° C., which is likely due to a melt.

When slurried in water with either Forms A or B, after about 14 days Form H can convert to Form E. When slurried in THF, Form H can convert to Form A. When slurried in acetone, Form H can convert to Form C.

In sum, Form H is a crystalline solid, hydrated with about 0.25 moles of water, which has a DSC thermogram exhibiting an endotherm between about 50 and 125° C. and an endotherm at about 269° C.

5.3 Methods of Use and Pharmaceutical Compositions

Polymorphs of the invention exhibit physical characteristics that are beneficial for drug manufacture, storage or use. All polymorphs of the invention have utility as pharmaceutically active ingredients or intermediates thereof.

This invention encompasses methods of treating and preventing a wide variety of diseases and conditions using polymorphs of 3-(4-amino-1-oxo-1,3-dihydro-isoindol-2-yl)-piperidine-2,6-dione. In each of the methods, a therapeutically or prophylactically effective amount of the compound is administered to a patient in need of such treatment or prevention. Examples of such disease and conditions include, but are not limited to, diseases associated with undesired angiogenesis, cancer (e.g., solid and blood borne tumors), inflammatory diseases, autoimmune diseases, and immune diseases. Examples of cancers and pre-cancerous conditions include those described in U.S. Pat. Nos. 6,281,230 and 5,635,517 to Muller et al. and in various U.S. patent applications to Zeldis, including application Ser. Nos. 10/411,649, filed Apr. 11, 2003 (Treatment of Myelodisplastic Syndrome); 10/438,213 filed May 15, 2003 (Treatment of Various Types of Cancer); 10/411,656, filed Apr. 11, 2003 (Treatment of Myeloproliferative Diseases). Examples of other diseases and disorders that can be treated or prevented using compositions of the invention are described in U.S. Pat. Nos. 6,235,756 and 6,114,335 to D'Amato and in other U.S. patent applications to Zeldis, including Ser. Nos. 10/693,794, filed Oct. 23, 2003 (Treatment of Pain Syndrome) and 10/699,154, filed Oct. 30, 2003 (Treatment of Macular Degeneration). The entirety of each of the patents and patent applications cited herein is incorporated herein by reference.

Depending on the disease to be treated and the subject's condition, polymorphs of the invention can be administered by oral, parenteral (e.g., intramuscular, intraperitoneal, intravenous, ICV, intracisternal injection or infusion, subcutaneous injection, or implantation), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Because individual polymorphs have different dissolution, stability, and other properties, the optimal polymorph used in methods of treatment may depend on the route of administration. For example, forms that are readily soluble in aqueous solutions are preferably used to provide liquid dosage forms, whereas forms that exhibit great thermal stability may be preferred in the manufacture of solid dosage forms (e.g., tablets and capsules).

Although the physical characteristics of polymorphs can, in some cases, affect their bioavailability, amounts of the polymorphs that are therapeutically or prophylactically effective in the treatment of various disease and conditions can be readily determined by those of ordinary skill in the pharmacy or medical arts. In certain embodiments of the invention, a polymorph is administered orally and in a single or divided daily doses in an amount of from about 0.10 to about 150 mg/day, or from about 5 to about 25 mg/day. In other embodiments, a polymorph is administered every other day in an amount of from about 0.10 to about 150 mg/day, or from about 5 to about 25 mg/day.

The invention encompasses pharmaceutical compositions and single unit dosage forms that can be used in methods of treatment and prevention, which comprise one or more polymorphs of 3-(4-amino-1-oxo-1,3-dihydro-isoindol-2-yl)-piperidine-2,6-dione and optionally one or more excipients or diluents. Specific compositions and dosage forms are disclosed in the various patents and patent applications incorporated herein by reference. In one embodiment, a single dosage form comprises a polymorph (e.g., Form B) in an amount of about 5, 10, 25 or 50 mg.

6. EXAMPLES

6.1 Polymorph Screen

A polymorph screen to generate the different solid forms of 3-(4-amino-1-oxo-1,3 dihydro-isoindol-2-yl)-piperidine-2,6-dione was carried out as follows.

A weighed sample of 3-(4-amino-1-oxo-1,3 dihydro-isoindol-2-yl)-piperidine-2,6-dione (usually about 10 mg) was treated with aliquots of the test solvent. Solvents were either reagent or HPLC grade. The aliquots were usually about 200 µL. Between additions, the mixture was usually shaken or sonicated. When the solids dissolved, as judged by visual inspection, estimated solubilities were calculated. Solubilities were estimated from these experiments based on the total solvent used to provide a solution. Actual solubilities may have been greater than those calculated due to the use of too-large solvent aliquots or to a slow rate of dissolution.

Samples were created by generating solutions (usually about 30 mg in 20 mL) at elevated temperatures, filtering, and allowing the solution to evaporate whether in an open vial (hot fast evaporation) or in a vial covered with aluminum foil containing pinholes (hot slow evaporation).

Slurry experiments were also performed. Usually about 25 mg of solid was placed in either 3 or 5 mL of solvent. The samples were then placed on orbital shakers at either ambient temperature or 40° C. for 410 days.

Crystallizations were performed using various cooling methods. Solid was dissolved in a solvent at an elevated temperature (e.g., about 60° C.), filtered quickly and allowed to cool to room temperature. Once at room temperature, samples that did not crystallize were moved to a refrigerator. Solids were removed by filtration or decantation and allowed to dry in the air. Crash cools were performed by dissolving solid in a solvent at an increased temperature (e.g., about 45-65° C.) followed by cooling in a dry ice/acetone bath.

Hygroscopicity studies were performed by placing portions of each polymorph in an 84% relative humidity chamber for approximately one week.

Desolvation studies were carried out by heating each polymorph in a 70° C. oven for approximately one week.

Interconversion experiments were carried out by making slurries containing two forms in a saturated solvent. The slurries were agitated for approximately 7-20 days at ambient temperature. The insoluble solids were recovered by filtration and analyzed using XRPD.

6.2 Preparation of Polymorphic Forms

Eight solid forms of 3-(4-amino-1-oxo-1,3 dihydro-isoindol-2-yl)-piperidine-2,6-dione were prepared as described below.

Form A was obtained by crystallization from various non-aqueous solvents including 1-butanol, butyl acetate, ethanol, ethyl acetate, methanol, methyl ethyl ketone, and tetrahydrofuran. Form B was also obtained by crystallization from the solvents hexane, toluene and water. Form C was obtained from evaporations, slurries, and slow cools in acetone solvent systems. Form D was obtained from evaporations in acetonitrile solvent systems. Form E was obtained most readily by slurrying 3-(4-amino-1-oxo-1,3 dihydro-isoindol-2-yl)-piperidine-2,6-dione in water. Form F was obtained by complete desolvation of Form E. It is found to be an unsolvated, crystalline material that melts at about 269° C. Form G was obtained by slurrying forms B and E in THF. Form H was obtained by stressing Form E at room temperature and 0% RH for 7 days.

6.2.1 Synthesis of Polymorphs B and E

Form B is the desired polymorph for the active pharmaceutical ingredient (API) of 3-(4-amino-1-oxo-1,3 dihydro-isoindol-2-yl)-piperidine-2,6-dione. This form has been used in the formulation of API into drug product for clinical studies. Three batches were produced as apparent mixtures of polymorphs in the non-micronized API of 3-(4-amino-1-oxo-1,3 dihydro-isoindol-2-yl)-piperidine-2,6-dione.

Development work was carried out to define a process that would generate polymorph B from this mixture of polymorphs and could be implemented for strict polymorphic controls in the validation batches and future manufacturing of API of 3-(4-amino-1-oxo-1,3 dihydro-isoindol-2-yl)-piperidine-2, 6-dione. Characterization of polymorphic forms produced during the work was performed by XRPD, DSC, TGA and KF.

A process was also developed for the large-scale preparation of Form E. Polymorph E material was prepared in order to carry out a comparison with polymorph B drug product in capsule dissolution testing of 3-(4-amino-1-oxo-1,3 dihydro-isoindol-2-yl)-piperidine-2,6-dione. 150 g of a mixture of polymorphs in 3 L of water was stirred at room temperature for 48 hours. The product was collected by filtration and dried at 25° C. for 24 hours under vacuum. XRPD, DSC, TGA, KF and HPLC analyses confirmed that the material isolated was polymorph E.

In a preliminary work, it was demonstrated that stirring a suspension of a mixture of polymorphs of 3-(4-amino-1-oxo-1,3 dihydro-isoindol-2-yl)-piperidine-2,6-dione with water at high temperature (75° C.) for an extended period of time converted this mixture of polymorphs exclusively to form B. Several specific parameters were identified including temperature, solvent volume and drying parameters (temperature and vacuum). XRPD, DSC, TGA, KF and HPLC analyses were used to characterize all of the batches. After completing the optimization work, the optimized process was scaled-up to 100-200 g on three lots of API. Drying studies were carried out at 20° C., 30° C. and 40° C., and 65° C. with a vacuum of 150 mm of Hg. The results are shown in Tables 1-5.

The cooling and holding periods of 3-(4-amino-1-oxo-1,3 dihydro-isoindol-2-yl)-piperidine-2,6-dione slurry were studied. The experimental laboratory data suggests that polymorph B seems to be forming first, and overtime equilibration to polymorph E at RT conditions occurs, therefore generating a mixture of polymorphs B and E. This result supports the fact that polymorph B seems to be a kinetic product, and that prolonged processing time converts the material to polymorph E resulting in a mixture of polymorphs B and E.

A laboratory procedure was developed to exclusively produce polymorph B of 3-(4-amino-1-oxo-1,3 dihydro-isoindol-2-yl)-piperidine-2,6-dione. The procedure includes a stirred 10 volume water slurry at ~75° C. for 6-24 hours. The following preferred process parameters have been identified:
1. Hot slurry temperature of 70-75° C.
2. Product filtration of 3-(4-amino-1-oxo-1,3 dihydro-isoindol-2-yl)piperidine-2,6-dione at 65-75° C.
3. Drying under vacuum at 60-70° C. is preferred for an efficient removal of unbound water in 3-(4-amino-1-oxo-1,3 dihydro-isoindol-2-yl)-piperidine-2,6-dione wet cake.
4. The filtration step of 3-(4-amino-1-oxo-1,3 dihydro-isoindol-2-yl)-piperidine-2,6-dione may be a time sensitive operation. The use of efficient solid-liquid separation equipment is preferred.
5. Holding periods of water-wet cake of 3-(4-amino-1-oxo-1,3 dihydro-isoindol-2-yl)-piperidine-2,6-dione at KF higher than 5% may cause the kinetic equilibrations of polymorph B to mixed polymorphs of E and B.

Drying to KF<4.0% water was achieved in ~3 hours (30-70° C., 152 mm Hg). Polymorphs B and E were distinguished by the water levels as measured by KF and TGA. The reference sample of polymorph B is micronized API. In order to make accurate comparison by XRPD samples were gently grinded before submission for analysis. This increases the clarity of the identification of the polymorphic form. All samples were analyzed for XRPD, DSC, TGA, KF and HPLC.

TABLE 1

Preliminary Studies

| Amount | Reaction conditions | Analysis | Results/conclusion |
|---|---|---|---|
| 2 g | Water, rt, 48 h | XRPD, DSC, TGA, KF | Polymorph E |
| 25 g | Water, rt, 48 h | XRPD, DSC, TGA, KF | Polymorph E |
| 5 g | Water, 70-75° C., 24 h then rt 24 h | XRPD, DSC, TGA, KF | Polymorph B |
| 1 g | 9:1 Acetone - water, Slow evpo. | XRPD, DSC, TGA, KF | Polymorph Mixture |
| 1 g | 175° C. 1 h in an oven | XRPD, DSC, TGA, KF | Polymorph A |
| 0.5 g (polymorph A) | Water, rt, 24 h | XRPD, DSC, TGA, KF | Polymorph E |
| 1 g polymorph B | Water, rt, 48 h | XRPD, DSC, TGA, KF | Polymorph E |
| 1 g polymorph E | Water, 70-75° C., 24 h | XRPD, DSC, TGA, KF | Polymorph B |
| 1 g | Slurry in heptane | XRPD, DSC, TGA, KF | No change |

TABLE 2

Optimization of Temperature, Time and Solvent Volume

| Amount | Amount Water (mL) | Temp (° C.) | Time (h) | Results/conclusion |
|---|---|---|---|---|
| 10 g | 50 | 75 | 6 | Mix |
| 10 g | 50 | 75 | 24 | Polymorph B |
| 10 g | 100 | 70 | 6 | Polymorph B |
| 10 g | 100 | 70 | 14 | Polymorph B |
| 10 g | 100 | 70 | 21 | Polymorph B |
| 10 g | 100 | 75 | 6 | Polymorph B |
| 10 g | 100 | 75 | 24 | Polymorph B |
| 10 g | 100 | 75 | 6 | Polymorph B |
| 10 g | 100 | 75 | 19 | Polymorph B |
| 10 g | 100 | 75 | 14 | Polymorph B |
| 10 g | 100 | 75 | 24 | Polymorph B |
| 5 g | 100 | 75 | 18 | Polymorph B |
| 10 g | 100 | 80 | 6 | Polymorph B |
| 10 g | 100 | 80 | 20 | Polymorph B |
| 10 g | 200 | 45 | 6 | Polymorph B + E |
| 10 g | 200 | 45 | 24 | Polymorph E |
| 10 g | 200 | 60 | 48 | Polymorph B |
| 10 g | 200 | 75 | 6 | Mix |
| 10 g | 200 | 75 | 24 | Polymorph B |
| 10 g | 200 | 75 | 13 | Polymorph B |
| 10 g | 200 | 75 | 24 | Polymorph B |

Optimum conditions were determined to be 10 volumes of solvent (H$_2$O), 70-80° C. for 6-24 hours.

TABLE 3

Holding Time

| Amount | Reaction Conditions | Holding Time (h) | Holding Temp (° C.) | Results/Conclusion |
|---|---|---|---|---|
| 5 g | Water, 70-75° C., 24 h | 24 | 23-25 | Polymorph B |
| 1 g Polymorph B | Water, 70-75° C., 24 h | 48 | 23-25 | Polymorph E |
| 2 g | Water, 40 mL | 16 | 23-25 | Polymorph E |
| 150 g | Water, 3.0 L | 24 | 23-25 | Polymorph E |
| 150 g | Water, 3.0 L | 48 | 23-25 | Polymorph E |
| 10 g | Water, 100 mL, 24 h, 75° C. | 18 | 23-25 | Polymorph B |
| 10 g | Water, 100 mL, 24 h, 75° C. | 18 | 40 | Polymorph B |
| 10 g | Water, 200 mL, 24 h, 75° C. | 14 | −5 | Mix |
| 10 g | Water, 200 mL, 24 h, 75° C. | 14 | 23-25 | Polymorph E |
| 10 g | Water, 200 mL, 24 h, 75° C. | 14 | 40 | Mix |
| 10 g | Water, 100 mL, 24 h, 75° C. | 21 | 23-25 | Polymorph E |
| 10 g | Water, 100 mL, 24 h, 75° C. | 21 | 40 | Mix |
| 10 g | Water, 100 mL, 14 h, 75° C. | 2 | 23-25 | Mix |

Holding time gave mixed results and it was determined that the material should be filtered at 60-65° C. and the material washed with 0.5 volume of warm (50-60° C.) water.

TABLE 4

Scale-up Experiments

| Amount | Amount Water (L) | Temp (° C.) | Time (h) | Results/Conclusion |
|---|---|---|---|---|
| 100 g | 1.0 | 75 | 6 | Polymorph B |
| 100 g | 1.0 | 75 | 22 | Polymorph B |

TABLE 4-continued

Scale-up Experiments

| Amount | Amount Water (L) | Temp (° C.) | Time (h) | Results/Conclusion |
|---|---|---|---|---|
| 100 g | 1.0 | 75 | 6 | Polymorph B |
| 100 g | 1.0 | 75 | 24 | Polymorph B |
| 100 g | 1.0 | 75 | 6 | Polymorph B |
| 100 g | 1.0 | 75 | 22 | Polymorph B |

TABLE 5

Drying Studies

| Amount | Drying Time (h) | Drying Temp (° C.) | Vacuum (mm Hg) | KF§ (%) | Results/Conclusion |
|---|---|---|---|---|---|
| 100 g | 0 | — | — | 3.690 | Polymorph B |
| 100 g | 3 | 30 | 152 | 3.452 | Polymorph B |
| 100 g | 8 | 30 | 152 | 3.599 | Polymorph B |
| 100 g | 0 | — | — | 3.917 | Polymorph B |
| 100 g | 5 | 40 | 152 | 3.482 | Polymorph B |
| 100 g | 22 | 40 | 152 | 3.516 | Polymorph B |
| 100 g | 3 | 40 | 152 | 3.67 | Polymorph B |
| 100 g | 22 | 40 | 152 | 3.55 | Polymorph B |

*Reaction Conditions: Water 1 L, 75° C., 22-24 h;
§Average of 2 runs.

Drying studies determined that the material should be dried at 35-40° C., 125-152 mm Hg for 3 to 22 h or until the water content reaches ≦4% w/w.

For a large scale preparation of polymorph E (5222-152-B), a 5-L round bottom flask was charged with 3-(4-amino-1-oxo-1,3 dihydro-isoindol-2-yl)-piperidine-2,6-dione (150 g, 0.579 mol) and water (3000 mL, 20 vol). The mixture was mechanically stirred at room temperature (23-25° C.) for 48 h under nitrogen atmosphere.

Samples were taken after 24 h and 48 h before the mixture was filtered and air-dried on the filter for 1 h The material was transferred to a drying tray and dried at room temperature (23-25° C.) for 24 h. KF analysis on the dried material showed water content of 11.9%. The material was submitted for XRPD, TGA, DSC and HPLC analysis. Analysis showed the material was pure polymorph E.

For a large scale preparation of polymorph B (5274-104), a 2 L-3-necked round bottom flask was charged with 3-(4-amino-1-oxo-1,3 dihydro-isoindol-2-yl)-piperidine-2,6-dione (polymorph mixture, 100 g, 0.386 mol) and water (1000 mL, 10.0 vol). The mixture was heated to 75° C. over approximately 30 minutes with mechanical stirring under nitrogen atmosphere.

Samples were taken after 6 h and 24 h before the mixture was allowed to cool to 60-65° C., filtered and the material washed with warm (50-60° C.) water (50 mL, 0.5 vol). The material was transferred to a drying tray and dried at 30° C., 152 mm Hg for 8 h. KF analysis on the dried material showed water content of 3.6%. After grinding the material was submitted for XRPD, TGA, DSC and HPLC analysis. Analysis showed the material was pure polymorph B. The results of the analyses are shown in FIGS. 32-46.

6.3 X-Ray Powder Diffraction Measurements

X-ray powder diffraction analyses were carried out on a Shimadzu XRD 6000 X-ray powder diffractometer using Cu Kα radiation. The instrument is equipped with a fine-focus X-ray tube. The tube voltage and amperage were set at 40 kB and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 degrees 2θ to 40 degrees 2θ was used. A silicon standard was analyzed each day to check the instrument alignment.

X-ray powder diffraction analyses were also carried out using Cu Kα radiation on an Inel XRG-3000 diffractometer equipped with a curved position-sensitive detector. Data were collected in real time over a theta-two theta range of 120° at a resolution of 0.03°. The tube voltage and current were 40 kV and 30 mA, respectively. A silicon standard was analyzed each day to check for instrument alignment. Only the region between 2.5 and 40 degrees 2θ is shown in the figures.

6.4 Thermal Analysis

TG analyses were carried out on a TA Instrument TGA 2050 or 2950. The calibration standards were nickel and alumel. Approximately 5 mg of sample was placed on a pan, accurately weighed, and inserted into the TG furnace. The samples were heated in nitrogen at a rate of 10° C./min, up to a final temperature of 300 or 350° C.

DSC data were obtained on a TA 2920 instrument. The calibration standard was indium. Approximately 2-5 mg samples were placed into a DSC pan and the weight accurately recorded. Crimped pans with one pinhole were used for analysis and the samples were heated under nitrogen at a rate of 10° C./min, up to a final temperature of 350° C.

Hot-stage microscopy was carried out using a Kofler hot stage mounted on a Leica Microscope. The instrument was calibrated using USP standards.

A TA Instruments TGA 2050 interfaced with a Nicolet model 560 Fourier transform IR spectrophotometer, equipped with a globar source, XT/KBr beamsplitter, and deuterated triglycine sulfate (DTGS) detector, was utilized for TG-IR experiments. The IR spectrometer was wavelength calibrated with polystyrene on the day of use while the TG was temperature and weight calibrated biweekly, using indium for the temperature calibration. A sample of approximately 10 mg of 3-(4-amino-1-oxo-1,3 dihydro-isoindol-2-yl)-piperidine-2,6-dione was weighed into an aluminum pan and heated from 25 to 30° C. to 200° C. at a rate of 20° C./min with a helium purge. IR spectra were obtained in series, with each spectrum representing 32 co-added scans at a resolution of 4 cm$^{-1}$. Spectra were collected with a 17-second repeat time. TG/IR analysis data are presented as Gram-Schmidt plots and IR spectra linked to the time. Gram-Schmidt plots show total IR intensity vs. time; hence, the volatiles can be identified at each time point. They also show when the volatiles are detected. From the Gram-Schmidt plots, time points were selected and the IR spectra of these time points are presented in the stacked linked spectra Each spectrum identifies volatiles evolving at that time point. Volatiles were identified from a search of the HR Nicolet TGA vapor phase spectral library. The library match results are also presented to show the identified vapor.

6.5 Spectroscopy Measurements

Raman spectra were acquired on a Nicolet model 750 Fourier transform Raman spectrometer utilizing an excitation wavelength of 1064 nm and approximately 0.5 W of Nd:YAG laser power. The spectra represent 128 to 256 co-added scans acquired at 4 cm$^{-1}$ resolution. The samples were prepared for analysis by placing the material in a sample holder and positioning this in the spectrometer. The spectrometer was wavelength calibrated using sulfur and cyclohexane at the time of use.

The mid-IR spectra were acquired on a Nicolet model 860 Fourier transform IR spectrophotometer equipped with a globar source XT/KBr beamsplitter and a deuterated triglycine sulfate (DTGS) detector. A Spectra-Tech, Inc. diffuse reflectance accessory was utilized for sampling. Each spectrum represents 128 co-added scans at a spectral resolution of 4 cm$^{-1}$. A background data set was acquired with an alignment mirror in place. A single beam sample data set was then acquired. Subsequently, a log 1/R (where R=reflectance) spectrum was acquired by rationing the two data sets against each other. The spectrophotometer was calibrated (wavelength) with polystyrene at the time of use.

6.6 Moisture Sorption/Desorption Measurements

Moisture sorption/desorption data were collected on a VTI SGA-100 moisture balance system. For sorption isotherms, a sorption range of 5 to 95% relative humidity (RH) and a desorption range of 95 to 5% RH in 10% RH increments was used for analysis. The sample was not dried prior to analysis. Equilibrium criteria used for analysis were less than 0.0100 weight percent change in 5 minutes with a maximum equilibration time of 3 hours if the weight criterion was not met. Data were not corrected for the initial moisture content of the samples.

6.7 Solution Proton NMR Measurements

NMR spectra not previously reported were collected at SSCI, Inc, 3065 Kent Avenue, West Lafayette, Ind. Solution phase $^1$H NMR spectra were acquired at ambient temperature on a Bruker model AM spectrometer. The $^1$H NMR spectrum represents 128 co added transients collected with a 4 μsec pulse and a relaxation delay time of 5 seconds. The free induction decay (FID) was exponentially multiplied with a 0.1 Hz Lorentzian line broadening factor to improve the signal-to-noise ratio. The NMR spectrum was processed utilizing GRAMS software, version 5.24. Samples were dissolved in dimethyl sulfoxide-d$_6$.

The scope of this invention can be understood with reference to the appended claims.

6.8 Intrinsic Dissolution and Solubility Studies

Intrinsic dissolution experiments were conducted on Form A (anhydrous), Form B (hemihydrate), and Form E (dihydrate) of 3-(4-amino-1-oxo-1,3 dihydro-isoindol-2-yl)-piperidine-2,6-dione. Equilibrium solubility experiments were conducted on Forms A and B. Aliquots were analyzed by ultraviolet-visible spectrophotometry, and the solids remaining from each experiment were analyzed by X-ray powder diffraction (XRPD).

6.8.1 Experimental
6.8.1.1 Dissolution

Dissolution experiments were carried out in a VanKel VK6010-8 dissolution apparatus equipped with a VK650A heater/circulator. An intrinsic dissolution apparatus (Woods apparatus) was used. Samples were compressed at 1.5 metric tons (1000 psi) for 1 min using the Woods apparatus in a hydraulic press, giving a sample surface of 0.50 cm$^2$. A dissolution medium consisting of 900 mL HCl buffer, pH 1.8, with 1% sodium lauryl sulfate, was used for each experiment. The medium was degassed by vacuum filtration through a 0.22-μm nylon filter disk and maintained at 37° C. The apparatus was rotated at 50 rpm for each experiment. Aliquots were filtered immediately using 0.2-μM nylon syringe filters. In some cases, the undissolved solids were recovered and analyzed by X-ray powder diffraction (XRPD).

6.8.1.2 Solubility

Equilibrium solubility experiments were conducted in a 100-mL, three-neck, round-bottom flask immersed in a constant temperature oil bath maintained at 25° C. A solid sample of 400-450 mg was stirred in 50 mL of dissolution medium (HCl buffer, pH 1.8, with 1% sodium lauryl sulfate) using a mechanical stir rod. Aliquots were filtered using 0.2-μm nylon syringe filters and immediately diluted 1 mL→50 mL, then 5 mL→25 mL with dissolution medium in Class A glassware, a final dilution factor of 250.

6.8.1.3 UV-Vis Spectrophotometry

Dissolution and solubility samples solutions were analyzed by a Beckman DU 640 single-beam spectrophotometer. A 1.000-cm quartz cuvette and an analysis wavelength of 228.40 nm were utilized. The detector was zeroed with a cuvette filled with dissolution medium.

6.8.1.4 X-Ray Powder Diffraction

XRPD analyses were carried out on a Shimadzu XRD-6000 X-ray powder diffractometer using Cu Kα radiation. The instrument is equipped with a fine focus X-ray tube. The tube power and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed each day to check the instrument alignment. Samples were packed in an aluminum holder with silicon insert.

6.8.2 Results

The results of these solubility and intrinsic studies are summarized in Table 6. Both the solubility and dissolution experiments were conducted in a medium of HCl buffer, pH 1.8, containing 1% sodium lauryl sulfate. Form A was found to be unstable in the medium, converting to Form E. The solubilities of Forms A, B, and E were estimated to be 6.2, 5.8, and 4.7 mg/mL, respectively. The dissolution rates of Forms A, B, and E were estimated to be 0.35, 0.34, and 0.23 mg/mL, respectively.

6.8.2.1 UV-Vis Spectrophotometry Method Development

A UV-Vis scan of the dissolution medium (blanked with an empty cuvette) was done to identify any interfering peaks. A small peak at 225 nm was present as shown in FIG. 47.

Solutions of 3-(4-amino-1-oxo-1,3 dihydro-isoindol-2-yl)-piperidine-2,6-dione at varying concentrations were analyzed by UV-Vis spectrophotometry. A preliminary scan of a 1.0 mg/mL solution was done, with the instrument blanked with dissolution medium. The solution was highly absorbing and noisy from 200-280 nm, making dilution necessary.

A 0.04 mg/mL solution of 3-(4-amino-1-oxo-1,3 dihydro-isoindol-2-yl)-piperidine-2,6-dione was then scanned from 200-300 nm. The plot was still noisy between 200 and 230 nm as shown in FIG. 48. The sample was further diluted to 0.008 mg/mL. A wavelength scan of 200-350 nm for this sample showed a peak a 228.4 nm with no interference, as shown in FIG. 49. Therefore, a wavelength of 228.4 was chosen for analysis of the solubility and dissolution samples.

A six-point calibration curve was generated with standards of the following concentrations: 0.001 mg/mL, 0.002 mg/mL, 0.005 mg/mL, 0.010 mg/mL, 0.015 mg/mL, and 0.020 mg/mL (Notebook 569-90). A linearity coefficient of $R^2$=0.9999 was obtained as shown in FIG. 50.

6.8.2.2 Solubility

A sample consisting of 449.4 mg Form A was slurried in dissolution medium. Particle size was not controlled. Aliquots were taken at 7, 15, 30, 60, 90, and 150 min. The concentration reached 6.0 mg/mL by the first time point The highest concentration reached was 6.2 mg/mL, at 30 min. From that point the concentration decreased, reaching 4.7 mg/mL at 150 min as in FIG. 51. The solids remaining at the final time point were analyzed by XRPD and found to be Form E as shown in Table 7. No peaks attributed to Form A can be seen in the pattern. Since the concentration did not plateau at 4.7 mg/mL, the solubility of Form E may be lower than that.

A sample consisting of 401.4 mg Form B was slurried in dissolution medium. Particle size was not controlled. Aliquots were taken at 7, 15, 30, 60, 90, 180, 420, and 650 min. Form B dissolved much more slowly than Form A, reaching 3.3 mg/mL in 90 min. The concentration stabilized at 5.6-5.7 mg/mL at the final three time points as in FIG. 52. The remaining solids were shown to be Form B as in Table 7, suggesting Form B has good stability in water.

A summary of the solubilities is given in Table 6. The amounts dissolved at each time point are shown in Tables 8 and 9.

TABLE 6

Summary of Results

| Form | Solubility | Intrinsic Dissolution #1 | Intrinsic Dissolution #2 | Average Intrinsic Dissolution Rate |
|---|---|---|---|---|
| Form A | 6.2 mg/mL | 0.35 | 0.22$^a$ | 0.29$^a$ |
| Form B | 5.8 mg/mL | 0.35 | 0.32 | 0.34 |
| Form E | 4.7 mg/mL | 0.21 | 0.25 | 0.23 |

$^a$The Form A dissolution experiment #2 may have converted to Form E on the surface of the disk, skewing the average rate lower.

TABLE 7

Experimental Details

| Experiment | Final Form |
|---|---|
| Pressed Form A | A |
| Pressed Form B | B |
| Form A Solubility | E |
| Form B Solubility | B |
| Form A Dissolution | — |
| Form A Dissolution | A |
| Form B Dissolution | — |
| Form B Dissolution | B |
| Form E Dissolution | E |
| Form E Dissolution | — |

TABLE 8

Form A Solubility

| Time Point (min) | Concentration (mg/mL) |
|---|---|
| 7 | 6.00 |
| 15 | 6.11 |
| 30 | 6.16 |
| 60 | 6.10 |
| 90 | 5.46 |
| 150 | 4.73 |

TABLE 9

Form B Solubility

| Time Point (min) | Concentration (mg/mL) |
|---|---|
| 7 | 1.63 |
| 15 | 2.14 |
| 30 | 2.33 |
| 60 | 2.94 |
| 90 | 3.34 |
| 180 | 5.67 |
| 420 | 5.76 |
| 650 | 5.61 |

6.8.2.3 Intrinsic Dissolution

Approximately 200 mg each of Forms A and B were compressed into disks in the Woods apparatus using 2 metric tons of pressure. The samples were subsequently scraped out, ground gently, and analyzed by XRPD. The study showed that compression and grinding does not cause a form change in either case. (See Table 7).

Two preliminary dissolution runs were performed. The disks fractured to some extent in both experiments, compromising the requirement of constant surface area.

The first experiment of intrinsic dissolution that strictly followed the USP chapter on intrinsic dissolution utilized approximately 150 mg each of Forms A and B. Seven aliquots, beginning at 5 min and ending at 90 min, were taken to maintain sink conditions. The experiment resulted in linear dissolution profiles, with a rate of 0.35 mg per cm$^2$ per minute for both forms. The Form E experiment was done later under the same conditions and added to the graph for comparison. (See FIG. 53). The Form E dissolution rate was 0.21 mg per cm$^2$ per minute, significantly lower than the dissolution rate of Forms A and B. This is in line with expectations based on the solubility data The crystal form of the remaining solids did not change in any case.

The second experiment utilized approximately 250 mg each of Forms A and B. The Form E experiment (135 mg) was done later and added to the graph for comparison. (See FIG. 54). Nine aliquots were taken, beginning at 5 min and ending at 150 min. The dissolution rates were 0 22, 0.32, and 0.25 mg per cm$^2$ per minute, respectively, for Forms A, B, and E. The dissolution rate for Form A in this experiment was low, while the rates for Forms B and E were similar to those found in the first experiment It is believed that in this case, a thin layer of the Form A sample disk may have converted to Form E upon exposure to water. This is supported by the evidence of rapid conversion of Form A to Form E in the solubility experiment. The diffraction pattern of the undissolved solids does not indicate a form change. However, the bulk of the sample disk is not exposed to water. Therefore, the true intrinsic dissolution rate of Form A is believed to be close to 0.35 mg per cm$^2$ per minute. An insufficient quantity of Form A was available to repeat the experiment.

A summary of the intrinsic dissolution rates is given in Table 6. The amounts dissolved at each time point are summarized in Tables 10 and 11.

TABLE 10

Intrinsic Dissolution Experiment #1 Results

| Time Point | Form A$^a$ | Form B$^a$ | Form E$^a$ |
|---|---|---|---|
| 5 min | 5.76 | 10.80$^b$ | 2.70 |
| 10 min | 7.73 | 6.85 | 4.13 |

TABLE 10-continued

Intrinsic Dissolution Experiment #1 Results

| Time Point | Form A[a] | Form B[a] | Form E[a] |
|---|---|---|---|
| 20 min | 11.31 | 10.25 | 6.96 |
| 30 min | 15.59 | 14.35 | 9.60 |
| 45 min | 21.98 | 20.57 | 12.57 |
| 60 min | 27.11 | 25.70 | 15.16 |
| 90 min | 34.17 | 34.34 | 20.82 |

[a]Results are reported as Cumulative Amount Dissolved per Unit Area (mg/cm2)
[b]This date point not included in graph since the value is higher than the next two data points.

TABLE 11

Intrinsic Dissolution Experiment #2 Results

| Time Point | Form A[a] | Form B[a] | Form E[a] |
|---|---|---|---|
| 5 min | 4.50 | 5.04 | 3.06 |
| 10 min | 5.22 | 6.12 | 4.31 |
| 20 min | 7.54 | 7.73 | 11.40 |
| 30 min | 11.46 | 12.72 | 11.93 |
| 45 min | 15.01 | 17.33 | 14.72 |
| 60 min | 18.38 | 21.93 | 18.52 |
| 90 min | 24.38 | 31.64 | 26.24 |
| 120 min | 30.35 | 41.31 | 33.56 |
| 150 min | 35.26 | 49.54 | 40.82 |

[a]Results are reported as Cumulative Amount Dissolved per Unit Area (mg/cm2)

6.9 Analyses of Mixtures of Polymorphs

This invention encompasses mixtures of different polymorphs. For example, an X-ray diffraction analysis of one production sample yielded a pattern that contained two small peaks seen at approximately 12.6° and 25.8° 2θ in addition to those representative of Form B. In order to determine the composition of that sample, the following steps were performed.

1) Matching of the new production pattern to known forms along with common pharmaceutical excipients and contaminants;
2) Cluster analysis of the additional peaks to identify if any unknown phase is mixed with the original Form B;
3) Harmonic analysis of the additional peaks to identify if any preferred orientation may be present or if any changes in the crystal habit may have occurred; and
4) Indexing of the unit cells for both Form B and the new production sample to identify any possible crystallographic relationships.

Based on these tests, which can be adapted for the analysis of any mixture of polymorphs, it was determined that the sample contained a mixture of polymorph forms B and E.

6.10 Dosage Form

Table 12 illustrates a batch formulation and single dosage formulation for a 25 mg single dose unit of a polymorphic form of 3-(4-amino-1-oxo-1,3 dihydro-isoindol-2-yl)-piperidine-2,6-dione.

TABLE 12

Formulation for a 25 mg capsule

| Material | Percent By Weight | Quantity (mg/tablet) | Quantity (kg/batch) |
|---|---|---|---|
| Polymorphic Form of 3-(4-amino-1-oxo-1,3 dihydro-isoindol-2-yl)-piperidine-2,6-dione | 40.0% | 25 mg | 16.80 kg |
| Pregelatinized Corn Starch, NF | 59.5% | 37.2 mg | 24.99 kg |
| Magnesium Stearate | 0.5% | 0.31 mg | 0.21 kg |
| Total | 100.0% | 62.5 mg | 42.00 kg |

The pregelatinized corn starch (SPRESS B-820) and polymorphic form of 3-(4-amino-1-oxo-1,3 dihydro-isoindol-2-yl)-piperidine-2,6-dione components are passed through a screen (i.e., a 710 μm screen) and then loaded into a Diffusion Mixer with a baffle insert and blended for about 15 minutes. The magnesium stearate is passed through a screen (i.e., a 210 μm screen) and added to the Diffusion Mixer. The blend is then encapsulated in capsules using a Dosator type capsule filling machine.

The entire scope of this invention is not limited by the specific examples described herein, but is more readily understood with reference to the appended claims.

What is claimed is:

1. A solid form of 3-(4-amino-1-oxo-1,3 dihydro-isoindol-2-yl)-piperidine-2,6-dione comprising crystalline 3-(4-amino-1-oxo-1,3 dihydro-isoindol-2-yl)-piperidine-2,6-dione hemihydrate, wherein the crystalline 3-(4-amino-1-oxo-1,3 dihydro-isoindol-2-yl)-piperidine-2,6-dione hemihydrate is present at greater than about 80% by weight of the solid form.

2. A solid form of 3-(4-amino-1-oxo-1,3 dihydro-isoindol-2-yl)-piperidine-2,6-dione comprising crystalline 3-(4-amino-1-oxo-1,3 dihydro-isoindol-2-yl)-piperidine-2,6-dione hemihydrate, wherein the crystalline 3-(4-amino-1-oxo-1,3 dihydro-isoindol-2-yl)-piperidine-2,6-dione hemihydrate is present at greater than about 90% by weight of the solid form.

3. A solid form of 3-(4-amino-1-oxo-1,3 dihydro-isoindol-2-yl)-piperidine-2,6-dione comprising crystalline 3-(4-amino-1-oxo-1,3 dihydro-isoindol-2-yl)-piperidine-2,6-dione hemihydrate, wherein the crystalline 3-(4-amino-1-oxo-1,3 dihydro-isoindol-2-yl)-piperidine-2,6-dione hemihydrate is present at greater than about 95% by weight of the solid form.

4. A solid form of 3-(4-amino-1-oxo-1,3 dihydro-isoindol-2-yl)-piperidine-2,6-dione comprising crystalline 3-(4-amino-1-oxo-1,3 dihydro-isoindol-2-yl)-piperidine-2,6-dione hemihydrate, wherein the crystalline 3-(4-amino-1-oxo-1,3 dihydro-isoindol-2-yl)-piperidine-2,6-dione hemihydrate is present at greater than about 97% by weight of the solid form.

5. A pharmaceutical composition comprising a therapeutically effective amount of the solid form of claim 1, 2, 3, or 4, and a pharmaceutically acceptable excipient or carrier.

6. The pharmaceutical composition of claim 5, which is a single unit dosage form.

7. The pharmaceutical composition of claim 5, wherein the therapeutically effective amount is about 5 mg.

8. The pharmaceutical composition of claim 5, wherein the therapeutically effective amount is about 10 mg.

9. The pharmaceutical composition of claim 5, wherein the therapeutically effective amount is about 25 mg.

10. The pharmaceutical composition of claim 5, wherein the therapeutically effective amount is about 50 mg.

* * * * *

UNITED STATES PATENT AND TRADEMARK OFFICE
CERTIFICATE OF CORRECTION

| | | |
|---|---|---|
| PATENT NO. | : 7,855,217 B2 | Page 1 of 11 |
| APPLICATION NO. | : 12/335395 | |
| DATED | : December 21, 2010 | |
| INVENTOR(S) | : Jaworsky et al. | |

It is certified that error appears in the above-identified patent and that said Letters Patent is hereby corrected as shown below:

Please replace Drawing Sheets 15, 26, 31, 32, 33, 35, 36, 38, 39, and 40 (of 48) with the Replacement Drawing Sheets on the following pages of this Certificate of Correction:

Page 2 of 11: Replacement Drawing Sheet 15 of 48 (Fig. 15);

Page 3 of 11: Replacement Drawing Sheet 26 of 48 (Fig. 26);

Page 4 of 11: Replacement Drawing Sheet 31 of 48 (Fig. 31);

Page 5 of 11: Replacement Drawing Sheet 32 of 48 (Figs. 32 and 33);

Page 6 of 11: Replacement Drawing Sheet 33 of 48 (Figs. 34 and 35);

Page 7 of 11: Replacement Drawing Sheet 35 of 48 (Figs. 37 and 38);

Page 8 of 11: Replacement Drawing Sheet 36 of 48 (Figs. 39 and 40);

Page 9 of 11: Replacement Drawing Sheet 38 of 48 (Figs. 42 and 43);

Page 10 of 11: Replacement Drawing Sheet 39 of 48 (Figs. 44 and 45);

Page 11 of 11: Replacement Drawing Sheet 40 of 48 (Fig. 46).

Signed and Sealed this
Third Day of May, 2011

David J. Kappos
*Director of the United States Patent and Trademark Office*

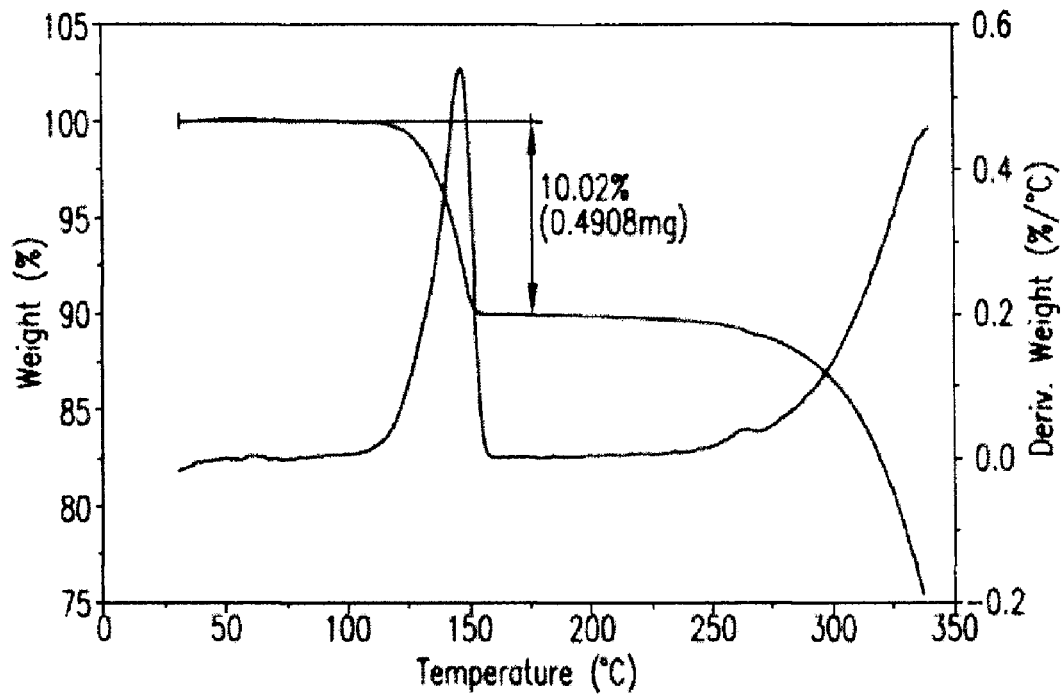
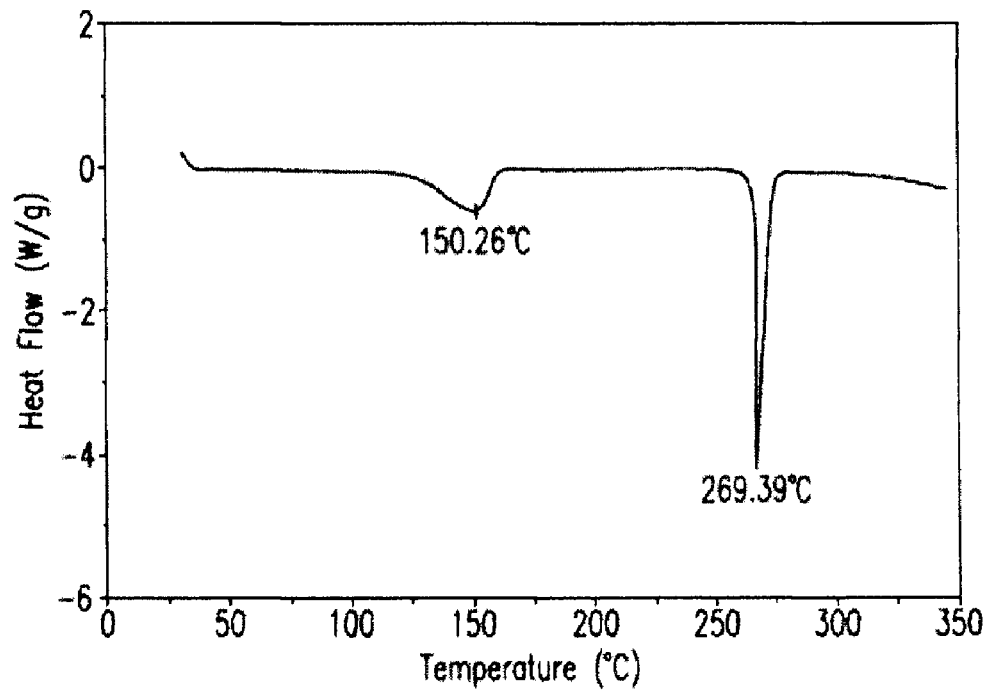
FIG.15